US007041096B2

(12) United States Patent
Malis et al.

(10) Patent No.: US 7,041,096 B2
(45) Date of Patent: May 9, 2006

(54) ELECTROSURGICAL GENERATOR APPARATUS

(75) Inventors: Jerry L. Malis, King of Prussia, PA (US); Leonard I. Malis, Queens, NY (US); Robert R. Acorcey, Cherry Hill, NJ (US); David L. Solt, Fort Washington, PA (US); Anthony John Groch, Mantua, NJ (US)

(73) Assignee: Synergetics USA, Inc., O'Fallon, MO (US)

( * ) Notice: Subject to any disclaimer, the term of this patent is extended or adjusted under 35 U.S.C. 154(b) by 0 days.

(21) Appl. No.: 10/279,572

(22) Filed: Oct. 24, 2002

(65) Prior Publication Data

US 2004/0082946 A1    Apr. 29, 2004

(51) Int. Cl.
*A61B 18/18* (2006.01)

(52) U.S. Cl. .......................................... 606/34; 606/38
(58) Field of Classification Search ............ 606/32–34, 606/37–41
See application file for complete search history.

(56) References Cited

U.S. PATENT DOCUMENTS

| | | | | |
|---|---|---|---|---|
| 3,898,590 A | * | 8/1975 | Swanson ..................... | 332/152 |
| 4,038,984 A | * | 8/1977 | Sittner ......................... | 606/37 |
| 4,590,934 A | | 5/1986 | Malis et al. | |
| 4,658,820 A | * | 4/1987 | Klicek ......................... | 606/37 |
| 4,716,897 A | | 1/1988 | Noguchi et al. | |
| 4,727,874 A | | 3/1988 | Bowers et al. | |
| 4,903,696 A | | 2/1990 | Stasz et al. | |
| 4,934,377 A | | 6/1990 | Bova et al. | |
| 4,961,739 A | * | 10/1990 | Thompson ................... | 606/37 |
| 5,167,658 A | * | 12/1992 | Ensslin ........................ | 606/34 |
| 5,318,563 A | * | 6/1994 | Malis et al. .................. | 606/38 |
| 5,370,645 A | * | 12/1994 | Klicek et al. ................ | 606/35 |
| 6,055,458 A | * | 4/2000 | Cochran et al. ............. | 700/17 |

* cited by examiner

Primary Examiner—Michael Peffley
(74) Attorney, Agent, or Firm—Akin Gump Strauss Hauer & Feld, LLP

(57) ABSTRACT

An electrosurgical generator apparatus controls a variable output signal to electrodes. The generator apparatus operates in a cut mode, a coagulation mode or a stimulate mode. The generator apparatus comprises a DC power supply that provides regulated low voltage and high voltage outputs and a radio frequency (RF) waveform generator circuit that provides pulse duration modulation (PDM) of a carrier signal. The carrier signal directly affects the variable output signal to the electrodes. A control circuit controls a variable output signal to electrodes used in electrosurgical procedures. The control circuit comprises a DC power supply circuit that provides regulated low voltage and high voltage outputs and an RF waveform generator circuit that provides pulse duration modulation of a carrier signal. The carrier signal directly affects the variable output signal to the electrodes.

12 Claims, 41 Drawing Sheets

20 KHZ - 4 PHASE REFERENCE GENERATOR

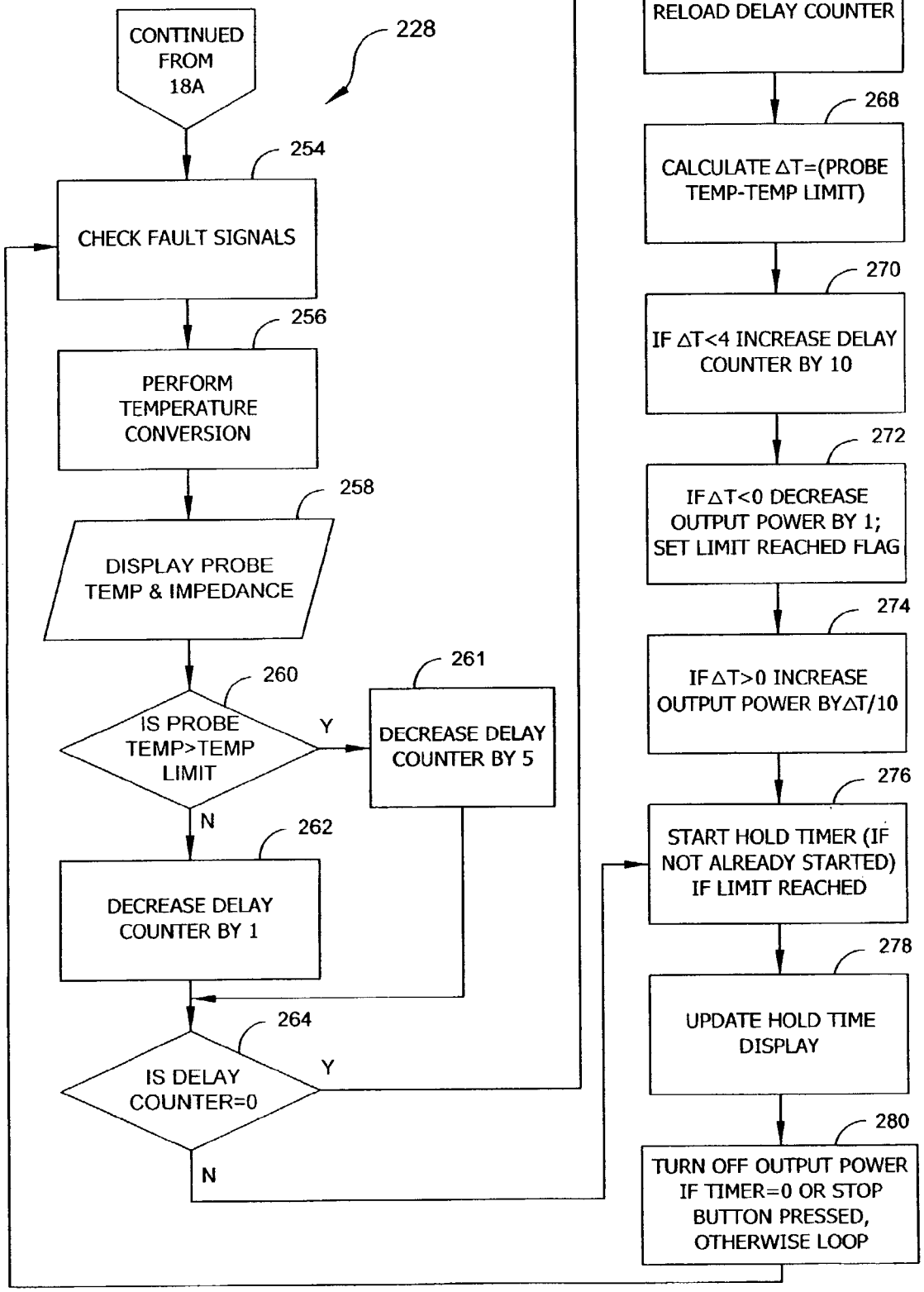

ELECTROSURGICAL GENERATOR APPARATUS

BACKGROUND OF THE INVENTION

The present invention relates to an electrosurgical generator apparatus for controlling mono-polar electrode tools, bipolar electrode tools or other electrode structures and, more particularly, an electrosurgical generator apparatus using radio frequency (RF) modulation and having a unique user interface.

Devices used for controlling mono-polar and bipolar electrode tools are well known in the art. U.S. Pat. No. 5,318,563, the subject matter of which is hereby incorporated herein by reference, relates to electrosurgical RF generators. The electrodes in the prior art systems are used for cutting and coagulation of tissue. Typically the electrodes are installed in an insulated probe or similar device for safe handling by a user during use as is known in the art. The user interface of the prior art systems relies upon knobs, dials, pushbuttons, analog and digital gauges and indicator lights to provide the user with the ability to adjust presets and limits and to monitor the output to the electrodes and the feedback from the electrodes and associated sensors. The only user settings are those established by the last adjustment made to the knobs, dials and pushbuttons.

The output of the waveform of the prior art electrosurgical RF generators are controlled by RF modulation and an analog circuit. The waveforms of the prior art generators provide adequate cutting and coagulating without secondary damage.

Some prior art electrosurgical RF generators utilize feedback from the electrodes to determine whether there is an open circuit in the probe (disconnected or damaged), a short circuit in the probe or even the magnitude of the impedance measured between the electrodes at the tip of the probe. This provides added information and warning signals to the user.

While the prior art apparatus and methods for controlling electrodes with an RF generator all function adequately, there is a need for a more advanced electrosurgical RF generator apparatus. What is needed, but not provided in the prior art devices, is a user interface that allows more intuitive and advanced settings capabilities. Further, what is needed, but not provided in the prior art devices, is an electrosurgical RF generator that allows the storage of user or procedure settings in memory for simple retrieval. Further, what is needed, but not provided in the prior art devices, is an electrosurgical RF generator that allows more precise control of the output waveform and additional functions of the output waveform. Even further, what is needed, but not provided in the prior art devices, is an electrosurgical RF generator that provides monitoring of the overall impedance or complex impedance as measured through the electrodes. The present invention provides such an advanced electrosurgical generator apparatus.

BRIEF SUMMARY OF THE INVENTION

Briefly stated, the present invention comprises a control circuit that controls a variable output signal to electrodes used in electrosurgical procedures. The control circuit comprises a DC power supply circuit that provides regulated low voltage and high voltage outputs and a radio frequency (RF) waveform generator circuit that provides pulse duration modulation of a carrier signal. The carrier signal directly affects the variable output signal to the electrodes.

The present invention also comprises an electrosurgical generator apparatus that controls a variable output signal to electrodes. The generator apparatus operates in a cut mode, a coagulation mode or a stimulate mode. The generator apparatus comprises a DC power supply that provides regulated low voltage and high voltage outputs and an RF waveform generator circuit that provides pulse duration modulation of a carrier signal. The carrier signal directly affects the variable output signal to the electrodes.

The present invention also comprises an electrosurgical generator apparatus that controls a variable output signal to electrodes. The generator apparatus operates in a cut mode, a coagulation mode or a stimulate mode. The generator apparatus comprises a DC power supply that provides regulated low voltage and high voltage outputs and an off-line switching power supply that provides a high voltage DC output to an RF waveform generator circuit. The RF waveform generator circuit providing pulse duration modulation of a carrier signal. The carrier signal directly affects the variable output signal to the electrodes.

The present invention also comprises an electrosurgical generator apparatus that controls a variable output signal to electrodes. The generator apparatus operates in a cut mode, a coagulation mode or a stimulate mode. The generator apparatus comprises a controller for controlling the generator apparatus, a memory that stores data for the controller and a touchscreen interface that communicates with the controller to display the data from the memory and that allows a user to enter a setting.

The present invention also comprises an electrosurgical generator apparatus that controls a variable output signal to electrodes. The generator apparatus operates in a cut mode, a coagulation mode or a stimulate mode. The generator apparatus comprises a DC power supply that provides regulated low voltage and high voltage outputs and a radio frequency (RF) waveform generator circuit that provides modulation of a carrier signal. The carrier signal directly affects the variable output signal to the electrodes. The generator apparatus also comprises an impedance monitoring circuit that detects an impedance as measured across a pair of leads of the electrodes. The impedance is correspondingly proportional to an amount of cell destruction caused by the generator apparatus.

The present invention also comprises a method for detecting an amount of cell destruction using an electrosurgical generator apparatus that controls a variable output signal to electrodes. The generator apparatus operates in a cut mode, a coagulation mode or a stimulate mode. The method includes measuring a baseline impedance across a pair of leads of the electrodes with an impedance monitoring circuit when the leads are applied to an area of cell tissue just before a cutting operation, a coagulation operation or a stimulating operation, implementing a selected operation the cutting operation, the coagulation operation or the stimulating operation and measuring a present impedance across the pair of leads of the electrodes with the impedance monitoring circuit during the selected operation. The method also includes determining the amount of cell destruction which has occurred by comparing the present impedance to the baseline impedance, a difference between the impedances being correspondingly proportional to the amount of cell destruction caused by the generator apparatus. The method further includes stopping the selected operation after a predetermined level of cell destruction.

The present invention also comprises a method for measuring impedance using an electrosurgical generator apparatus that controls a variable output signal to electrodes. The generator apparatus operates in a cut mode, a coagulation mode or a stimulate mode. The method includes measuring an impedance across a pair of leads of the electrodes with an impedance monitoring circuit when the leads are applied to an area of tissue. The impedance monitoring circuit includes a bridge in-phase detector, a bridge quadrature detector, a reference in-phase detector and a reference quadrature detector. The method also includes measuring overall signal in-phase components using the bridge in-phase detector and overall signal quadrature components using the bridge quadrature detector, measuring reference signal in-phase components using the reference in-phase detector and measuring reference signal quadrature components using the reference quadrature detector, combining the overall in-phase components and the overall quadrature components and combining the reference in-phase components and the reference quadrature components. The method further includes comparing the combined overall components to the combined reference components to determine the magnitude and angle of the impedance.

The present invention also comprises a method for storing user-defined parameters using an electrosurgical generator apparatus that controls a variable output signal to electrodes. The generator apparatus operates in a cut mode, a coagulation mode or a stimulate mode and has a controller, memory and an user interface. The method includes entering a first user-defined set-up parameter using the user interface, storing the first user-defined set-up parameter in a first memory location in the memory using a program in the controller and selecting the first user-defined parameter using the user interface.

The present invention also comprises a method of controlling an electrosurgical generator apparatus that controls a variable output signal to electrodes. The generator apparatus operates in either a cut mode, a coagulation mode or a stimulate mode and has a controller, memory and a user interface. The method includes setting a temperature setpoint, setting a soak time preset and measuring the actual temperature at the electrodes. The method also includes comparing the actual temperature to the temperature setpoint and controlling an output power of the generator apparatus using an algorithm stored in the memory. The method further includes determining when the actual temperature is approximately equal to the temperature setpoint, starting a timer that compares an elapsed time to the soak time preset and reducing the power of the output signal to the electrodes to approximately zero.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment which are presently preferred. It should be understood, however, that the invention is not limited to the precise arrangement and instrumentality shown. In the drawings:

FIGS. 18A–18B are flow charts depicting a synopsis of the software operation for temperature/lesion control for the control circuit of FIG. 2A.

DETAILED DESCRIPTION OF THE INVENTION

Figure 1A:
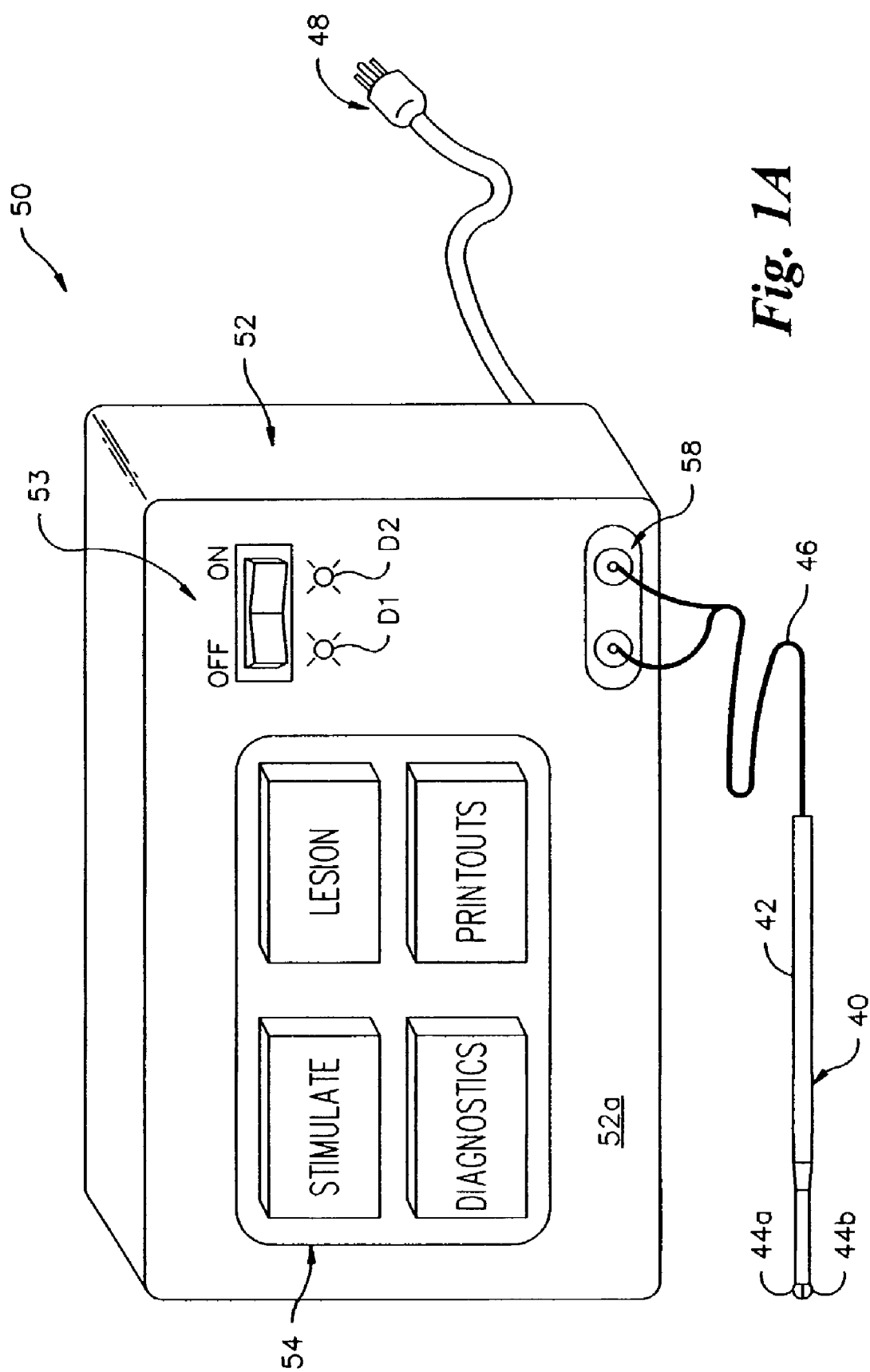
FIG. 1A is a perspective view of a front panel of an electrosurgical generator apparatus in accordance with a preferred embodiment of the present invention along with a bipolar surgical pen.

Certain terminology is used in the following description for convenience only and is not limiting. The words "right," "left," "lower" and "upper" designate directions in the drawings to which reference is made. The words "inwardly" and "outwardly" refer to directions toward and away from respectively, the geometric center of the device discussed and designated parts thereof. The terminology includes the words above specifically mentioned, derivatives thereof and words of similar import. Additionally, the word "a" as used in the claims and in the corresponding portions of the specification, means "one or more than one."

As used herein, a "lesion" is generally any pathological or traumatic discontinuity of tissue or loss of function of a part. Either a "coagulate mode" or a "cut mode" can be used to generate "lesions" when an electrosurgical RF generator is applied as a "lesion generator." Generally, a coagulate mode uses a lower impedance output than a cut mode, about 70 ohms or less, but preferably about 20 ohms, so as not to cut tissue but only to coagulate blood. A coagulate mode typically outputs a decaying waveform. In neurosurgery or other nervous system procedures, a coagulate mode can be used to generate lesions. A cut mode typically uses a much higher impedance than a coagulate mode, such as about 300–500 ohms, but preferably about 400 ohms in order to cut tissue. A cut mode generally uses a non-decaying waveform, such as a continuous sine wave. Preferably, a coagulate mode is used to generate lesions, but the present invention can use cut mode or other different modes to generate lesions. A "stimulate mode" or "stimulator mode" is a lower voltage, power and impedance mode of operating an electrosurgical RF generator which does not cut or coagulate tissue or blood, but merely provides an electrical stimulus for nerves to detect, or cause to be detected, problematic areas of a patient. When an electrosurgical RF generator is being used as a "lesion RF generator," the electrosurgical RF generator can be described as being in a "lesion generate" mode wherein either cut mode or coagulate mode is selected as controlling the output of the electrosurgical RF generator instead of stimulate mode.

An electrosurgical RF generator having the functions and features of the present invention could work equally as well in "coagulate and cut" ("normal") applications as it could in "lesion generate and stimulate" ("lesion") applications. Further, an electrosurgical RF generator having the functions and features of the present invention could also be applied to other electrosurgical RF generators of similar import and should not be considered limited to only the electrosurgical RF generators described herein.

Figure 1B:
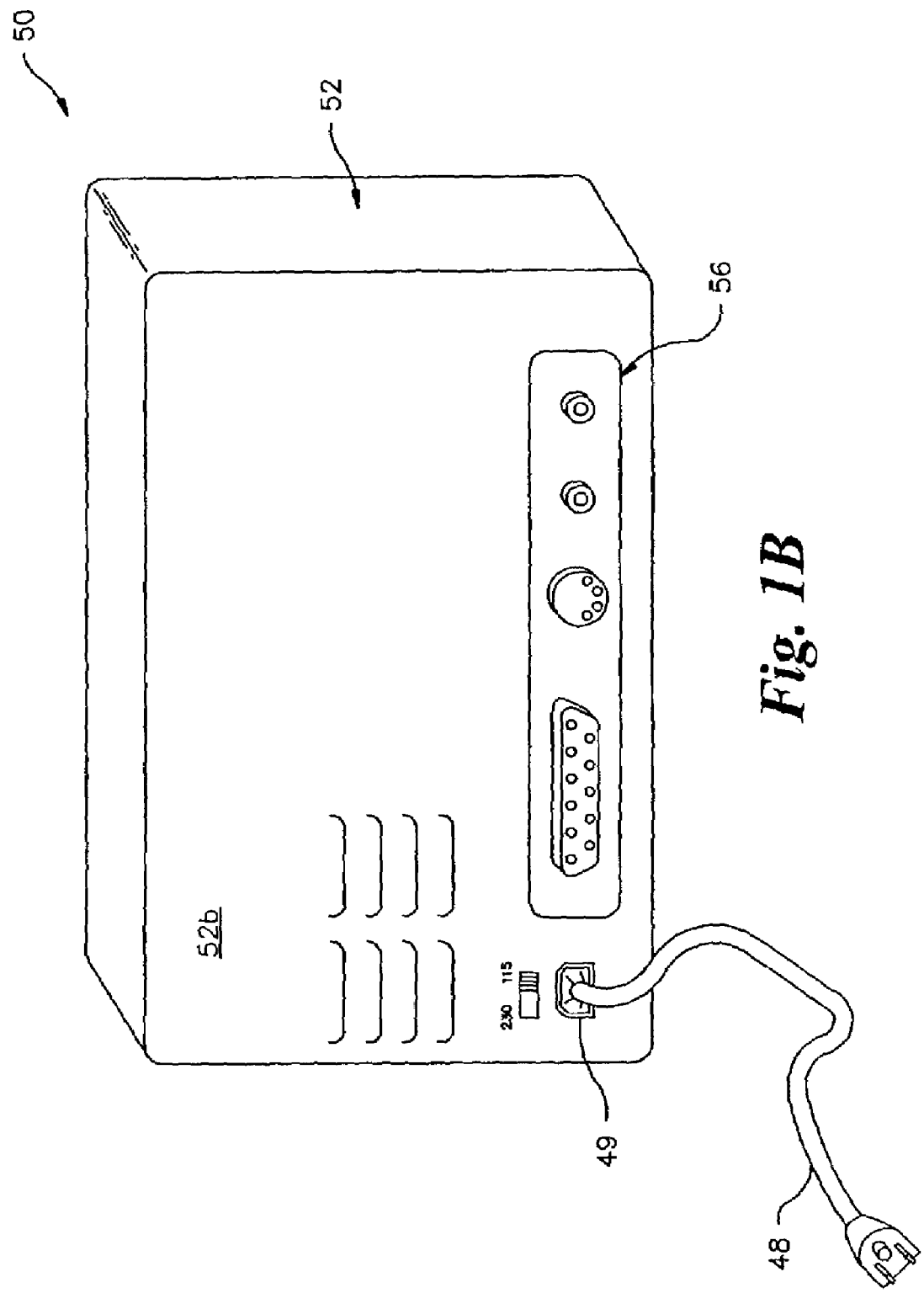
FIG. 1B is a perspective view of a rear panel of the electrosurgical generator of FIG. 1A.

Referring to the drawings in detail, wherein like numerals indicate like elements throughout the several figures, there is shown in FIGS. 1A and 1B a preferred embodiment of an electrosurgical RF generator apparatus or simply RF generator 50 in accordance with the present invention. FIG. 1A is a perspective view of a front panel 52a of the RF generator 50, and FIG. 1B is a perspective view of a rear panel 52b of the RF generator 50.

The RF generator 50 operates in either cut mode or coagulate mode, and the RF generator 50 may also include a stimulate mode, especially when the cut mode and/or coagulate mode are used to generate lesions. Stimulate and lesion generate modes are typically associated with neurosurgery. The stimulate mode is generally used to detect problematic areas that may be causing a patient such symptoms as twitching or pain. Typically a surgeon or other user will apply a stimulate voltage to areas within a patient's brain until the twitching stops, thereby identifying the problematic area. The lesion generate mode is a higher power and impedance mode than the stimulate mode and is used to destroy, scar or otherwise render useless the detected problematic areas. The RF generator has jumpers JMP3, JMP5 which allow selection between "normal" (cut/coagulate modes) and "lesion" (lesion generate/stimulate modes) as described in greater detail hereinafter.

The RF generator 50 includes a housing 52, a touch panel 54 on the front panel 52a and a connector panel 56 on the rear panel 52b. A power cord 48 of the conventional type as is known in the art is connected to a power source to provide power to the RF generator 50 via a source power plug adapter 49. Preferably, the RF generator 50 is supplied with between about 110–125 VAC at 60 Hertz (Hz) or about 220–240 VAC at 50 Hz alternating current (AC). But, other supply voltages and frequencies of AC voltage or other direct current (DC) voltages may be supplied without departing from the present invention.

Preferably, the RF generator 50 is used with a bipolar surgical pen 40 having a cord 46 connected to an output adapter 58 of the RF generator 50. The bipolar surgical pen 40 typically includes a generally elongated insulated handle 42 which is sized to be gripped by a surgeon or other user and which contains a pair of spaced electrodes 44a, 44b. The electrodes 44a, 44b are preferably parallel to one another and partially extend from one end of the bipolar pen 40. The electrodes 44a, 44b are each of opposite polarity such that one electrode is positively charged and the other electrode is negatively charged, alternately, during use. The electrodes 44a, 44b can be of varying sizes, shapes and thicknesses depending upon the particular application. Of course, the RF generator 50 is not limited to use with bipolar surgical pens 40, but may be used with other electrosurgical instruments such as forceps, bulk coagulators, mono-polar electrodes with ground pads, and the like without departing from the broad inventive scope of the present invention.

The RF generator 50 also includes an on/off switch 53 (FIG. 1A) and RF indicator lights D1, D2. The on/off switch 53 is preferably comprised of a two-way toggle type pushbutton having a blue cap for power on and a red cap for power off. The RF indicator lights D1, D2 are preferably blue light emitting diodes (LEDs), but could be other colors or types of lights without departing from the present invention. The on/off switch 53 allows an RF output or a stimulation output to be activated by energizing/de-energizing a high voltage power supply 64 (FIG. 2A).

Figure 3:
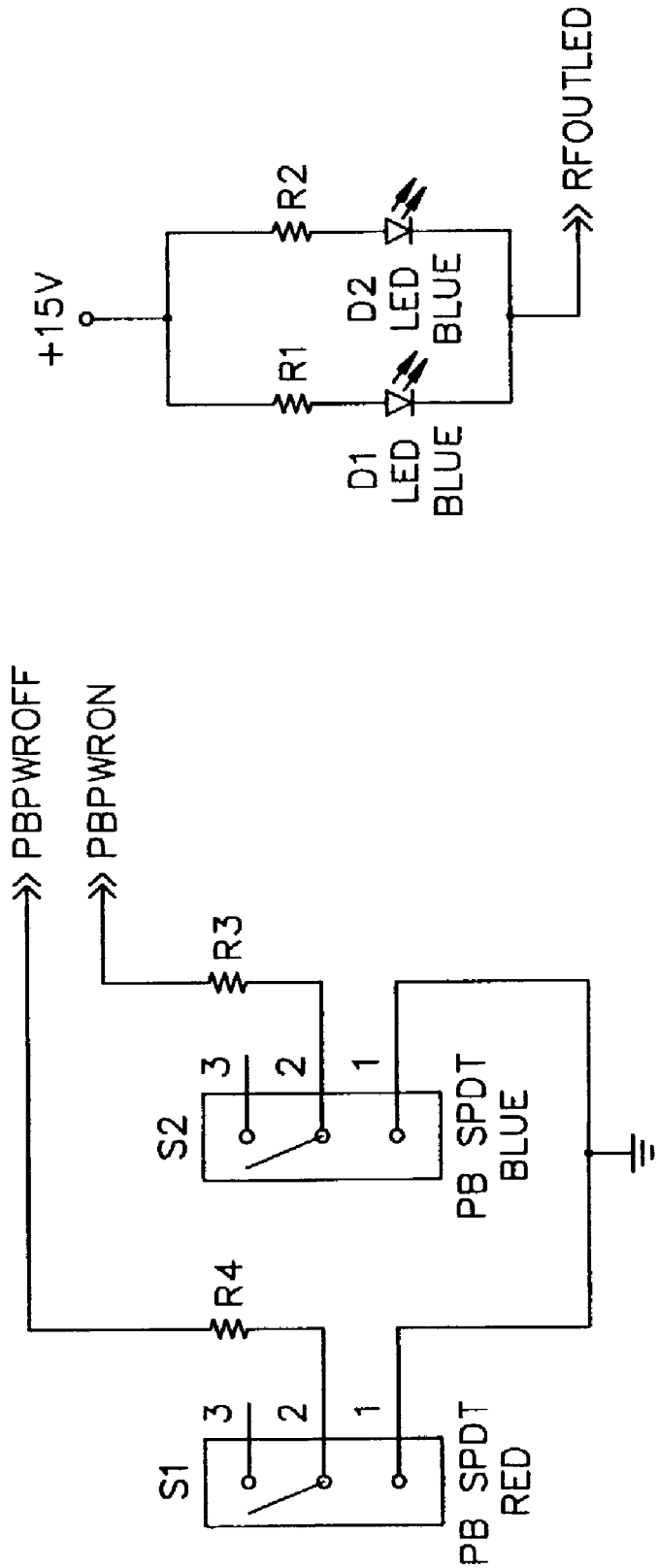
FIG. 3 is a circuit schematic diagram of portions of front panel controls in accordance with the present invention.
Figure 4A:
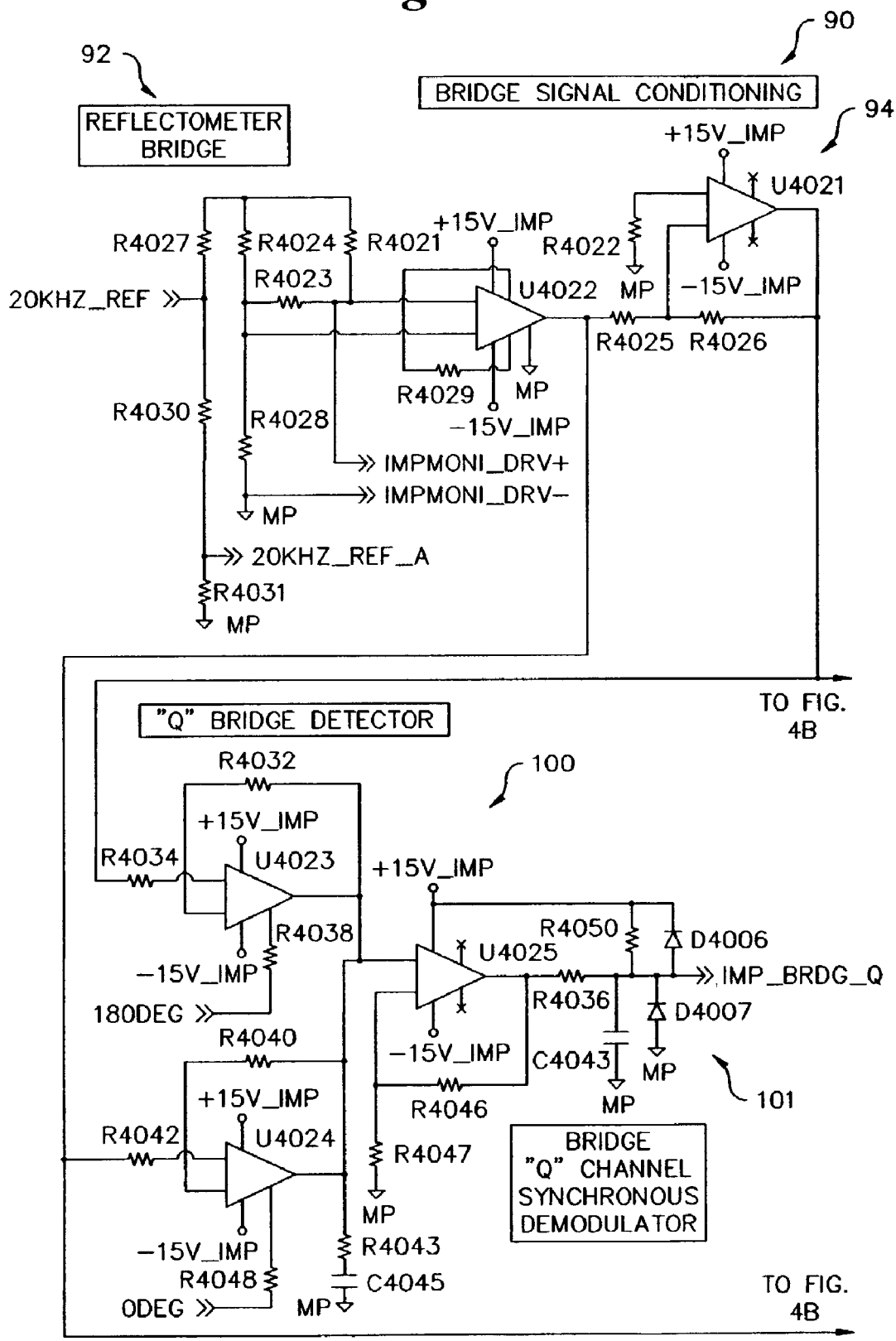
FIGS. 4A–4D are circuit schematic diagrams of an impedance detection circuit for the control circuit of FIG. 2A.
Figure 4B:
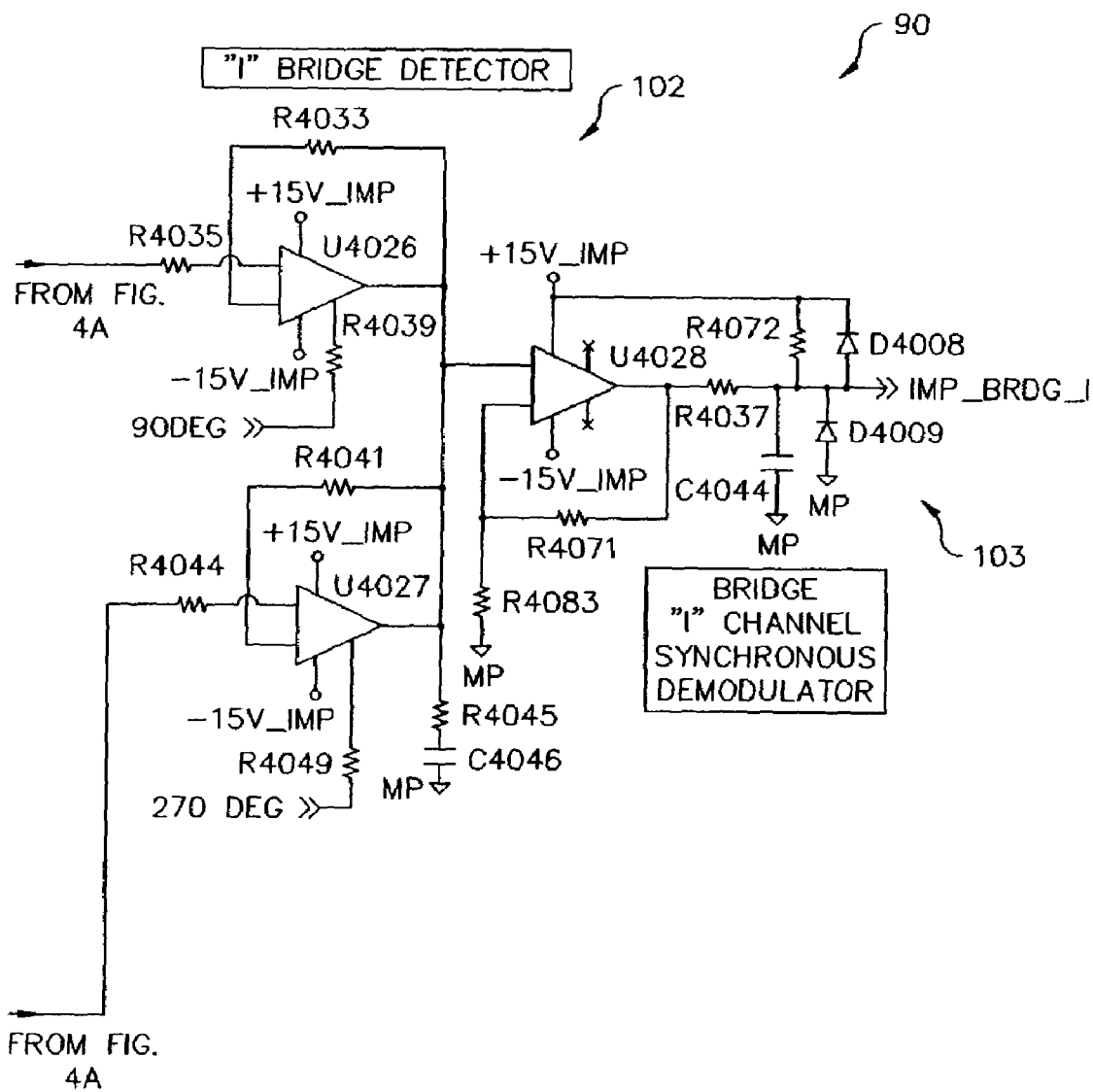
Figure 4C:
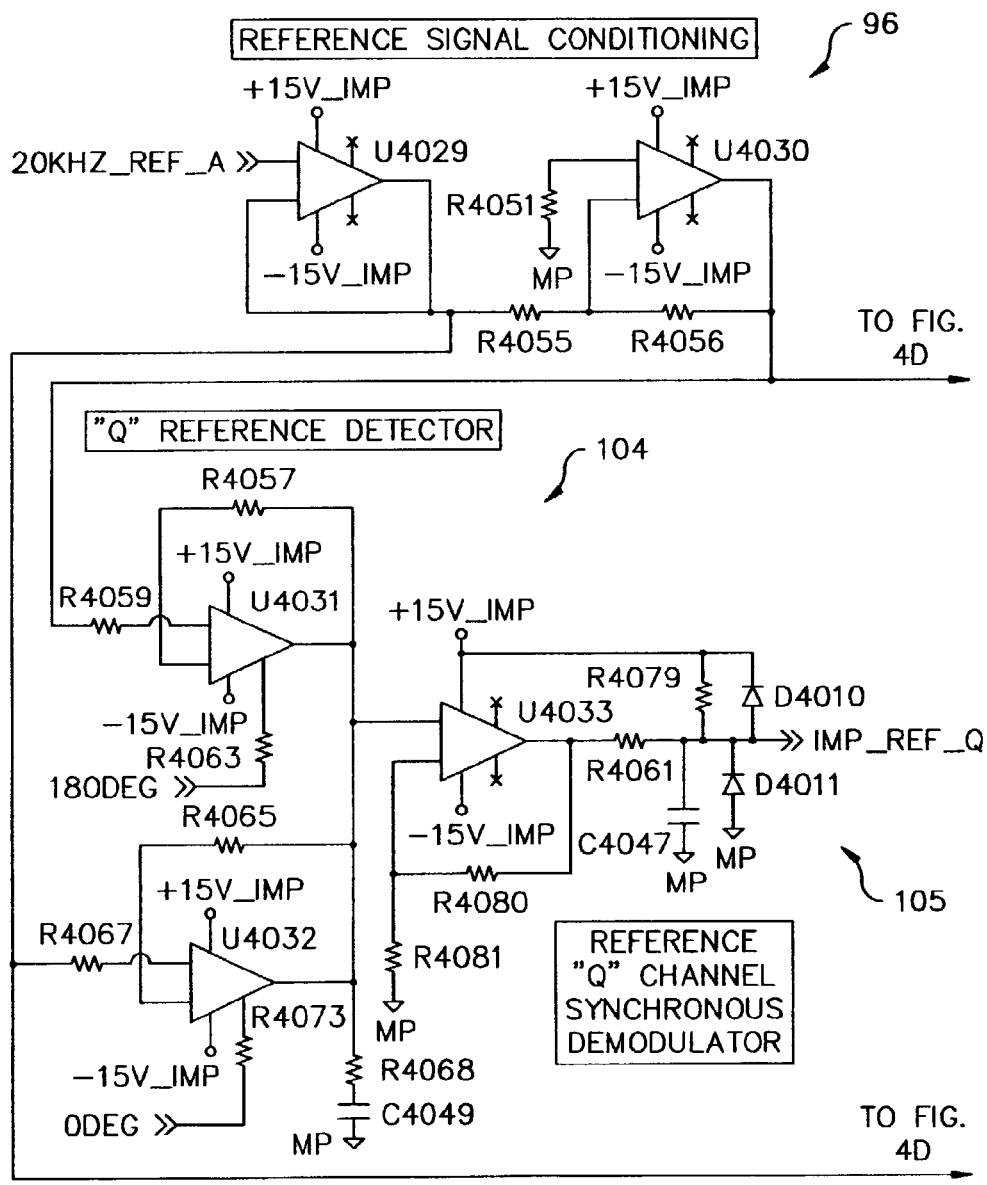
Figure 4D:
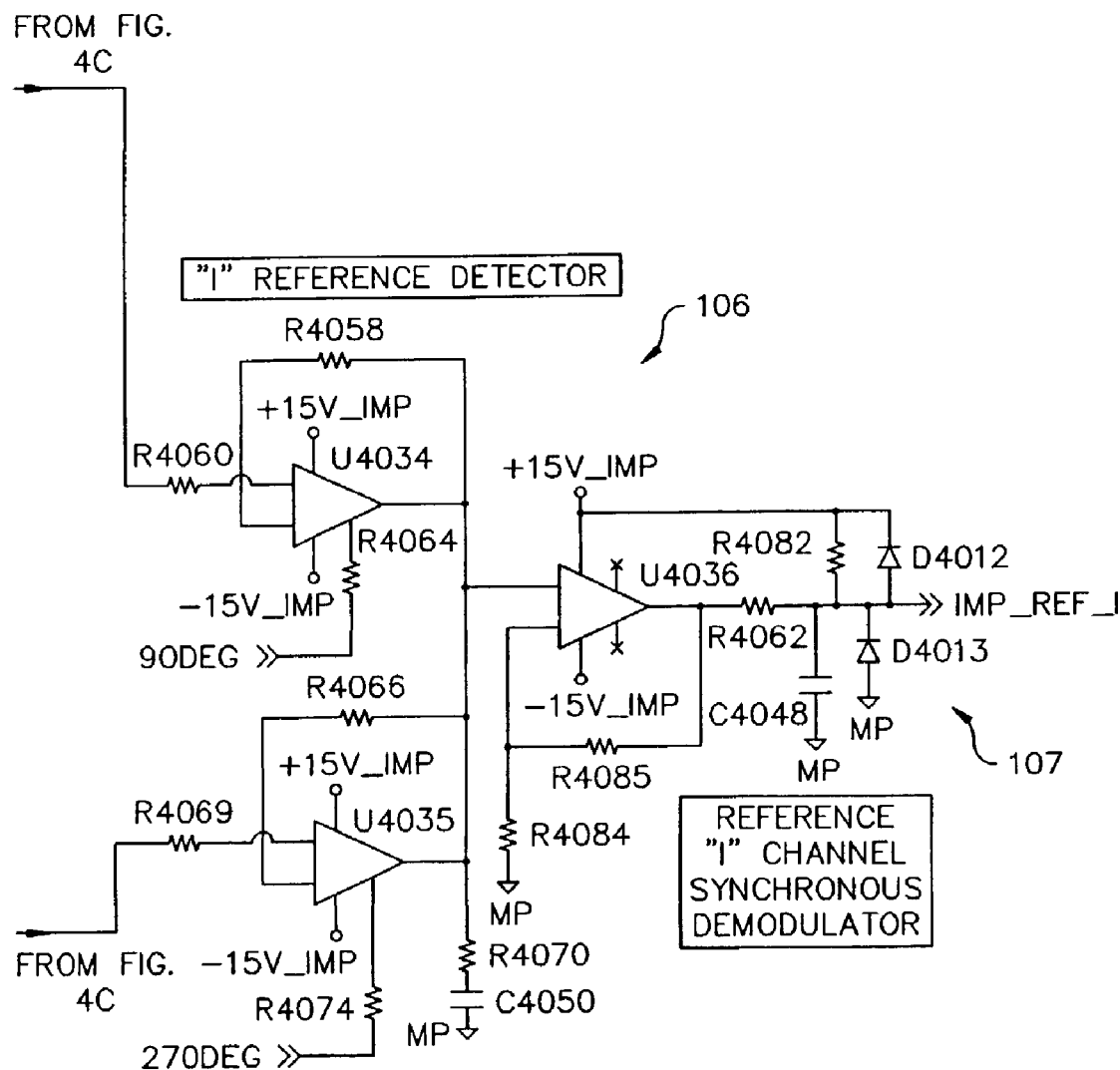

Referring to FIG. 3, front panel controls 57 (FIG. 1A) include an off pushbutton (PB) contact S1, an on PB contact S2 for the on/off switch 53 (FIG. 1A) and first and second RF out LEDs D1, D2, respectively. Preferably, the on and off PB contacts S1, S2 are single-pole, double-throw (SPDT) type pushbutton contacts. The off PB contact S1 is connected to an input of a main controller U1 (FIG. 12) to provide an off PB signal PBPWROFF, and the on PB contact S2 is connected to another input of the main controller U1 to provide an on PB signal PBPWRON.

Preferably, the touch panel or touchscreen 54 is a color, thin film technology (TFT), active matrix-type touchscreen of a type well known in the art. The touchscreen 54 is controlled by a liquid crystal display (LCD) controller or simply display controller 60 (FIG. 2A) and provides inputs to the main controller U1 through an SMT controller 62 (FIG. 2A) as described in greater detail below.

Figure 2A:
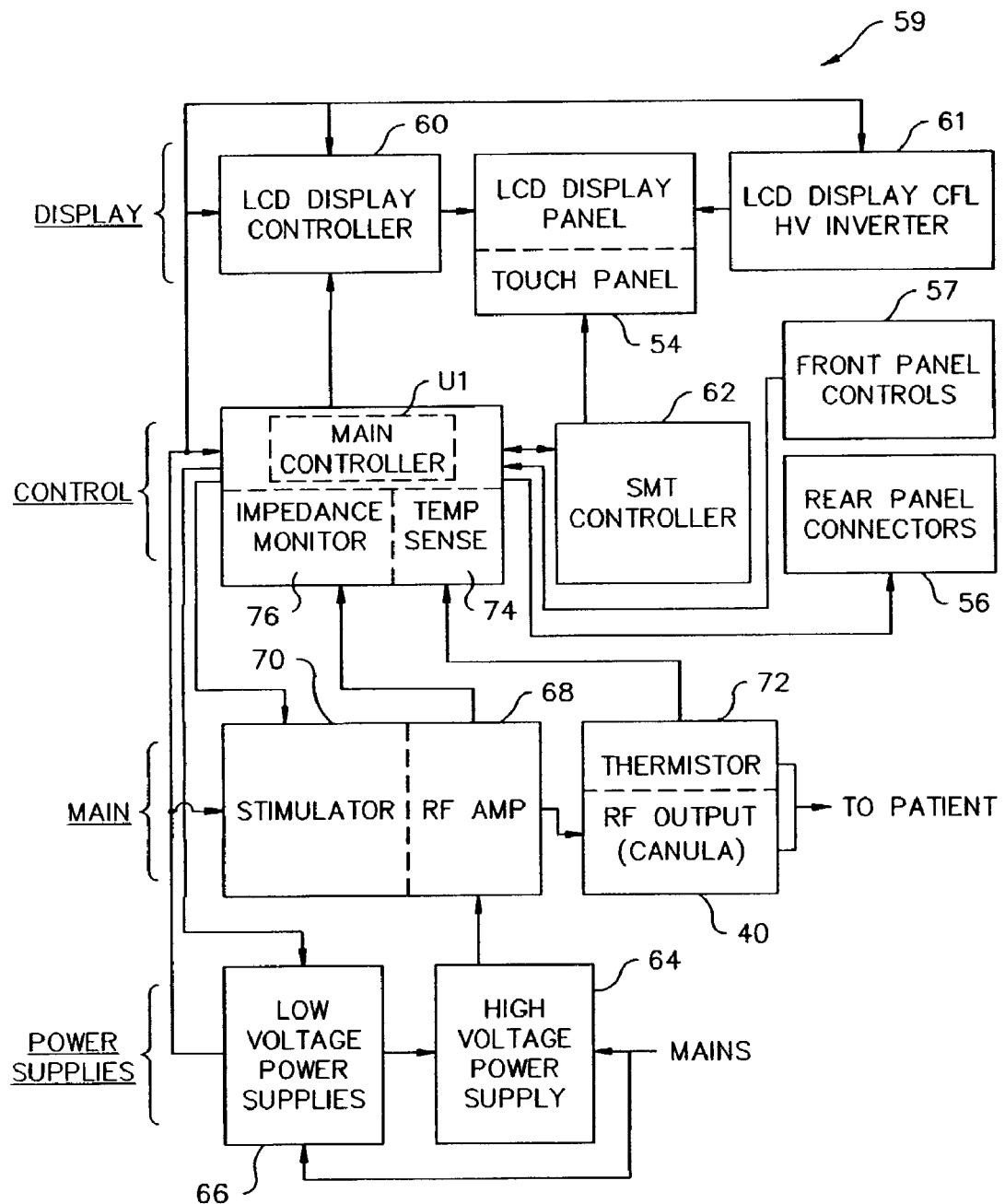
FIG. 2A is a general schematic block diagram of a control circuit for the electrosurgical generator of FIG. 1A.

Referring to FIG. 2A, an overall control circuit 59 for the RF generator 50 is shown in a general block diagram. The control circuit 59 is comprised of multiple sub-circuits forming an overall control system for the RF generator 50. The control circuit 59 includes the main controller U1 and high and low voltage power supplies 64, 66. Preferably, the RF generator 50 includes the high voltage power supply 64 that is an off-line switching power supply to provide high voltage DC output to an RF amplifier circuit 68. The high voltage (HV) power supply 64 receives supply voltage (e.g., 120 VAC, 60 Hz) and serves as the power source for the low voltage power supply 66 and the RF amplifier 68. The RF amplifier 68 includes a stimulator portion 70 (sub-circuit) which applies reduced voltage amplitude or temperature output when selected through screens 120–126 (FIGS. 15A–15G) that interface to software in controllers U1, U1102, U1120 and flash Random Access Memory (RAM) integrated circuit IC or flash memory IC U1108 via the touch panel 54 described in greater detail hereinafter. In the tip of the surgical pen 40 is a thermistor 72 for providing the temperature of the tip of the surgical pen 40 to a temperature sense circuit 74 connected to the main controller U1. The touch panel 54 is controlled by a liquid crystal display (LCD) or simply display controller 60 and is powered by an LCD or simply display CFL high voltage (HV) inverter 61. Inputs from the touchscreen 54 are interfaced through an SMT controller 62. The SMT controller 62 interfaces with the main controller U1. The front panel controls 57 and rear panel connectors 56 provide input/output (I/O) to the control circuit 59. The main controller U1 controls the stimulator circuit 70 and an RF amplifier circuit 68. The RF amplifier circuit 68 in combination with the HV power supply 64 in turn provide outputs to the bipolar surgical pen 40. Feedback from the bipolar surgical pen 40 is sensed by the thermistor 72 in combination with the temperature sense circuit 74 and by an impedance monitor circuit 76. The various control circuits 56, 57, 60, 61, 62, 64, 66, 68, 70, 72, 74, and 76 of the control circuit 59 will hereinafter be described in greater detail.

Figure 2B:
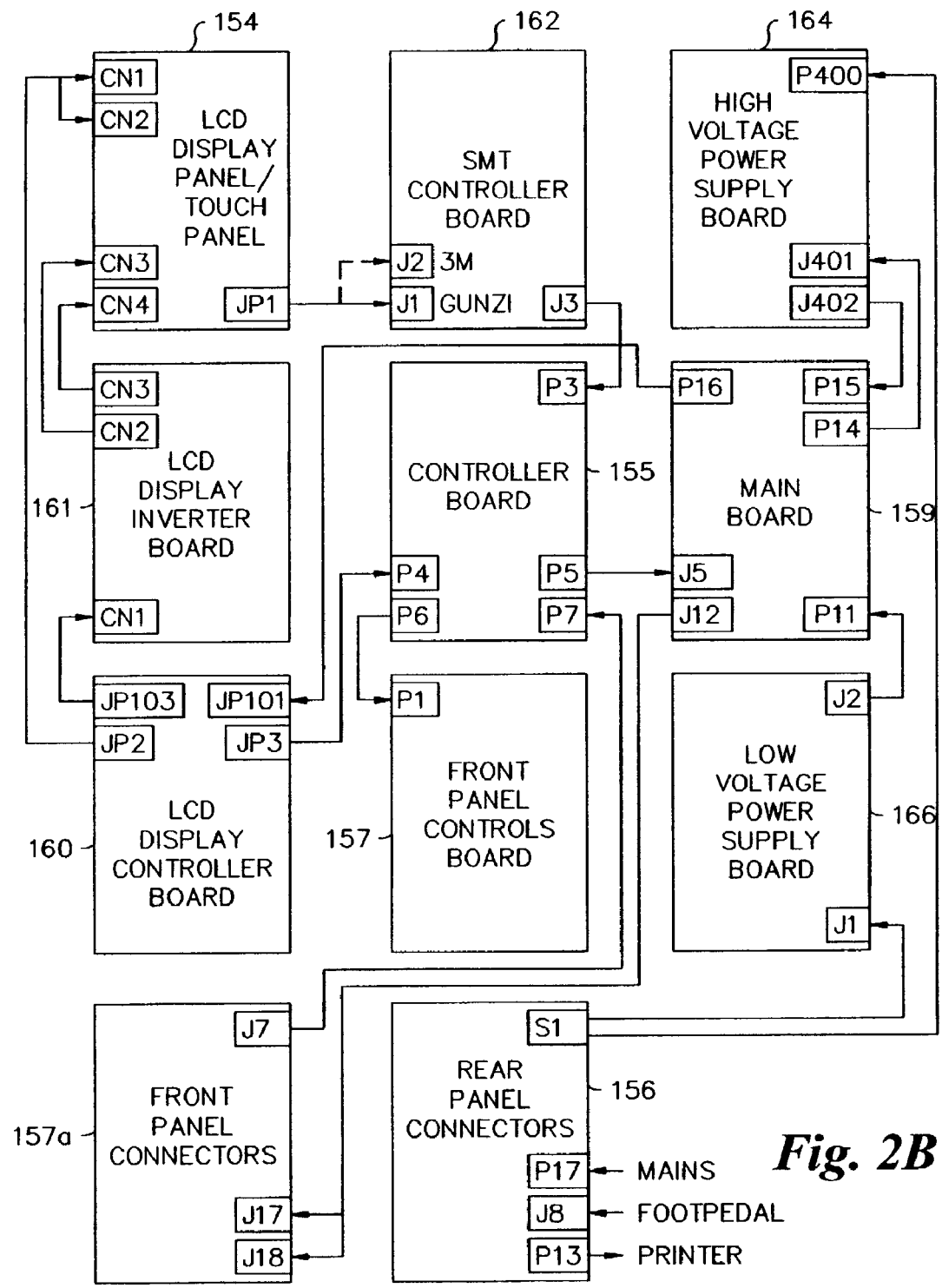
FIG. 2B is a circuit board interconnection diagram for the electrosurgical generator of FIG. 1A.

FIG. 2B shows that the RF generator 50 comprises a plurality of circuit boards 154, 155, 156, 157, 157a, 159, 160, 161, 162, 164, 166 for each of the main functions shown in FIG. 2A. By using separate circuit boards 154, 155, 156, 157, 157a, 159, 160, 161, 162, 164, 166, only a portion of the RF generator 50 needs to be removed or replaced when being upgraded or repaired. The RF generator 50 includes a controller board 155, a main board 159, an LCD display panel board 154, an SMT controller board 162, a rear panel connectors board 156, a front panel control board 157, a front panel connectors board 157a, an LCD display controller 160, an LCD display inverter board 161, a high voltage power supply board 164 and a low voltage power supply board 166. Various cables and connectors interconnect the boards 154, 155, 156, 157, 157a, 159, 160, 161, 162, 164, 166 as is known in the art. Preferably, the boards 154, 155, 156, 157, 157a, 159, 160, 161, 162, 164, 166 are mounted in board slots (not shown) in a chassis (not shown) inside the housing 52 of the RF generator 50 and are interconnected as shown. But, some boards 154, 155, 156, 157, 157a, 159, 160, 161, 162, 164, 166 may be attached to other boards 154, 155, 156, 157, 157a, 159, 160, 161, 162, 164, 166 and/or to walls of the housing 52 as necessary. Of course, the control circuit 59 could be implemented on a single circuit board or other various combinations of circuit boards and circuit implementations without departing from the present invention.

Figure 11A:
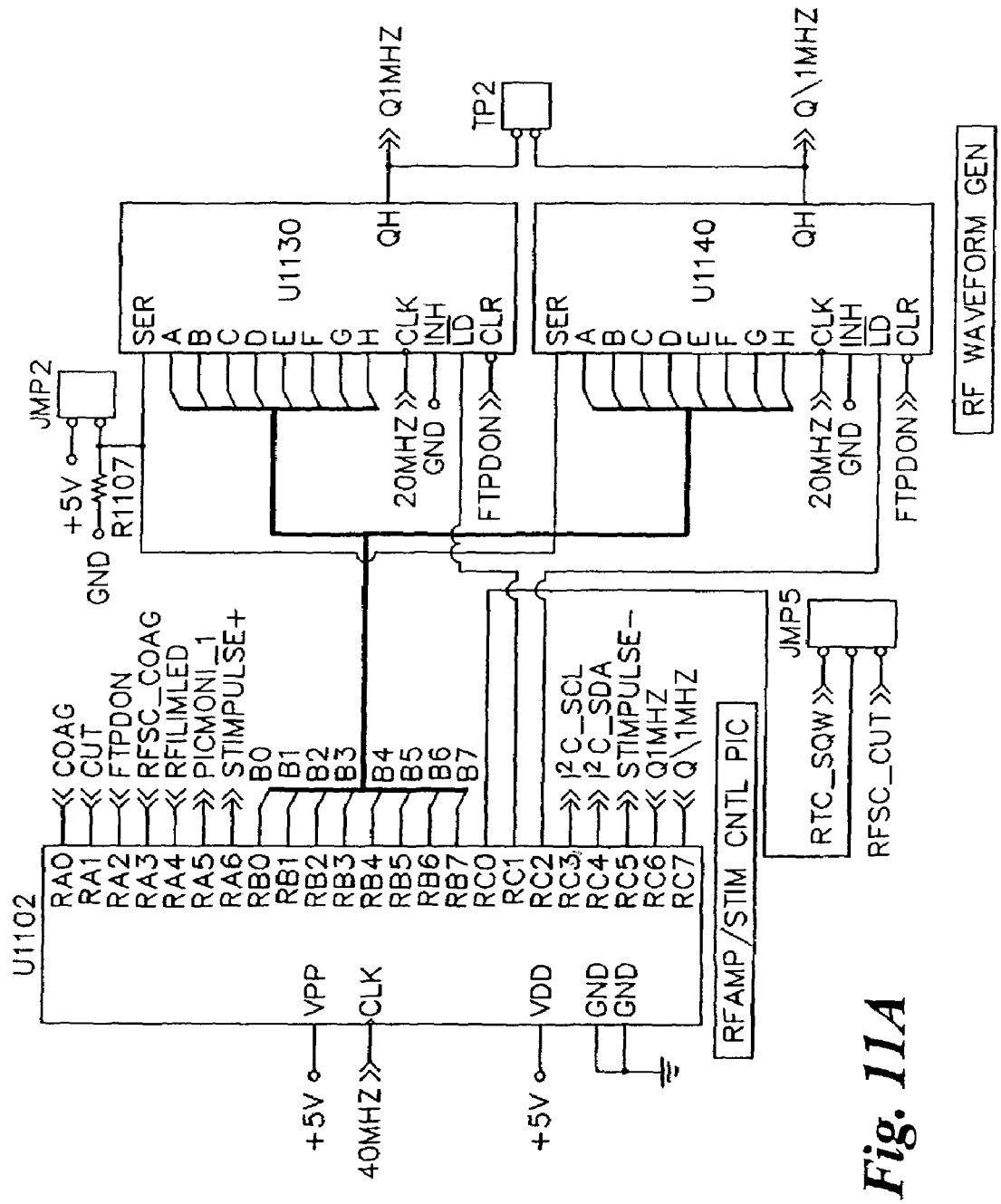
FIGS. 11A–11C are circuit schematic diagrams of various sub-controllers for the control circuit of FIG. 2A.
Figure 11B:
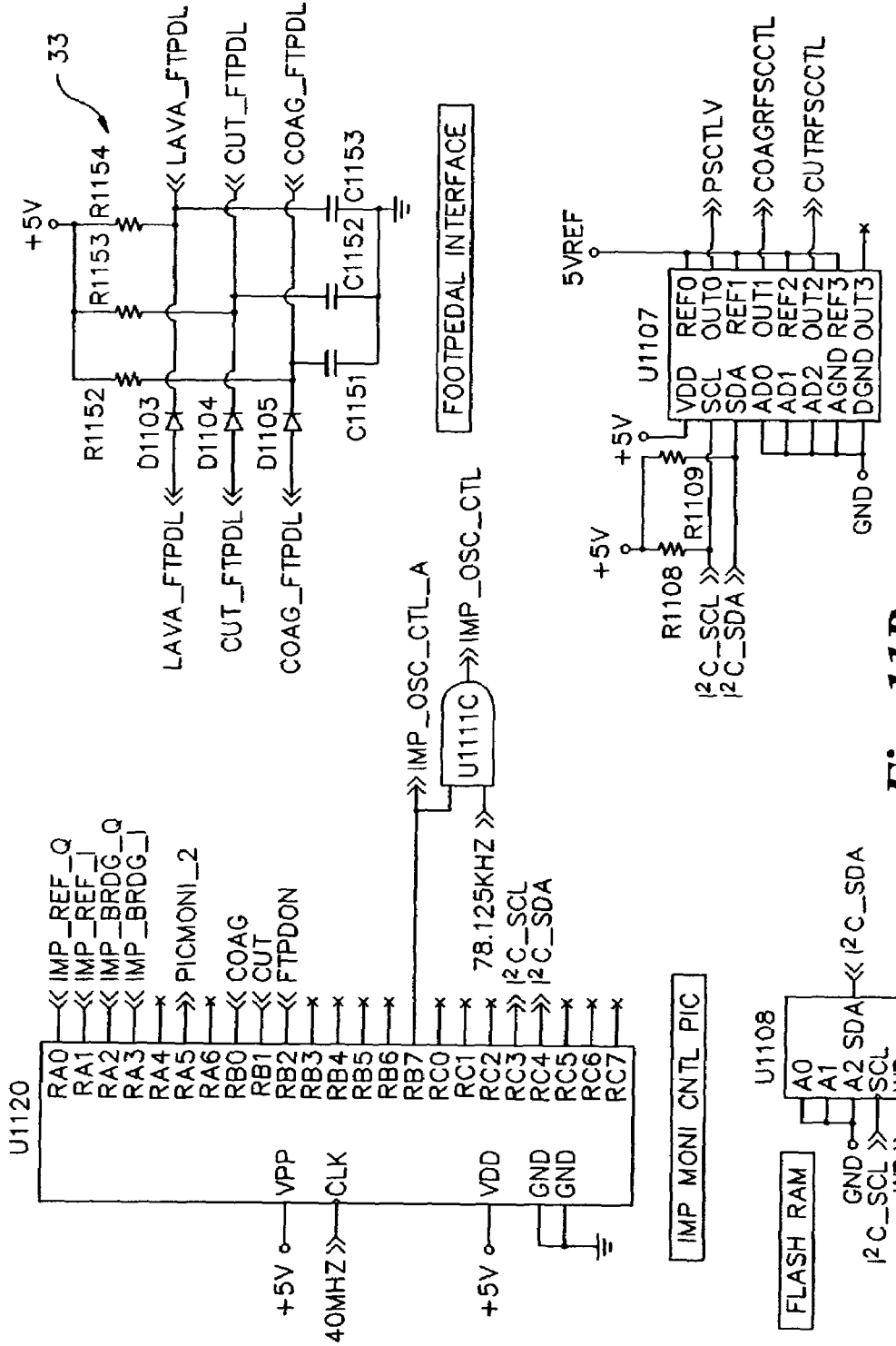
Figure 11C:
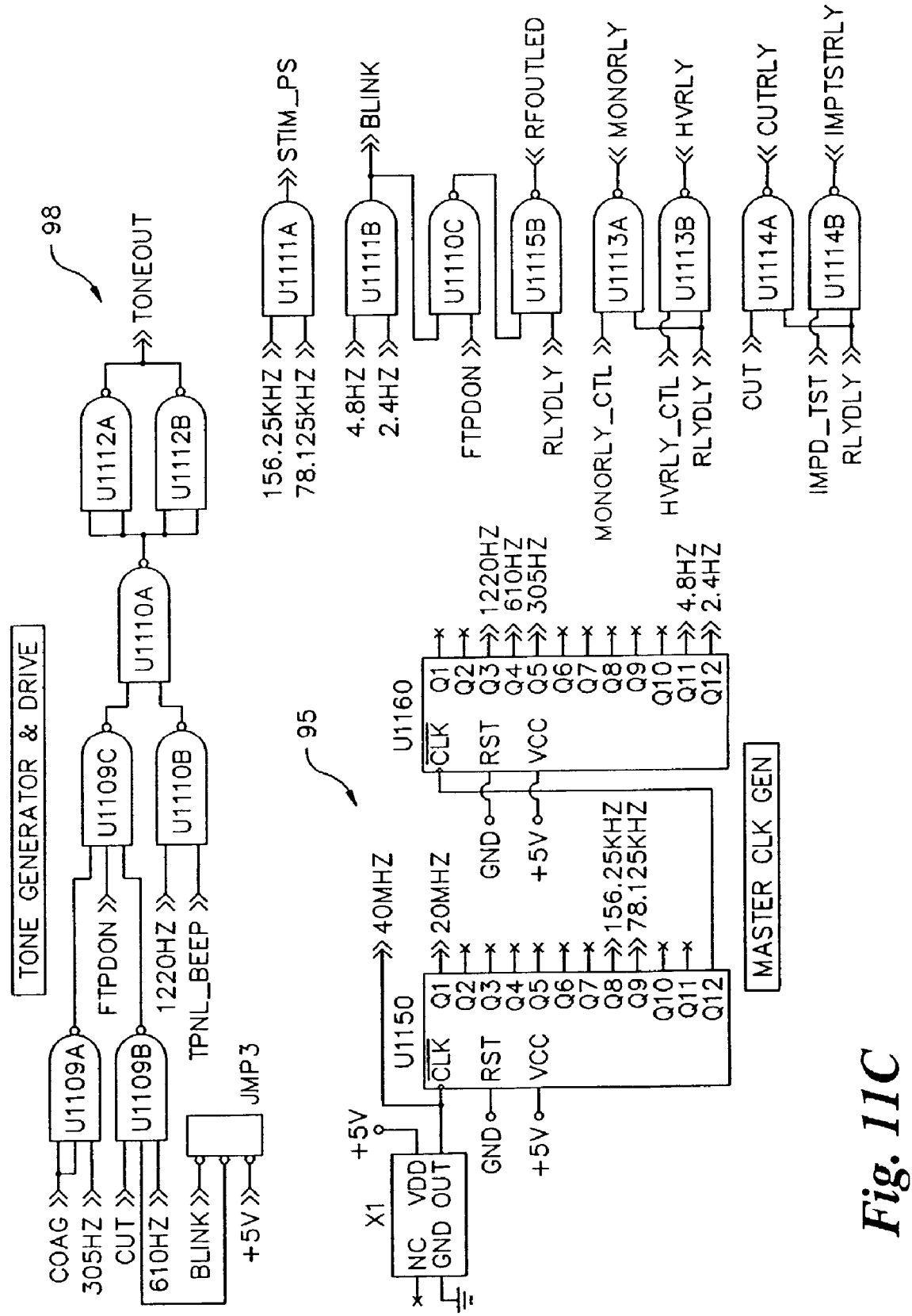

Referring to FIGS. 11A–11C, the controller board 155 includes an RF amplifier controller U1102, a digital to analog converter (DAC) IC U1107, an impedance monitor controller U1120 and a flash memory IC U1108. The flash memory IC U1108 has no moving parts and can be electrically read, erased and programmed (programmable and non-volatile) without being taken out of the circuit as is well known in the art. Preferably, the DAC IC U1107 includes at least four 8-bit channels or outputs and a 2-wire serial interface for receiving data. Other DAC ICs having different resolutions (bits of resolution) and different communications or other inputs may be provided without departing from the present invention.

The controller board 155 further includes a tone generator and drive circuit 98 and a master clock generator 95. The master clock generator circuit 95 includes an oscillator or crystal X1 and first and second multi-stage binary ripple counters U1150 and U1160. Regulated voltage, in this case (+) 5 volts DC (FIG. 8), is applied to the crystal X1 which generates a predetermined clock frequency output signal, in this case 40 MHz. The clock frequency output signal 40 MHz can be used directly by the controllers U1, U3, U1102 and U1120 and other various sub-circuits circuits throughout the control circuit 59, but the clock frequency output signal 40 MHz is also applied to a clock input of the first multi-stage binary ripple counter U1150 and one stage Q12 of the first binary ripple counter U1150 is subsequently applied to a clock input of the second multi-stage binary ripple counter U1160 to generate a plurality of frequencies which are multiples or divisions of the predetermined clock frequency output signal 40 MHz, such as 20 MHz, 156.25 KHz, 78.125 KHz, 9.766 KHz, 610 Hz, 305 Hz, 4.8 Hz and 2.4 Hz. The various clock frequencies 2.4 Hz-40 MHz are used by circuits throughout the control circuit 59 as is well known in the art.

Figure 6A:
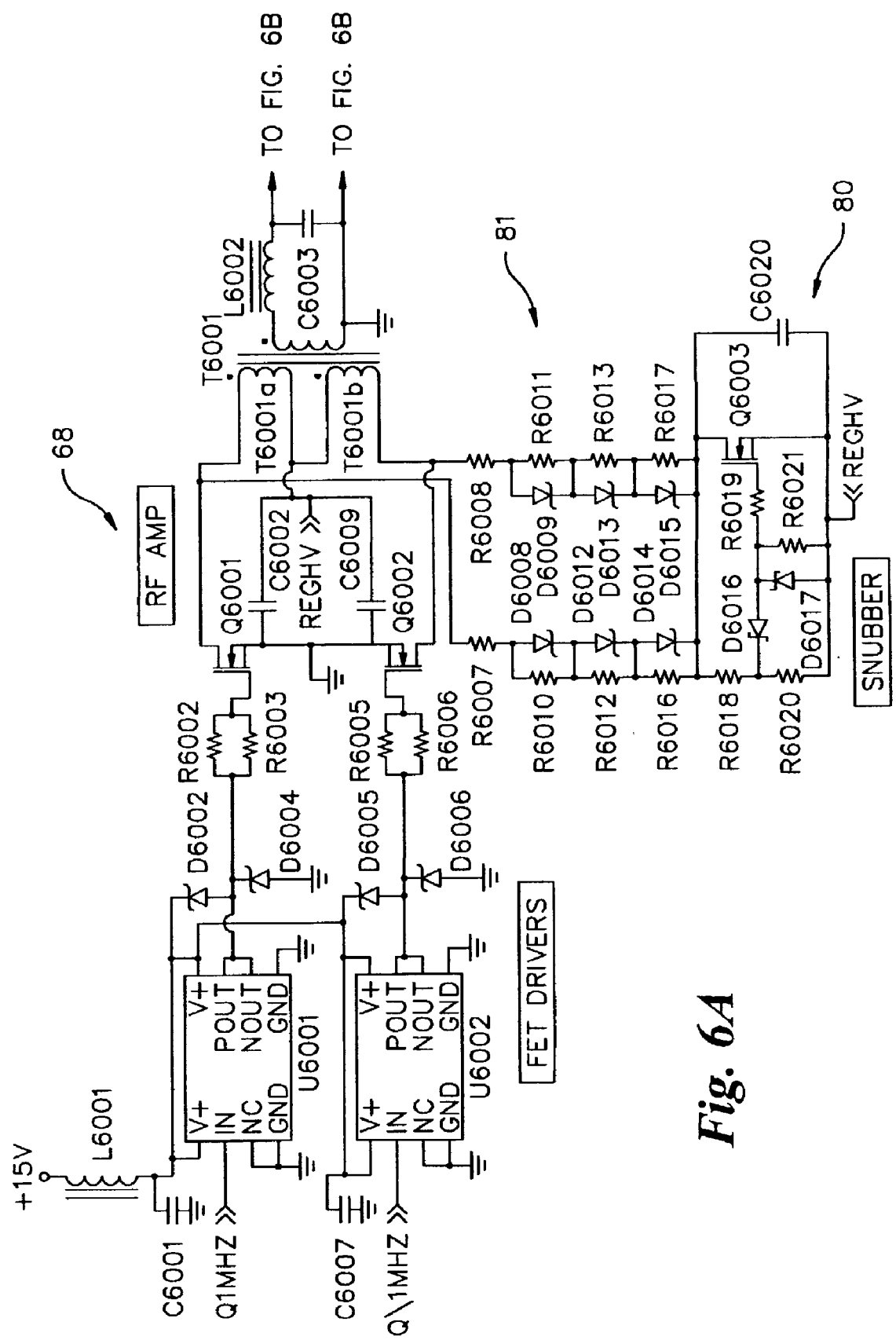
FIG. 6A–6C are circuit schematic diagrams of a radio frequency (RF) amplifier and output driver for the control circuit at FIG. 2A.
Figure 6B:
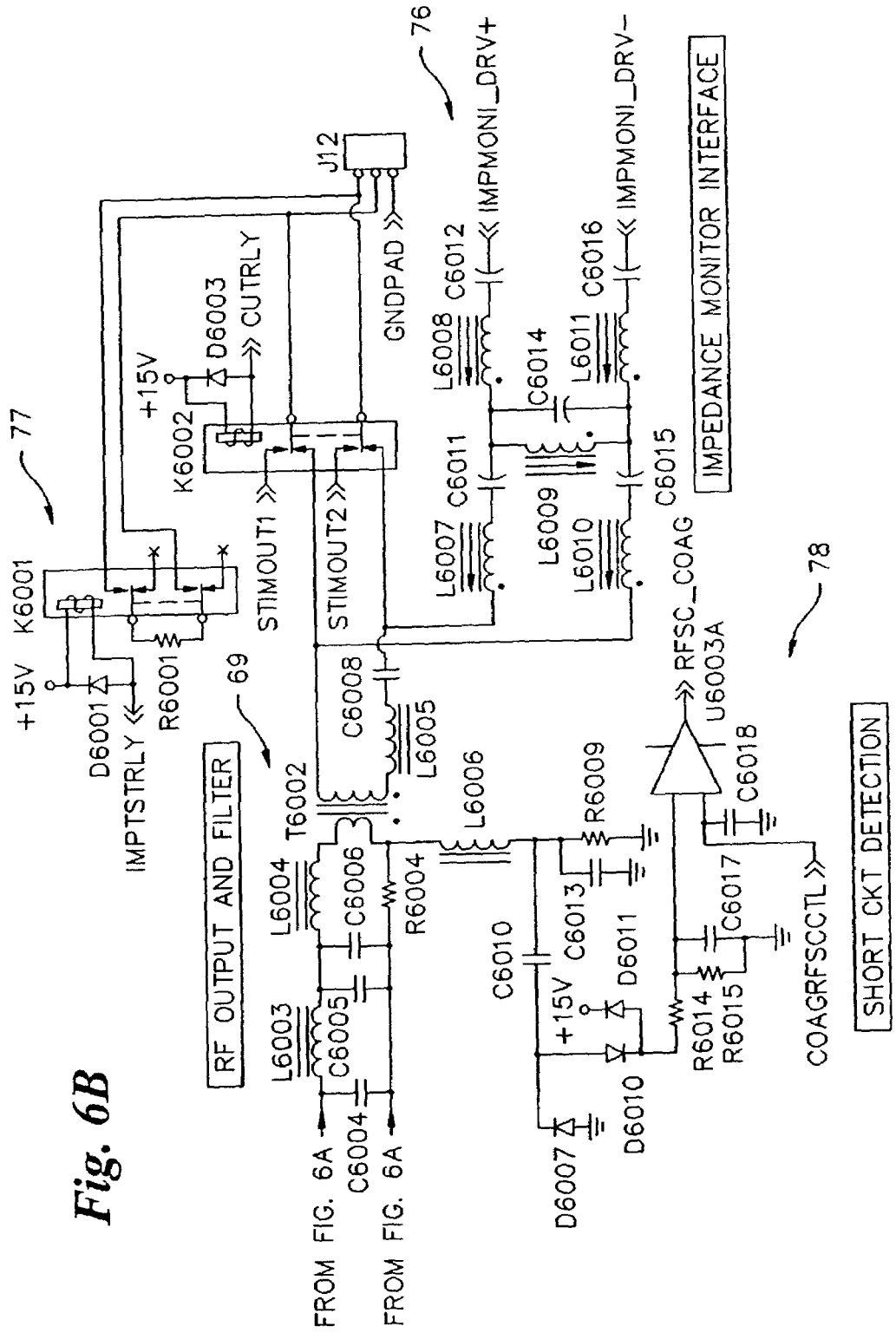
Figure 6C:
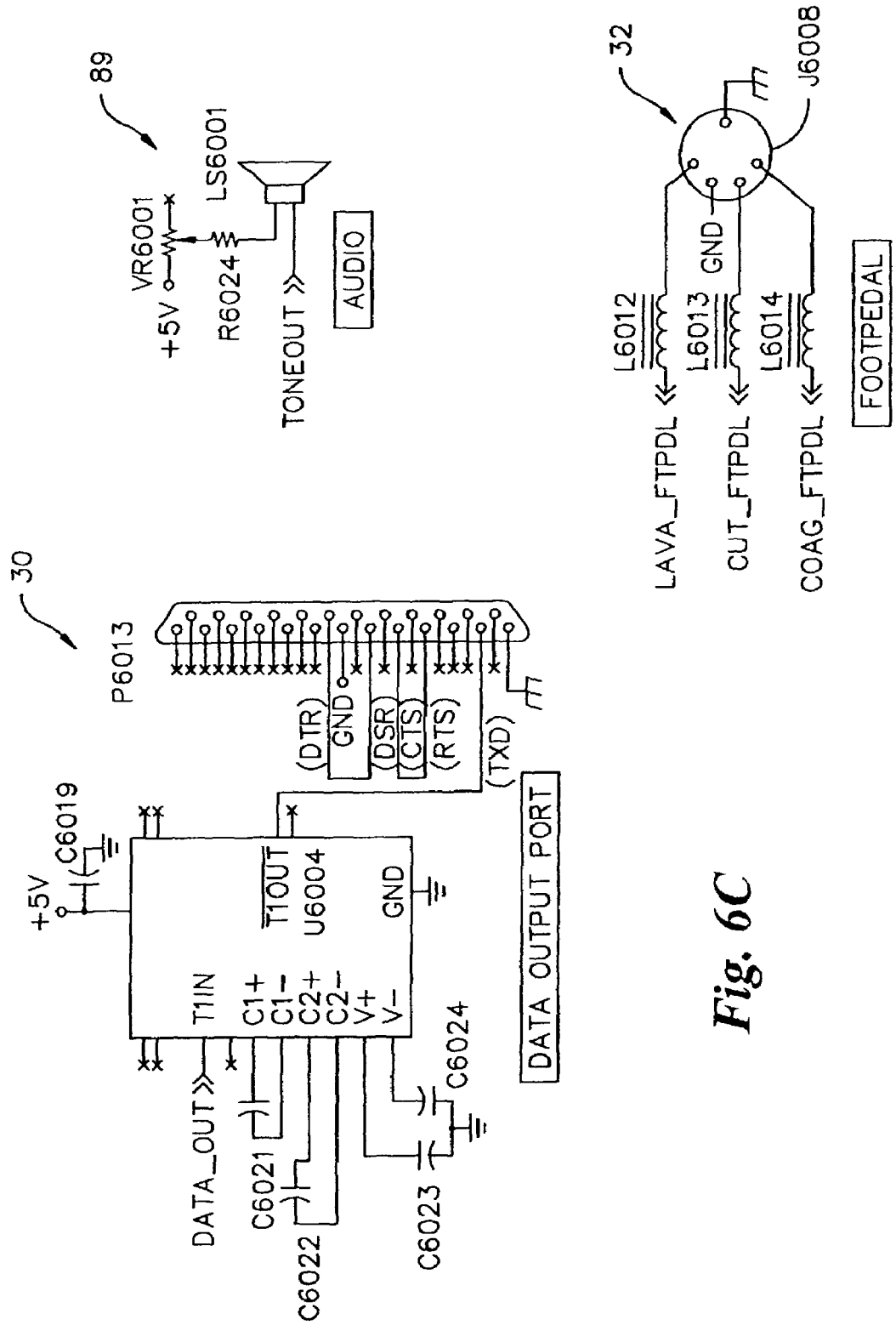

The tone generator and drive circuit 98 generates, through a series of NAND gates U1109A–U1109C, U1110A–U1110B and U1112A–U1112B, a tone out signal TONEOUT which in turn drives an audio speaker LS6001 (FIG. 6C). The tone generator and drive circuit 98 receives a coagulation mode signal COAG from the main controller U1 which is gated with the 305 Hz clock frequency and a foot pedal on signal FTPDON from the main controller U1 in order to generate a tone of a particular frequency when the coagulation mode is selected and the foot pedal is pressed. Similarly, the tone generator and drive circuit 98 receives a cut mode signal CUT from the main controller U1 which is gated with the 610 Hz clock frequency and with the foot pedal on signal FTPDON from the main controller U1 in order to generate a tone of a different frequency from the coagulation mode when the cut mode is selected and the foot pedal is pressed. This provides the user with a different audible tone when either the cut or coagulation mode is being used. Additionally, the cut mode signal CUT may be gated with a blink signal BLINK, described in greater detail hereinafter, in order to create a cyclic output to the cut mode tone for differentiating the cut mode sound from a lesion mode sound when jumper JMP3 selects the RF generator 50 to operate as a lesion/stimulate type generator instead of a cut/coagulate (normal) type generator. A touchpanel beep signal TPNL_BEEP from the main controller U1 is gated with the 1220 Hz clock frequency in order to generate yet another tone, different than the coagulation mode, the lesion mode and the cut mode tones, whenever the touchpanel 54 is touched as detected by the display controller U3. An audio circuit 89 (FIG. 6C) includes the speaker LS6001 which is connected to the tone generator output TONEOUT and to a volume adjusting potentiometer VR6001 for outputting sounds generally associated with the varying tone generator output signal TONEOUT.

Figure 8:
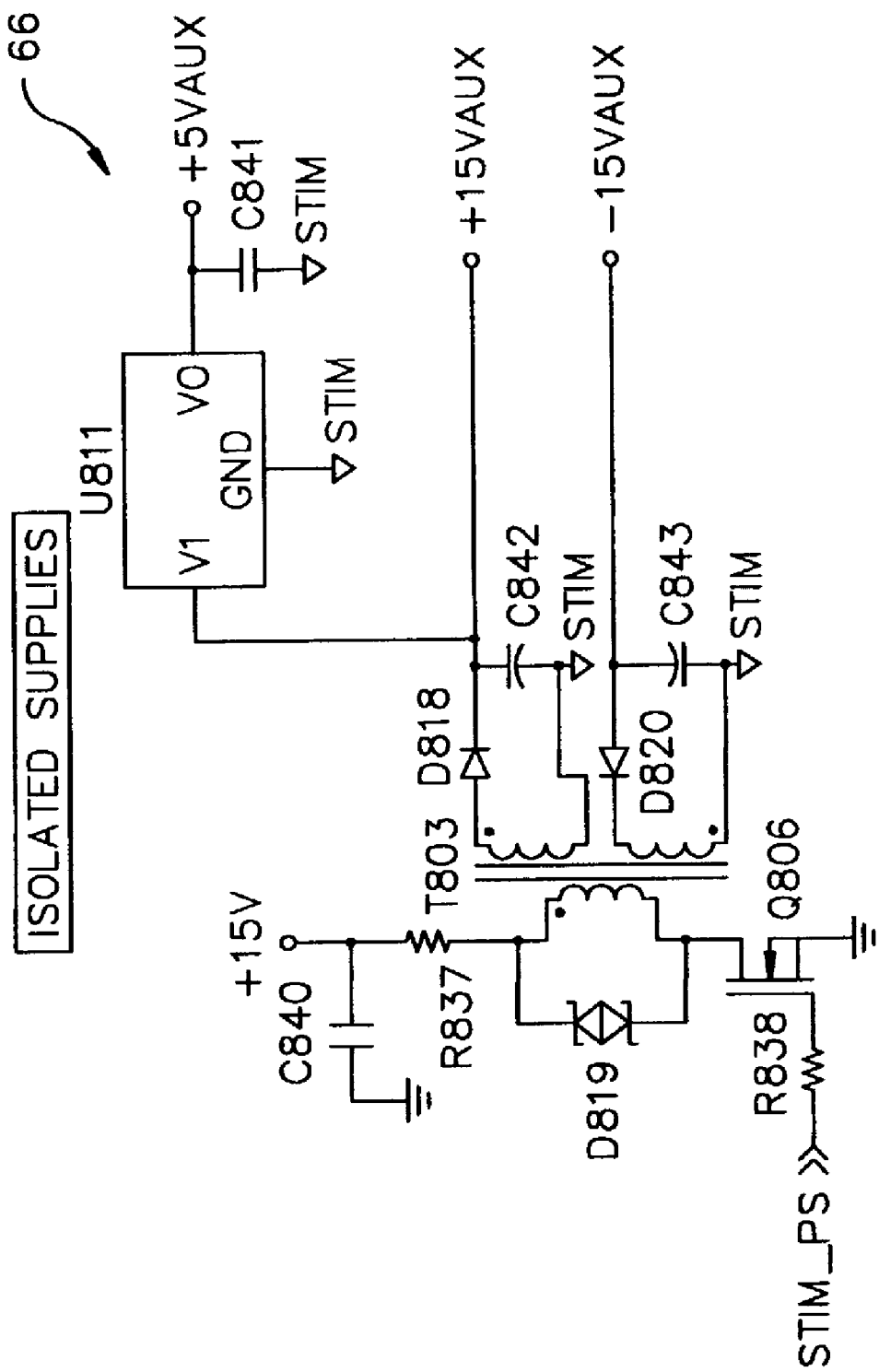
FIG. 8 is a circuit schematic diagram of isolated power supplies for the control circuit of FIG. 2A.

The controller board 155 further includes several miscellaneous gating circuits for generating other signals used throughout the control circuit 59. The 78.125 KHz and 156.25 KHz clock signals are gated by an AND gate U111A to generate a simulate pulse signal STIM_PS. The stimulate pulse signal STIM_PS is used for as an excitation or control signal for the low voltage isolated supply circuit 66 (FIG. 8). The 4.8 Hz and 2.4 Hz signals are gated by an AND gate U111B to generate the blink signal BLINK. The blink signal BLINK provides a relatively slow, cyclic pulse for use by other circuits such as indicator lights and the like. The foot pedal on signal FTPDON is gated with the blink signal BLINK by a NAND gate U1110C and subsequently gated with a relay on-delay signal RLYDLY by a NAND gate U1115B to generate an RF out flash signal RFOUTLED. The RF out flash signal RFOUTLED is used to drive first and second RF out LEDs D1, D2. A monopolar mode relay output signal MONORLY_CTL from the main controller U1 is gated with the relay on-delay signal RLYDLY by a NAND gate U1113A to generate a monopolar mode relay signal MONORLY. The monopolar mode relay signal MONORLY energizes a monomode relay K1303 (FIG. 13) when the monopolar mode is selected through the touchscreen 54 allowing a ground pad GNDPAD to be connected to the RF output of the RF generator 50. A high voltage relay output signal HVRLY_CTL of the main controller U1 is also gated with the relay on-delay signal RLYDLY by a NAND gate U1113B to generate a high voltage relay signal HVRLY. The high voltage relay signal HVRLY drives a high voltage relay K401 (FIG. 5A) in order to turn off supply power to DC level portions of the high voltage power supply 64 by the main controller U1 when a short circuit condition or other predetermined alarm condition is detected. The cut mode signal CUT from the main controller U1 is also gated with the relay on-delay signal RLYDLY by a NAND gate U1114A to generate a cut relay signal CUTRLY. The cut relay signal CUTRLY controls an output mode relay K6002 (FIG. 6B) to switch between output voltage levels as described in greater detail hereinafter. An impedance test output signal IMP-D_TST from the main controller U1 is also gated with the relay on-delay signal RLYDLY by a NAND gate U1114B to generate an impedance test relay signal IMPTSTRLY. The impedance test relay signal IMPTSTRLY controls an impedance test relay K6001 (FIG. 6B).

Figure 12A:
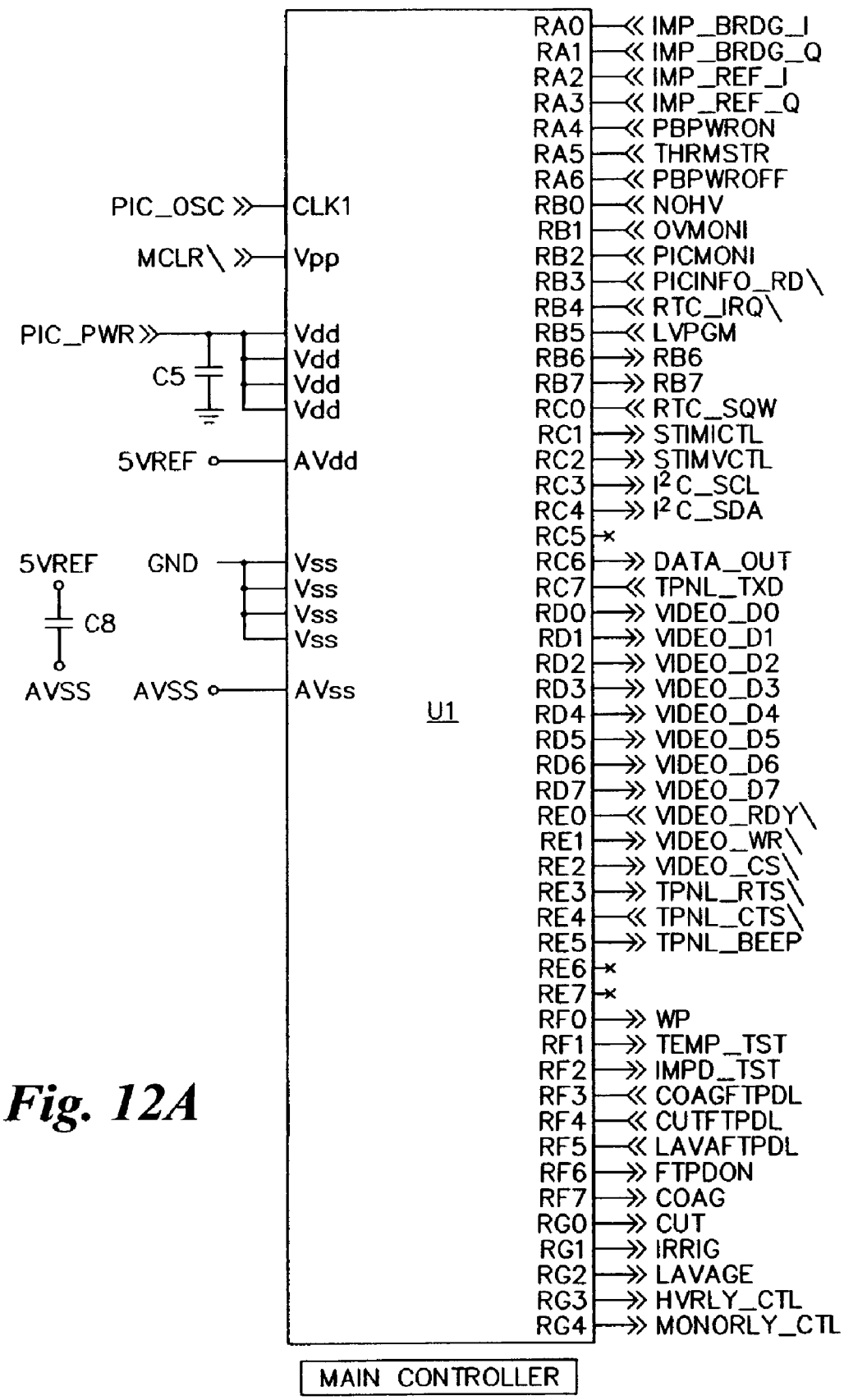
FIG. 12A–12-B are a circuit schematic diagrams of a main controller and various sub-controllers for the control circuit of FIG. 2A.
Figure 12B:
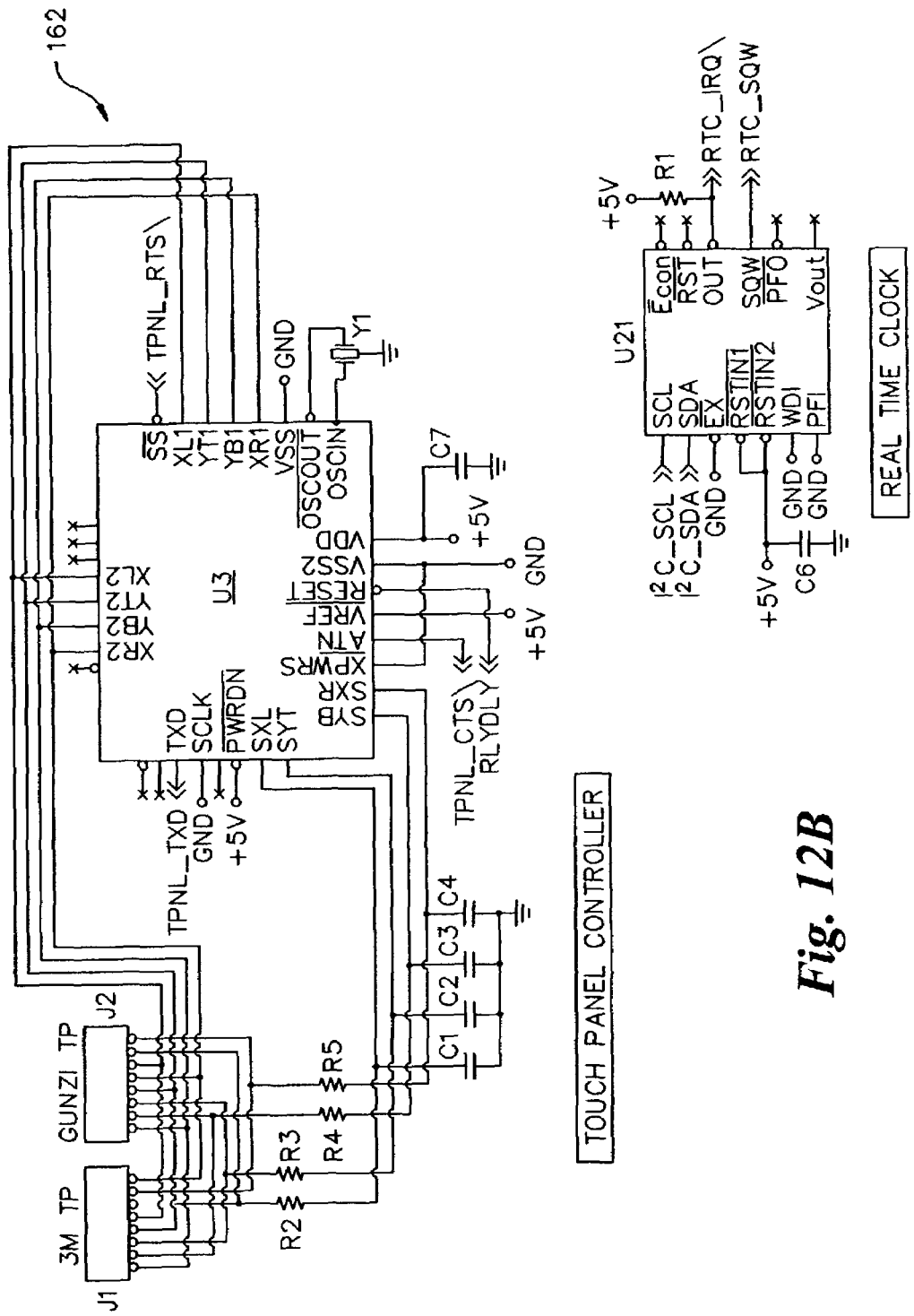

Referring to FIGS. 12A–12B, the SMT controller board 162 (FIG. 2B) includes the main controller U1, a real time clock U21, and a display controller U3. Preferably, the real time clock U11021 is used in conjunction with a battery back-up system (not shown). Preferably, the main controller U1 is a complementary metal oxide semiconductor (CMOS) FLASH-based 8-bit microcontroller with 100 nanosecond instruction execution and includes about 1024 bytes of electrically erasable programmable read only memory (EE-PROM), about 12 channels of 10-bit Analog-to-Digital (A/D) converter, an additional timer, external memory addressing, about two built-in comparators, a synchronous serial port which can be configured as either 3-wire serial peripheral Interface (SPI) or as 2-wire Inter-Integrated Circuit (I²C®) bus (a registered trademark of Philips Electronics, Eindhoven, NETHERLANDS) and about two addressable universal asynchronous receiver transmitters (AUSARTs). The main controller U1 could be other microcontrollers having other sizes and speeds, or the main controller U1 could be an application specific integrated circuit (ASIC), a programmable logic array (PLA), a microprocessor and the like without departing from the present invention. The main controller U1 acts as a master controller to the other controllers U3, U1102 and U1120. At least the main controller U1 uses at least the flash memory IC U1108 to store and/or retrieve data, but the controllers U3, U1102 and U1120 may also use the flash memory IC U1108 to store and/or retrieve data. An I²C bus provides two-wire serial communication between controllers U1, U1102 and U1120, the DAC IC U1107, the real time clock U11021 and the flash memory IC U1108. The I²C bus is bi-directional and uses a serial data (SDA) line and a serial clock (SCL) line along with dedicated ports on a given controller for digital communication. The controllers U1, U1102 and U1120, the DAC IC U1107, the real time clock U11021 and the flash memory IC U1108 each have a unique address for I²C communications. Other inter-controller communication such as straight I/O or other serial or parallel communications protocols may be used without departing from the present invention. Preferably, the main controller U1 also provides a separate write protect signal WP to the flash memory IC U1108, in addition to the I²C bus communications, in order to issue write protect commands directly to the flash memory IC U1108. Preferably, the main controller U1 also receives a real time clock interrupt signal RTC_IRQ\ and a real time clock sequential write signal RTC_SQW, in addition to the I²C bus communications, in order to interrupt the main controller U1 for more precise real time updates.

The main controller U1 communicates with the display controller U3 serially via touchpanel ready to send TPNL_RTS, touchpanel clear to send TPNL_CTS, and touch panel transmit TPNL_TXD signals. The main controller U1 also provides data to the touchpanel 54 through the display control circuit 60 via video data signals VIDEO_D0–VIDEO_D7 and communicates directly with the display control circuit 60 via communications signals including video clear to send VIDEO_CS\, video ready VIDEO_RDY\ and video write VIDEO_WR. The display control circuit 60 allows the main controller U1 to display data such as current timer\counter\setpoint presets, measured process values and the like. The display controller U3 detects actual presses of the touchpanel 54 at specific locations and times in order to determine what feature or button a user has selected or entered on a particular screen (FIGS. 15A–15H).

Referring to FIG. 12B, the SMT controller board 162 further includes filtering capacitors C1–C4, a sense X-left resistor R2, a sense Y-top resistor R3, a sense Y-bottom resistor R4, a sense X-right resistor R5, a biasing capacitor C7, and an external crystal or oscillator Y1, which together support the display controller U3. The touchscreen 54 communicates with at least the main controller U1 through display controller U3 in order to display data from the memory and to allow a user to enter settings. The sense resistors R2–R5 connect to touch panel cables 3M TP, GUNZI TP and provide voltage inputs to the display controller U3 at inputs SXL, SYT, SYB, and SXR, respectively.

Figure 18A:
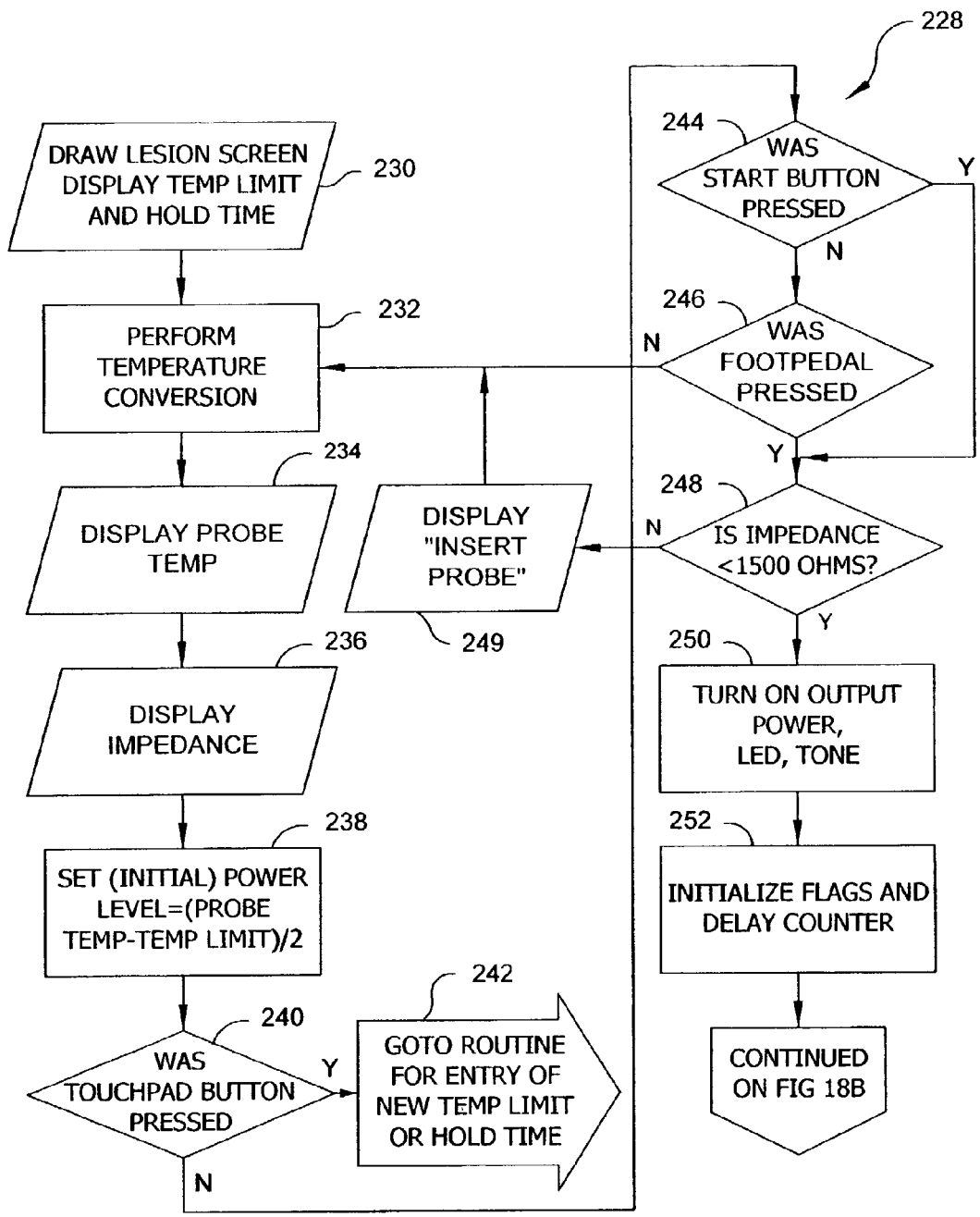
Figure 19A:
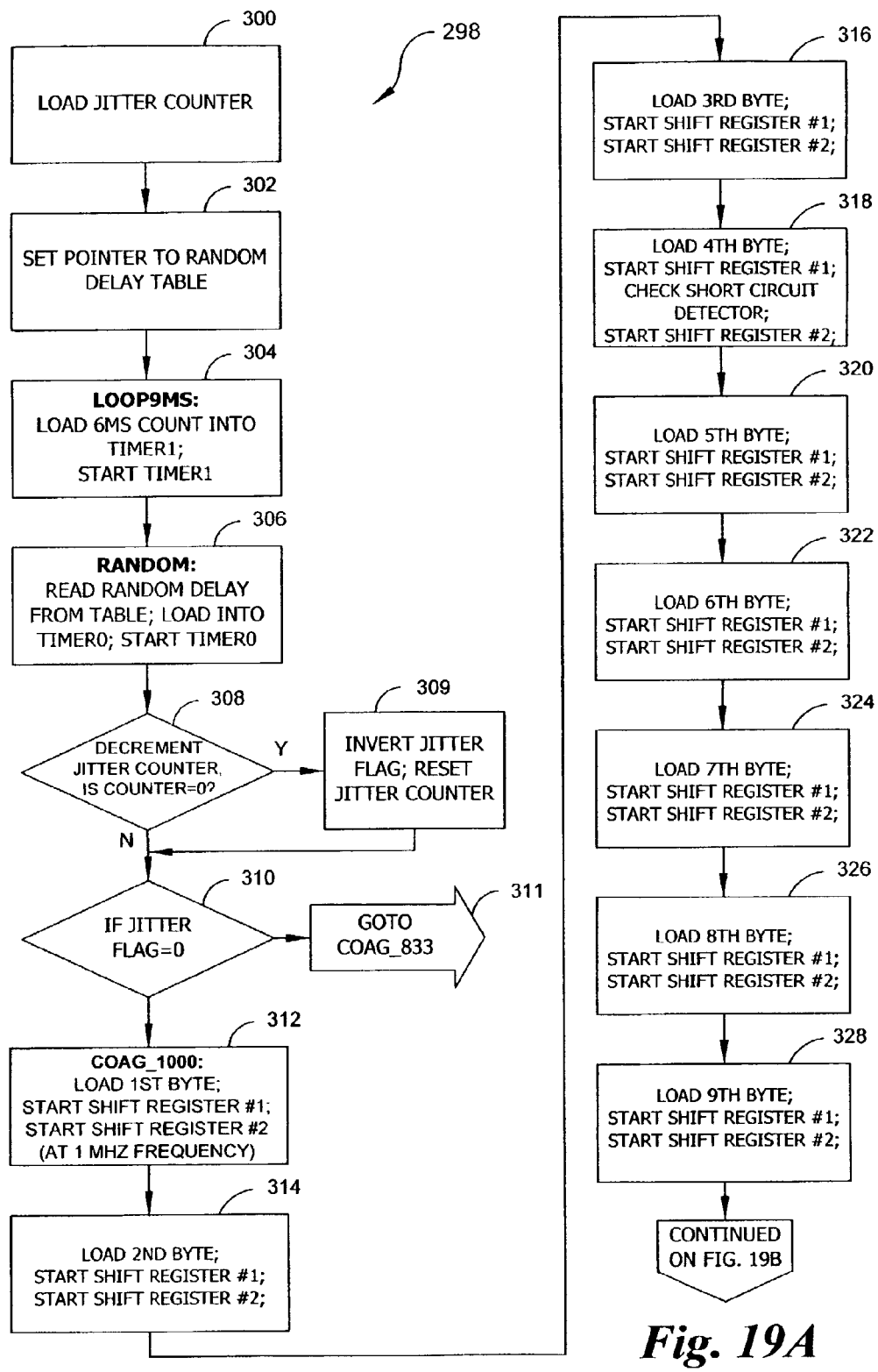
FIGS. 19A–19C are flow charts depicting a synopsis of the software operation for RF output control for the control circuit of FIG. 2A.
Figure 19B:
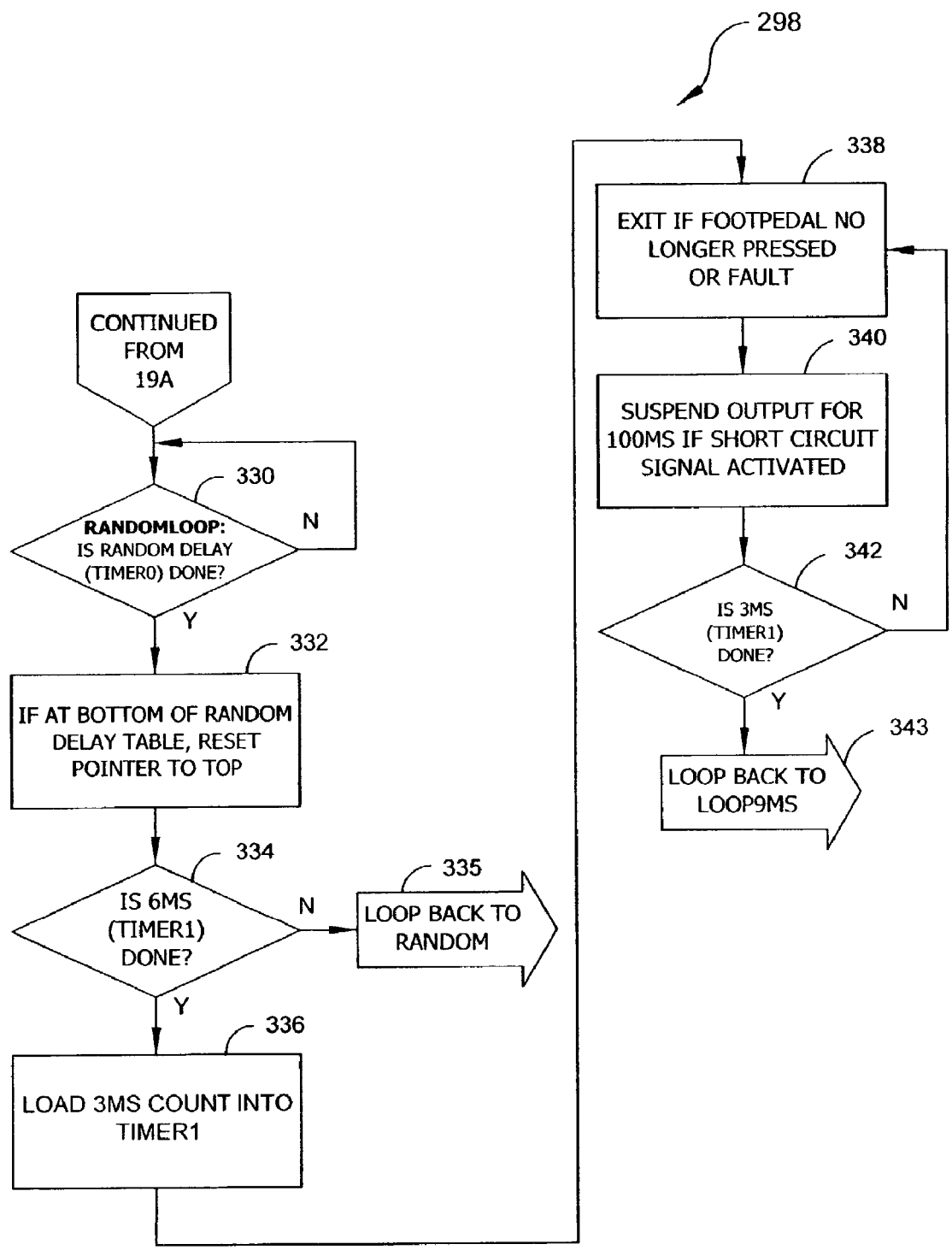
Figure 19C:
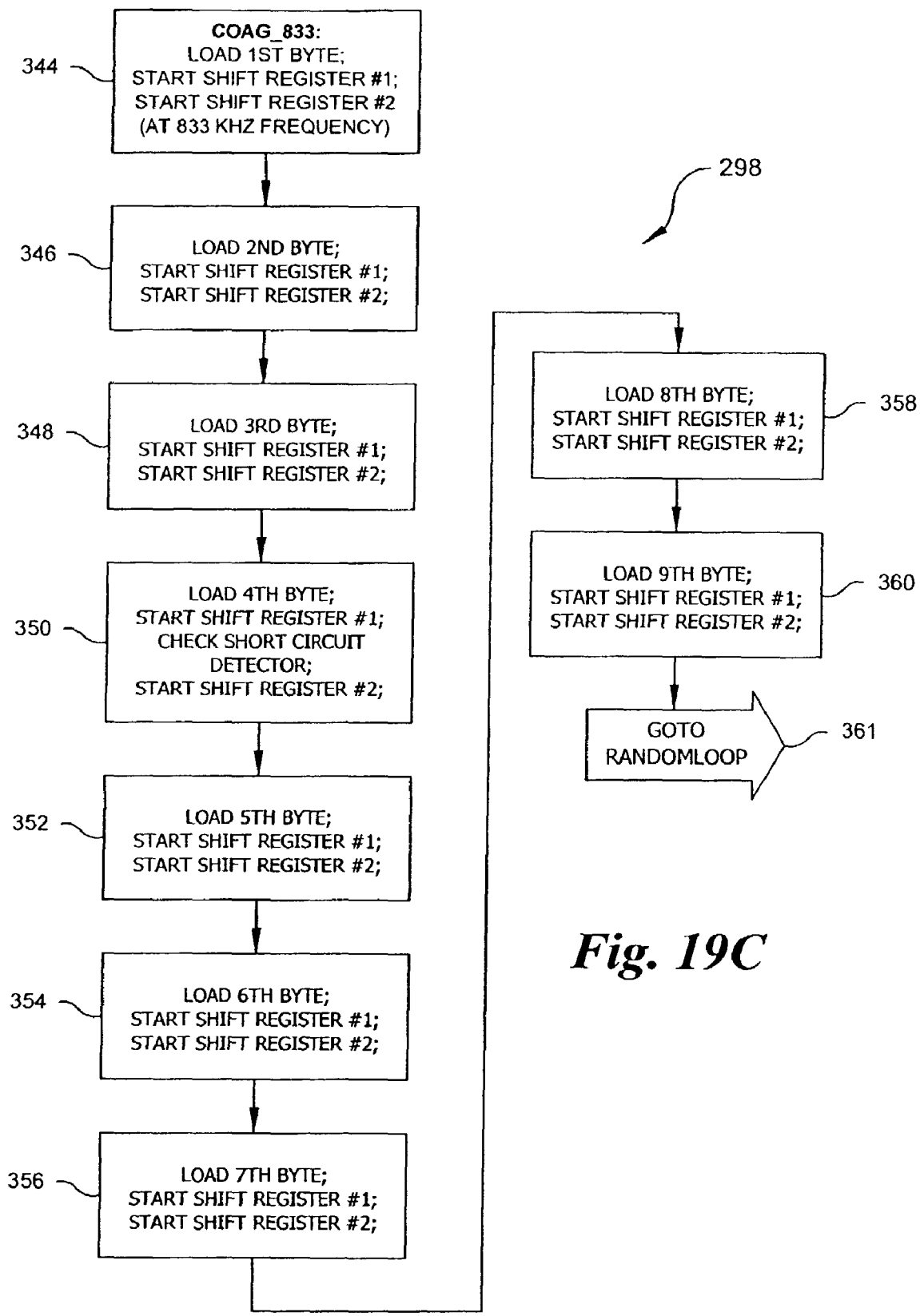

Referring to FIG. 1A, the RF amplifier controller U1102 drives a pair of shift registers U1130, U1140 to generate declining pulse duration modulated (PDM) RF outputs. Preferably, the shift registers U1130, U1140 generate about one MHz declining PDM RF outputs. Preferably, the shift registers U1130, U1140 are 8-bit shift registers. It is to be understood by those skilled in the art that a 16-bit shift register or other sized shift registers could be used without departing from the scope and spirit of the present invention. The shift registers U1130, U1140 provide a series of output pulses at about a 0.5 microsecond rate and/or multiples and derivatives thereof. The RF amplifier controller U1102 shifts the input load (data lines B0–B7) of the shift registers U1130, U1140 to produce pulses which are out of phase from one another at a given rate, in this case at about a 1 MHz rate or an 833 MHz rate as described hereinafter (FIGS. 18A–18C). Preferably, the RF amplifier controller U1102, in combination with a 20 MHz clock signal from the master clock generator 95, causes the shift registers U1130, U1140 to have the following pulse waveform pattern: about 2 microseconds on, about 0.5 microseconds off, about 1.5 microseconds on, about 1 microsecond off; about 1 microsecond on, about 1.5 microseconds off; about 0.5 microseconds on, about 2 microseconds off. Preferably, the total duration for the entire waveform is about 10 microseconds. The resulting waveform is a decaying square wave which is filtered to form a decaying sine wave as described hereafter. Of course other signals and waveforms may be created without departing from the present invention, for example providing equal on and off times result in a pulse train of square waves. The shift registers U1130, U1140, in turn, drive a pair of field effect transistor (FET) drivers U6001, U6002 in the RF amplifier circuit 68 shown on FIG. 6A with their respective shift register outputs Q1MHZ and Q\1MHZ. The first and second shift register outputs Q1MHZ and Q\1MHZ are also inputs back into the RF amplifier controller U1102. Generally, the first shift register output Q1MHZ is about 180° out of phase with the second shift register output Q\1MHZ. Preferably, the RF amplifier controller U1102 which is controlled by the main controller U1 includes an controlling program that generates a plurality of different user selectable waveforms based on PDM modulation of the carrier signal (FIGS. 19A–19C).

Referring to FIGS. 6A–6C, the RF amplifier circuit 68 is substantially disposed on the main board 159. The RF amplifier circuit 68 includes Zener diodes D6002, D6004–D6006, D6008–D6009 and D6012–D6015, diodes D6016–D6017, diodes D6001 and D6007, and D6010–D6011, transformer T6001, capacitors C6001–C6002, FET drivers U6001 and U6002, and field effect transistors (FETs) Q6001 and Q6002. The FETs Q6001, Q6002 in combination with the FET drivers U6001, U6002 and the three winding transformer T6001 form the amplifier portion of the RF amplifier circuit 68. The RF amplifier circuit 68 amplifies the output signals Q1MHZ, Q\1MHZ from the shift registers U1130, U1140. The output signals Q1MHZ, Q\1 MHZ from the shift registers U1130, U1140 drive the FET drivers U6001 and U6002 which in turn drive the FETs Q6001, Q6002. Preferably, the FETs Q6001, Q6002 are fast switching metal oxide semiconductor FETs (MOSFETs) with about 500 V breakdown voltages and current ratings of about 15 A. The FETs Q6001, Q6002 switch a regulated high voltage REG HV (FIG. 5B) to first and second primary windings T6001a, T6001b, respectively of the transformer T6001.

The RF amplifier circuit 68 further includes a snubber portion 80 connected to the primary windings T6001a, T6001b of the amplifier transformer T6001 via a resistor and Zener diode bridge 81 which includes an FET Q6003 and diodes D6016, D6017. The snubber portion 80 prevents or reduces high inductive spiking of voltages and controls switching voltage transients, as is well known in the art.

The RF amplifier circuit 68 further includes inductors L6002–L6006 in combination with an isolation transformer T6002 which form the RF output and filter 69 of the RF amplifier 68. The RF output and filter 69 filters the waveforms from the FETs Q6001 and Q6002 in order to achieve waveforms closer to or approximating sinusoidal and also provides signal isolation in order to reduce RF leakage. Preferably, the isolation transformer T6002 is a toroid-type transformer. The overall impedance on the secondary side of the isolation transformer T6002 is a function of the secondary winding of transformer T6002, inductor L6005 and capacitor C6008, and is selected or modified by changing component values in order to configure the RF amplifier circuit 69 for cut mode or coagulate mode. As mentioned above, the impedance of the output of the RF amplifier is preferably about 400 ohms for cut mode and about 20 ohms or less for coagulate mode. While only one RF output and filter circuit 69 is shown in FIG. 6B, it is also possible to have two RF output and filter circuits 69 which are selectively switched by a cut/coagulate relay (not shown) in order to provide a cut mode and coagulate mode output in a single RF generator 50. The RF amplifier 68 shown in FIGS. 6A–6B is simplified for use as a lesion generator so that the impedance of the output of the RF amplifier could be chosen to be a cut mode or a coagulate mode in order to generate lesions. Since the output waveform is controlled by the RF amplifier controller U1102 (i.e., via software) either type of output signal, decaying or continuous, can be selected.

The RF amplifier circuit 68 further includes a short circuit detection circuit 78 which is connected to the RF output and filter 69 by inductor L6006. The short circuit detection circuit 78 generally determines when the output current exceeds a predetermined threshold current as set by the main controller U1. The short circuit detection circuit 78 includes operational amplifier (op-amp) U6003A, diodes D6007, D6010–D6011, capacitors C6010, C6013, C6017–C6018 and resistors R6009, R6014. The threshold of the short circuit detection circuit 78 is controlled by the main controller U1 by analog output signals from the DAC IC U1107 which is controlled via the I²C bus. The DAC IC U1107 generates an RF short circuit control signal CAOGRFSC-CTL which corresponds to the predetermined threshold current in the main controller U1 and which is applied to the positive input of op-amp U6003A wherein op-amp U6003A is applied as a comparator. Current in the RF output and filter 69 is detected through inductor L6006 and the resistor R6009 and capacitors C6013 and C6010 filter or smooth the detected signal. Diodes D6010, D6011 allow a reduced voltage, in this case +15V, to be piloted by the detected current thereby applying an equivalent level current at a lower voltage through resistor R6015 and a corresponding voltage is then applied to the negative input of comparator U6003A. The output of comparator U6003A is an RF short circuit signal RFSC_COAG which, if present, is supplied to an input of the RF amplifier controller U1102. If the RF amplifier controller U1102 receives the RF short circuit signal RFSC_COAG for a predetermined period of time, the RF amplifier controller U1102 will shut-off outputs to the RF amplifier circuit 68 and high voltage power supply circuit 64 and send a signal to the main controller U1 for alarming and the like.

Figure 13:
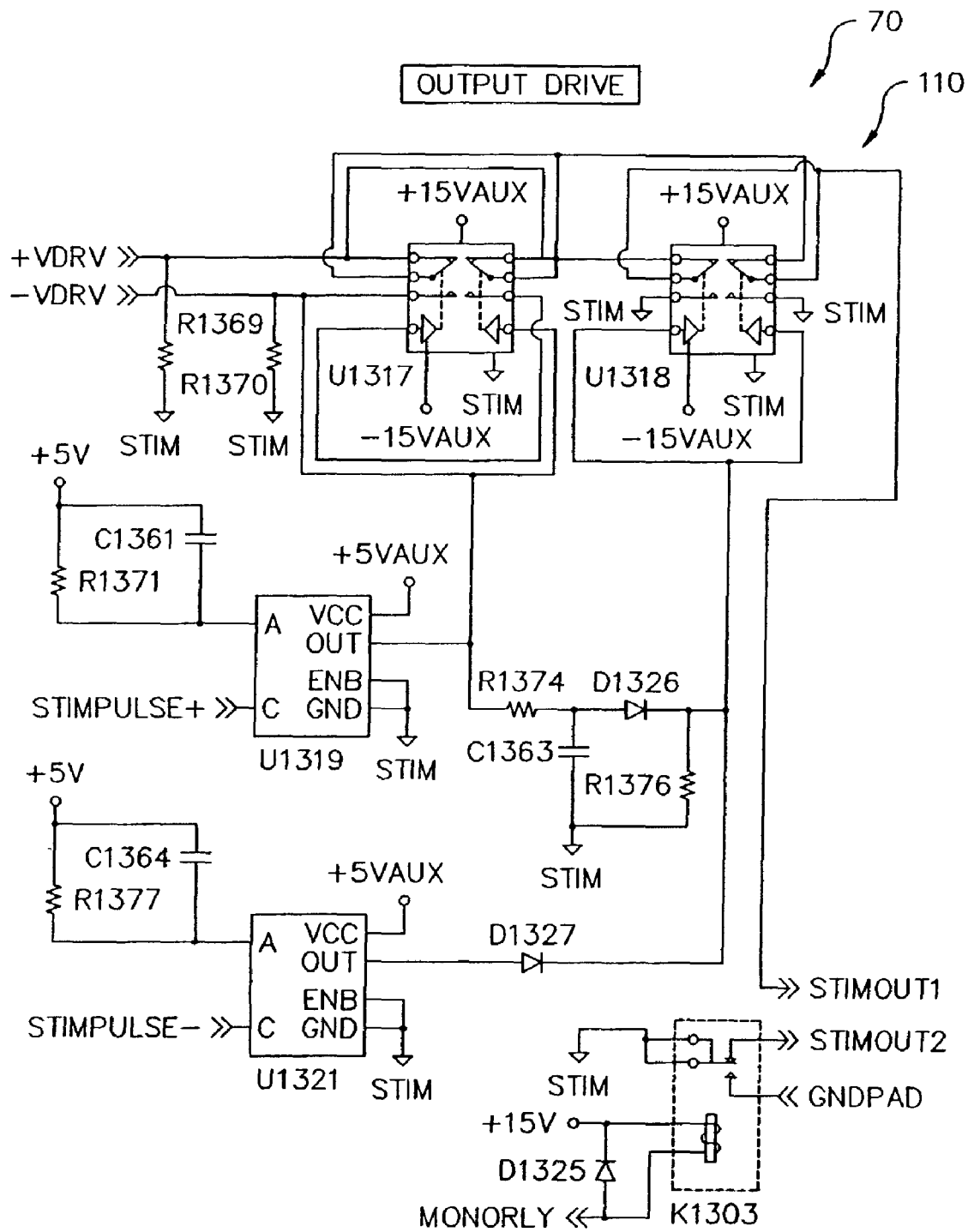
FIG. 13 is a circuit schematic diagram of an output drive circuit for the control circuit of FIG. 2A.

FIG. 6B shows that the output mode relay K6002 selects between the output of RF output and filter 69 of the RF amplifier circuit 68 and a stimulation signal which includes stimulate signals STIMOUT1, STIMOUT2 (FIG. 13). The coil of the output mode relay K6002 is controlled by the cut relay signal CUTRLY derived from NAND gates U1114A, U1114B and the cut output signal CUT from the main controller U1.

The impedance monitor interface 76 is connected in parallel with the RF output and filter 69 of the RF amplifier circuit 68. The impedance monitor interface 76 includes inductors L6007–L6011 and capacitors C6011–C6012 and C6014–C6016 which form a diplexer for filtering out a particular signal between two mixed signals as described in greater below.

The controller board 155 (FIG. 2B) further includes the impedance monitor controller U1120 (FIG. 11B) which is coupled to the impedance monitor interface 76 (FIG. 6B). The impedance monitor controller U1120 is a separate microcontroller which communicates with the main controller U1 via the I²C bus as mentioned above. The impedance monitor interface 76 is in electrical communication with an impedance monitor circuit 90 (FIGS. 4A–4D). The impedance monitor circuit 90 includes a reflectometer bridge 92, a bridge signal conditioner 94 and four detector circuits, namely a quadrature bridge or Q-bridge detector 100, an in-phase bridge or I-bridge detector 102, an quadrature reference or Q-reference detector 104, and an in-phase reference or I-reference 106. A sine reference signal 20KHZ_REF from a reference signal generator 108 (FIG. 14) is applied to the reflectometer bridge 92. The sine reference signal 20KHZ_REF is about 18 to 24 kHz, but preferably, the sine reference signal 20KHZ_REF is about 20 kHz. The sine reference signal 20KHZ_REF provides an excitation signal, i.e., impedance monitor drive signals IMPMONI_DRV+, IMPMONI_DRV−, for measuring impedance over the electrodes 44a, 44b of the bipolar surgical pen 40. The impedance monitor drive signals IMPMONI_DRV+, IMPMONI_DRV− are applied to the bipolar surgical pen 40 through the impedance monitor interface 76 (FIG. 6B) thereby superimposing the impedance monitor drive signals IMPMONI_DRV+, IMPMONI_DRV− onto a given cut/coagulate signal (i.e., the output of RF output and filter 69). The impedance monitor interface 76 functions as a filter-type diplexer which selectively removes an impedance signal to be measured from the cut or coagulation signal from the RF output circuit 69. Of course other signal separation circuits may be implemented without departing from the present invention. The impedance monitor drive signals IMPMONI_DRV+, IMPMONI_DRV− therefore, the impedance affects the conditioned form of the sine reference signal 20KHZ_REF which is applied to the bridge detectors 100, 102 through the bridge signal conditioning circuit 94.

When the impedance test relay K6001 (FIG. 6B) is energized by the impedance test relay signal IMPTSTRLY, resistor R6001 simulates a fixed value on the impedance monitor drive/feedback signals IMPMONI_DRV+, IMPMONI_DRV−. Preferably, resistor R6001 is a precision resistor with a tolerance of about 1% or better. Of course, resistor R6001 could be selected with other tolerances and other resistance values without departing from the present invention. It is contemplated that resistor R6001 is a variable resistance device such as a multi-resistor switch-selectable block for generating user selectable voltages when testing the overall RF generator 50.

The Q-bridge detector 100 includes transconductance op-amps U4023 and U4024, op-amp U4025, resistors R4032, R4034, R4036, R4038, R4040, R4042, R4043, R4046–R4048 and R4050, capacitors C4043 and C4045, and diodes D4060 and D4070. Impedance monitor feedback signals IMPMONI_DRV+, IMPMONI_DRV− conditioned via the bridge conditioning circuit 94 are applied to transconductance op-amps U4023 and U4024 of the Q-bridge detector 100. The Transconductance op-amp U4023 also receives a 180° signal 180DEG from a four phase reference generator 108 (FIG. 14) so that the output of the transconductance op-amp U4023 is only permitted when the 180° signal 180DEG is on. Similarly, the transconductance op-amp U4024 also receives a 0° signal 0DEG from the four phase generator 108 so that the output of the transconductance op-amp U4024 is only permitted when the 0° signal 0DEG is on. The outputs of transconductance op-amps U4023, U4024 are alternately, based on phase angle signals 0° signal 0DEG and 180° signal 180DEG, input to op-amp U4025 and subsequently to a low pass filter comprising the resistor R4036 and capacitor C4043 which together form a bridge Q-channel synchronous demodulator 101. The bridge Q-channel synchronous demodulator 101 outputs a Q-channel bridge signal IMP_BRDG_Q to the main controller U1 and the impedance monitor controller U1120. The Q-bridge signal IMP_BRDG_Q generally corresponds to the overall imaginary component of the impedance at the electrodes 44a, 44b.

The I-bridge detector 102 includes transconductance op-amps U4026 and U4027, op-amp U4028, resistors R4033, R4035, R4037, R4039, R4041, R4044–R4045, R4049, R4071, R4072, and R4083, capacitors C4044 and C4046, and diodes D4008 and D4009. Impedance monitor feedback signals IMPMONI_DRV+, IMPMONI_DRV− conditioned via the bridge signal conditioner 94 are also applied to transconductance op-amps U4026, U4027. The Transconductance op-amp U4026 also receives a 90° signal 90DEG from the four phase reference generator 108 so that the output of the transconductance op-amp U4026 is only permitted when the 90° signal 90DEG is on. Similarly, the transconductance op-amp U4027 also receives a 270° signal 270DEG from the four phase generator so that the output of the transconductance op-amp U4027 is only permitted when the 270° signal 270DEG is on. The output of transconductance op-amps U4026, U4027 are alternately, based on phase angle signals for 90° signal 90DEG and 270° signal 270DEG, input to the op-amp U4028. The output of op-amp U4028 is applied to a low pass filter that includes resistor R4037 and capacitor C4044. The op-amp U4028 and the low pass filter form a bridge I-channel synchronous demodulator 103. The bridge I-channel synchronous demodulator 103 outputs an I-channel bridge signal IMP_BRDG_I to the main controller U1 and the impedance monitor controller U1120. The I-bridge signal IMP_BRDG_I generally corresponds to the overall real component of the impedance at the electrodes 44a, 44b.

The Q-reference detector 104 includes transconductance op-amps U4031 and U4032, op-amp U4033, resistors R4057, R4059, R4061, R4063, R4065, R4067–R4068, R4073, R4079, R4080 and R4081, capacitors C4047 and C4049, and diodes D4010 and D4011. The sine reference signal 20KHZ_REF is also dropped across a resistor R4030 to create an alternate sine reference signal 20KHZ_REF_A. The alternate sine reference signal 20KHZ_REF_A is applied to reference signal conditioner 96. The reference signal conditioner 96 comprises op-amps U4029, U4030 and resistors R4051, R4055–R4056. The conditioned signal output from the reference signal conditioner 96 is applied to the transconductance op-amps U4031, U4032. The transconductance op-amp U4031 also receives the 180° signal 180DEG from the four phase reference generator 108 so that the output of the transconductance op-amp U4031 is only permitted when the 180° signal 180DEG is on. Similarly, the transconductance op-amp U4032 also receives the 0° signal 0DEG from the four phase generator 108 so that the output of the transconductance op-amp U4032 is only permitted when the 0° signal 0DEG is on. The outputs of the transconductance op-amps U4031, U4032 are alternately, based on phase angle signals 0° signal 0DEG and 180° signal 180DEG, input to the op-amp U4033 and a low pass filter including resistor R4061 and capacitor C4047 which form a reference Q-channel synchronous demodulator 105. The reference Q-channel synchronous demodulator 105 outputs a Q-channel reference signal IMP_REF_Q to the main controller U1 and the impedance monitor controller U4020. The Q-channel reference signal IMP_REF_Q generally corresponds to the imaginary component of the reference signal which is used to compensate out the impedance of the electrodes 44a, 44b themselves from the overall imaginary component of the measured impedance.

The reference signal conditioner 96 also provides an input to the I-reference detector 106. The I-reference detector 106 includes transconductance op-amps U4034 and U4035, op-amp U4036, resistors R4058, R4060, R4062, R4064, R4066, R4069, R4070, R4074, R4082 and R4084–R4085, capacitors C4048 and C4050, and diodes D4012 and D4013. The output of the reference signal 96 is applied to the inputs of transconductance op-amps U4034, U4035. The transconductance op-amp U4034 also receives the 90° signal 90DEG from the four phase reference generator 108 so that the output of the transconductance op-amp U4034 is only permitted when the 90° signal 90DEG is on. Similarly, the transconductance op-amp U4035 also receives the 270° signal 270DEG from the four phase generator 108 so that the output of the transconductance op-amp U4035 is only permitted when the 270° signal 270DEG is on. The outputs of the transconductance op-amps U4034, U4035 are alternately, based on phase angle signals for 90° signal 90DEG and 270° signal 270DEG, input to the op-amp U4036. The output of the op-amp U4036 is passed through a low pass filter including resistor R4062 and capacitor C4048 which together form a reference I-channel synchronous demodulator 107. The reference I-channel synchronous demodulator 107 outputs an I-channel reference signal IMP_REF_I to the main controller U1 and the impedance monitor controller U1120. The I-channel reference signal IMP_REF_I generally corresponds to the real component of the reference signal which is used to compensate out the actual impedance of the electrodes 44a, 44b themselves from the overall real component of the measured impedance.

The combination of the synchronous detectors 100, 102, 104, 106 is used to detect the angle and magnitude or complex impedance measured through the bipolar electrodes 44a, 44b of the electrode pen 40. The overall impedance monitor 90 samples at 0°, 90°, 180°, 270° phase angles of a signal returned from the electrodes 44a, 44b via the impedance monitor feedback signals IMPMONI_DRV+, IMPMONI_DRV−. By using the transconductance op-amps U4023, U4024, U4026, U4027, U4031, U4032, U4034, and U4035 and the phase angle signals 0° 0 DEG, 90° 90 DEG, 180° 180 DEG, AND 270° 270 DEG, an impedance calculation software routine 198 (FIG. 17) is able to calculate the actual impedance of the material being cut or coagulated (in real and imaginary Cartesian coordinates) from the overall impedance (real and imaginary Cartesian coordinates) and the reference signal impedance (real and imaginary Cartesian coordinates) by compensating out the impedance of the electrodes 44a, 44b themselves. The impedance calculation software routine 198 then converts the actual complex impedance in terms of real and imaginary components into magnitude and phase angle of the actual impedance (Polar coordinates). The magnitude and phase angle of the actual impedance can then be monitored, trended, used for alarming and/or used to stop a particular procedure separately or together.

Figure 5A:
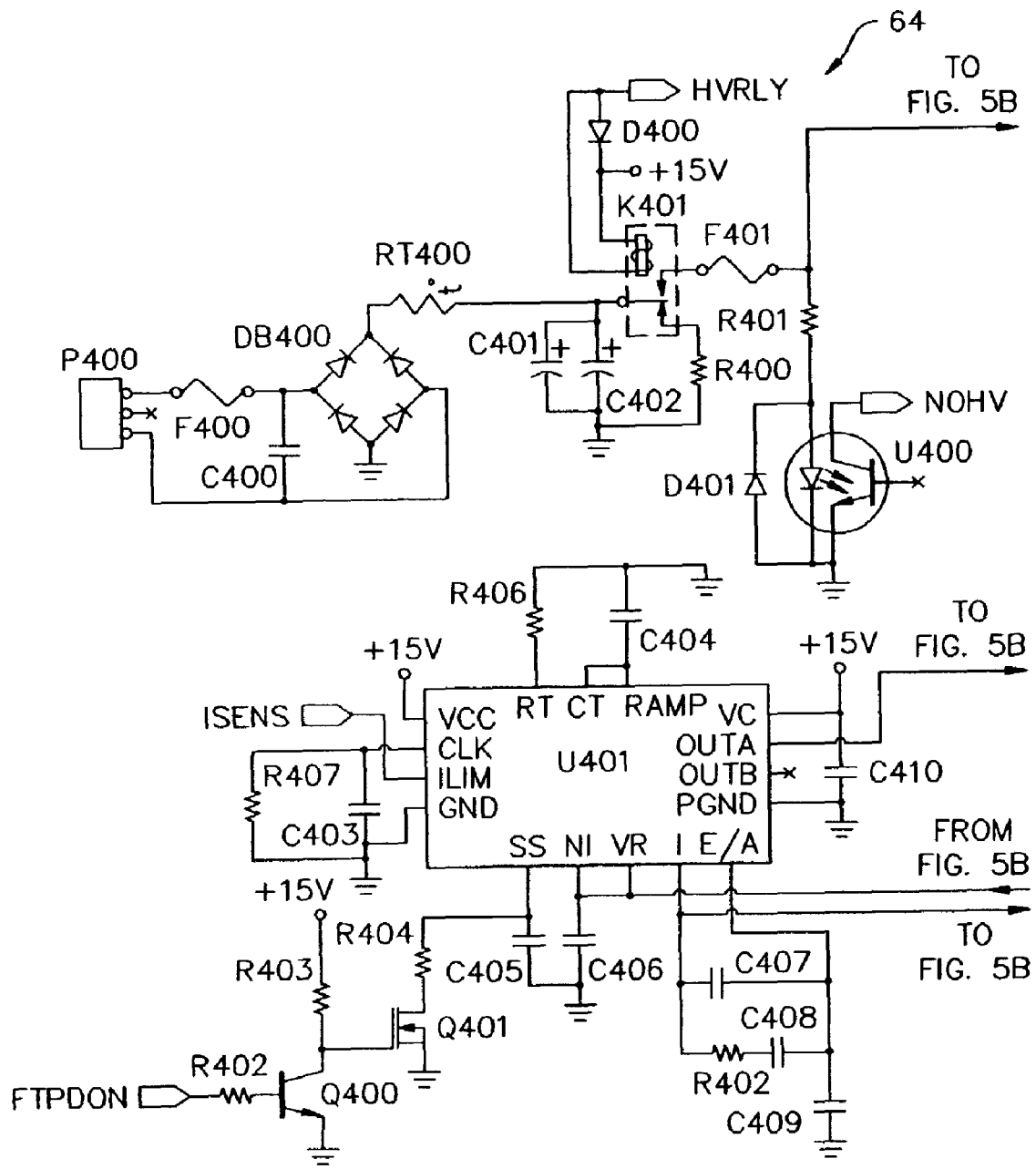
FIGS. 5A–5B are circuit schematic diagrams of a high voltage power supply and various sense circuit supplies for the control circuit of FIG. 2A.
Figure 5B:
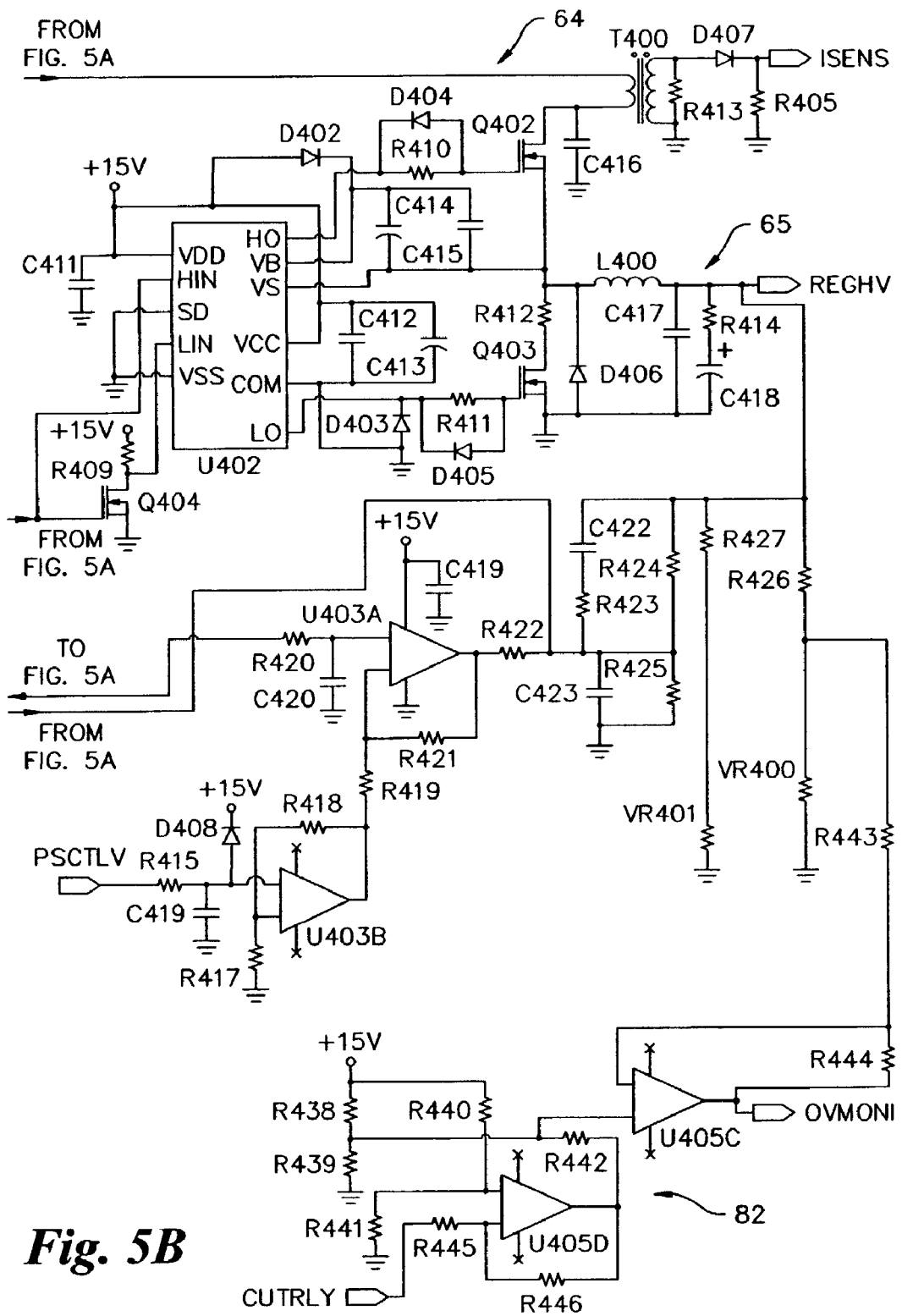

Referring to FIGS. 5A–5B, there is shown a high voltage power supply 64 in accordance with the preferred embodiment of the present invention which is generally disposed on the high voltage power supply board 164. Conventionally available alternating current (e.g., about 120 VAC, 60 Hz) is supplied through the power cord 48 and power plug adapter 49 connected to P400 and then through an in-line fuse F400. The supplied AC power is smoothed through a capacitor C400 before being applied to a diode bridge rectifier DB400. The output of a full wave diode bridge rectifier DB400 is clamped by an in-rush limiter RT400 which provides a signal to contacts of a high voltage power supply relay K401. The high voltage relay K401 is controlled by the high voltage relay signal HVRLY which is generated by the high voltage relay output signal HVRLY_CTL of the main controller U1 gated with the relay on-delay signal RLYDLY., Capacitors C401, C402 smooth the full wave rectified signal from the full wave diode bridge rectifier DB400 and resistor R400 provides a bleed-off when the relay K401 is opened. Once energized, high voltage relay K401 applies DC voltage to a second fuse F401 and the rest of the high voltage power supply circuit 64. An optically isolated transistor U400 in combination with a diode D401 and resistor R401 detect when there is a no high voltage condition and provide a no high voltage signal NOHV to an input of the main controller U1. Current sense transformer T400 in combination with suitable biasing components including resistors R413 and R405, diode D407 and filtering capacitor C416 create a current sense signal ISENS.

A high voltage regulating circuit 65 is also powered through another fuse F401. The high voltage regulating circuit 65 includes a FET driver IC U402 and a high speed pulse width modulating controller (PWM controller) U401. The current sense signal ISENS is applied to a current limiting input of the PWM controller U401 for clamping or limiting the output of the PWM controller U401. An RC oscillator comprising resistor R407 and capacitor C403 serves as a clock for the PWM controller U401. The foot pedal signal FTPDON from the main controller U1 (FIG. 12) gates transistor Q400 through resistor R402, and transistor Q400 allows +15V across resistor R403 thereby allowing a FET Q401, with a suitable filtering capacitor C405, to allow a soft start sink signal to flow to ground thereby selecting a soft start function (ramp up) in the PWM controller U401. The output of the PWM controller U401 is applied directly to a high input of the FET driver IC U402 and to a FET Q404 for gating the low input of the FET driver IC U402. The high and low outputs HO, LO of the FET driver IC U402, along with suitable biasing components including capacitors C412–C415, C417–C418, resistors R410–R412, diodes D402–D406, an inductor L400, drive high MOSFET Q402 and low MOSFET Q403, respectfully to generate the regulated high voltage signal REG HV. The regulated high voltage signal REG HV is applied to the RF amplifier 68 (FIGS. 6A and 6B) to provide cut and/or coagulate output signals to the electrodes 44a, 44b. A power supply control signal PSCTLV is output of the DAC IC U1107 (FIG. 11B) and is controlled or adjusted by the main controller U1. The power supply control signal PSCTLV is applied to op-amp U403B with associated biasing components including resistors R415, R417–R419, capacitor C419 and diode D408. The output of op-amp U403B is applied to op-amp U403A with associated resistors R420–R422 and capacitors C420–C421 and the output of op-amp U403A is then applied to a voltage regulating input of the PWM controller U401 in order to adjust the PWM output of the PWM controller U401. Thus, the main controller U11021 drives the DAC IC U1107 which drives the PWM controller U401. The PWM controller U401, in turn, drives the FET driver IC U402 which pulse width modulates FETS Q402 and Q403 to generate the regulated high voltage REGHV for use by the RF amplifier circuit 68. Accordingly, a change in the power supply control signal PSCTLV causes a proportional change in the regulated high voltage REGHV being output from the high voltage power supply 64. Other circuit implementations for generating regulated high voltage DC, such as the regulated high voltage power supply disclosed in U.S. Pat. No. 5,318,563 of Malis et al., may be utilized without departing from the broad inventive scope of the present invention.

The high voltage power supply 64 also includes an over voltage monitoring circuit 82. The over voltage monitoring circuit 82 includes op-amps U405C–U405D and resistors R438–R446 and generates an over voltage monitor signal OVMONI to the main controller U1 when the regulated high voltage REGHV has exceeded a predetermined value for alarming and/or interlocking purposes. For example, if an over voltage condition is detected, the main controller U1 can either reduce the power supply control voltage PSCTLV or de-energize the high voltage relay K401 via the high voltage relay output signal HVRLY_CTL.

Referring to FIG. 6C, a data output circuit 30 includes an RS232 line driver IC U6004, various biasing capacitors C6019 and C6021–C6024 and a data output port P6013. A serial data out signal DATA_OUT from the main controller U1 is applied to the RS232 line driver IC U6004. The RS232 line driver IC U6004 converts the serial data out signal DATA_OUT to a corresponding RS232 compliant signal TXD on pin 2 of the data output port P6013. The data output port P6013 is preferably a 25 pin DIN connector of the DB-25 type; however, the data output port P6013 could be other connector types such as a 9 pin DIN connector of the DB-9 type or even other connectors without departing from the present invention. Further, it is obvious that a receive signal (not shown) could be connected from the data output port P6013 to the RS232 line driver IC U6004 and from the RS232 line driver IC U6004 to the main controller U1 in order to also receive data as is well know in the art. Even further, other line drivers such as RS485, Ethernet and the like may be substituted for the RS232 line driver IC U6004 along with appropriate associated circuitry necessary to make the other line drivers functional within the context shown herein without departing from the present invention.

A foot pedal detection circuit 32 includes an input jack J6008 and conditioning inductors L6012–L6013. A foot pedal switch set (not shown) is normally connected to the input jack J6008 to allow a user, such as a surgeon, to use the different modes of operation of the RF generator 50 without using his or her hands because users are typically holding at least the surgical pen 40 during a particular procedure. A coagulation mode foot pedal signal COAG_FTPDL is conditioned by inductor L6014 when a coagulation foot pedal switch is closed or otherwise operated. Similarly, a cut mode foot pedal signal CUT_FTPDL is conditioned by inductor L6013 when a cut foot pedal switch is closed or otherwise operated. In like fashion, a lavage foot pedal signal LAVA_FTPDL is conditioned by inductor L6012 when a lavage foot pedal switch is closed or otherwise operated. The coagulation mode foot pedal signal COAG_FTPDL, the cut mode foot pedal signal CUT_FTPDL and the lavage foot pedal signal LAVA_FTPDL are all connected to a foot pedal interface circuit 33 on the controller board 155 (FIG. 11B). The foot pedal interface circuit 33 includes resistors R1152–R1154, capacitors C1151–C1153 and diodes D1103–D1105. A fixed voltage is applied across the resistors R1152–R1154, in this case (+) 5 volts DC, and is applied to each signal line for the coagulation mode foot pedal signal COAG_FTPDL, the cut mode foot pedal signal CUT_FTPDL and the lavage foot pedal signal LAVA_FTPDL, respectively. When one of the foot pedal switches is closed, current flows through the respective switch to ground thereby allowing the capacitors C1151–C1153 to discharge through respective inductors L1112–L1113 and allowing the voltage to drop on the other side of diodes D1103–D1105. Signals COAGFTPDL, CUTFTPDL, and LAVAFTPDL corresponding to the coagulation mode foot pedal signal COAG_FTPDL, the cut mode foot pedal signal CUT_FTPDL and the lavage foot pedal signal LAVA_FTPDL, respectively, are connected to diodes D1103–D1105 and are connected to inputs of the main controller U1 on the SMT controller board 162. The main controller U1 determines, through various software, if a particular mode is applicable based upon the input signals for the coagulation mode foot pedal signal COAGFTPDL, the cut mode foot pedal signal CUTFTPDL, and the lavage foot pedal signal LAVAFTPDL and other present conditions and provides output signals for use by various other circuits for coagulation mode signal COAG, cut mode signal CUT, lavage mode signal LAVAGE. Further, the main controller U1 determines when any of the input signals for coagulation mode foot pedal signal COAGFTPDL, cut mode foot pedal signal CUTFTPDL, and lavage foot pedal signal LAVAFTPDL indicate that a foot pedal switch is closed and outputs a foot pedal on signal FTPDON for use by at least the PWM controller U401, the RF amplifier controller U1102 and the tone generator 98.

Figure 7:
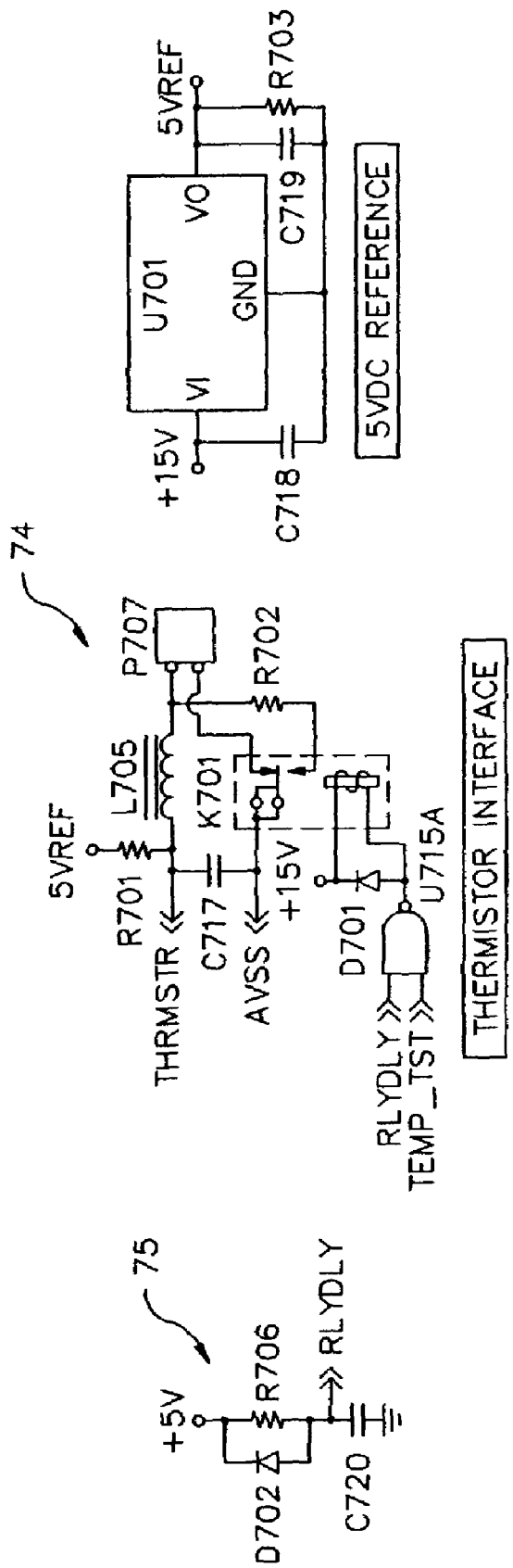
FIG. 7 is a circuit schematic diagram of input/outputs for the control circuit of FIG. 2A.

The controller board 155 further includes the temperature sense or thermistor interface circuit 74 as shown on FIG. 7. The thermistor interface 74 includes resistors R701, R702, capacitors C717, inductor L705, diode D701, NOT gate U715A and relay K701. A voltage reference, in this case 5 volts DC, is applied to the thermistor 72 across resistor R701 providing excitation voltage for the thermistor 72. In normal operation, the thermistor generates a temperature input voltage signal THRMSTR which is conditioned by the temperature sense control circuit 74 which varies generally linearly with variations in temperature to a practical extent, as is known in the art. The other terminal of the thermistor 72 is tied to an alternate voltage sink AVSS which is merely an alternative resistive path (resistor R6 on FIG. 12) to ground. The NAND gate U715A selectively energizes the temperature test relay K701 whenever the startup delay relay signal RLYDLY from a power on-delay circuit 75 or a temperature test signal TEMP_TST from the main controller U1 are high. When the temperature test relay K701 is energized, resistor R702 simulates a fixed value on the temperature input voltage signal THRMSTR. Preferably, resistor R702 is a precision resistor with a tolerance of about 1% or better. Preferably, resistor R702 has a resistance value which generally corresponds to a resistance value generated by the thermistor 72 when the temperature is about 40° C. Of course, resistor R702 could be selected with other tolerances and other resistance values without departing from the present invention. It is contemplated that resistor R702 is a variable resistance device such as a multi-resistor switch-selectable block for generating user selectable voltages when testing the overall PF generator 50.

The power on-delay circuit 75 includes a resistor R706, a capacitor C720 and a diode D702. A fixed voltage, in this case (+) 5 volts DC is applied across resistor R706 in order to charge capacitor C720. The power on-delay circuit 75 provides the startup delay relay signal RLYDLY after capacitor C720 is fully charged. The startup delay relay signal RLYDLY is used throughout the control circuit 59 to reset various circuits and/or devices on power up and to prevent unexpected events from occurring on power up (of the overall control circuit 59) because various circuits and/or controllers are in unexpected conditions just after power up. Other circuit implementations such as timer IC's or timer controlled relays may be used in place of the power on-delay circuit 75 to generate the startup delay relay signal RLYDLY without departing from the present invention.

A voltage regulator IC U701 provides a regulated 5 VREF for use throughout the control circuit 59. The voltage regulator IC U701 accepts +15 volts DC and, along with suitable biasing components including capacitors C718–C719 and resistor R703, generates the regulated 5 volts DC 5VREF.

Referring to FIG. 8, the low voltage isolated supply 66 provides regulated low voltage outputs of approximately (+) 3–7 volts DC, (+) 12–15 volts DC, and (−) 12–15 volts DC. Preferably, the output of the isolated supply 66 has outputs of (+) 5 volts DC+5VAUX, (+) 15 volts DC+15AUX and (−)

15 volts DC−15VAUX. Isolated supply 66 includes a dual-ended transformer T803 and a voltage regulator IC U110811. The isolated supply 66 also includes capacitors C840–C843, resistors R837–R838, diodes D818 and D820, and clipper diode D819. The stimulate pulse signal STIM_PS gates the transistor Q806 at a frequency set by the 78.125 KHz and 156.25 KHz clock signals so that an alternating signal can be created with clipper diode D819 to drive the primary winding of transformer T803. The diode D818 and capacitor C842 provide the (+) 15 volts DC+15AUX. The oppositely oriented diode D820 and capacitor C843 provide the (−) 15 volts DC−15VAUX. The voltage regulator IC U110811 provides a more precisely regulate (+) 5 volts DC+5VAUX from the (+) 15 volts DC+15AUX. The regulated voltages (+) 5 volts DC+5VAUX, (+) 15 volts DC+15AUX and (−) 15 volts DC−15VAUX are used throughout the control circuit 59 as low voltage supply as is known in the art.

Figure 9:
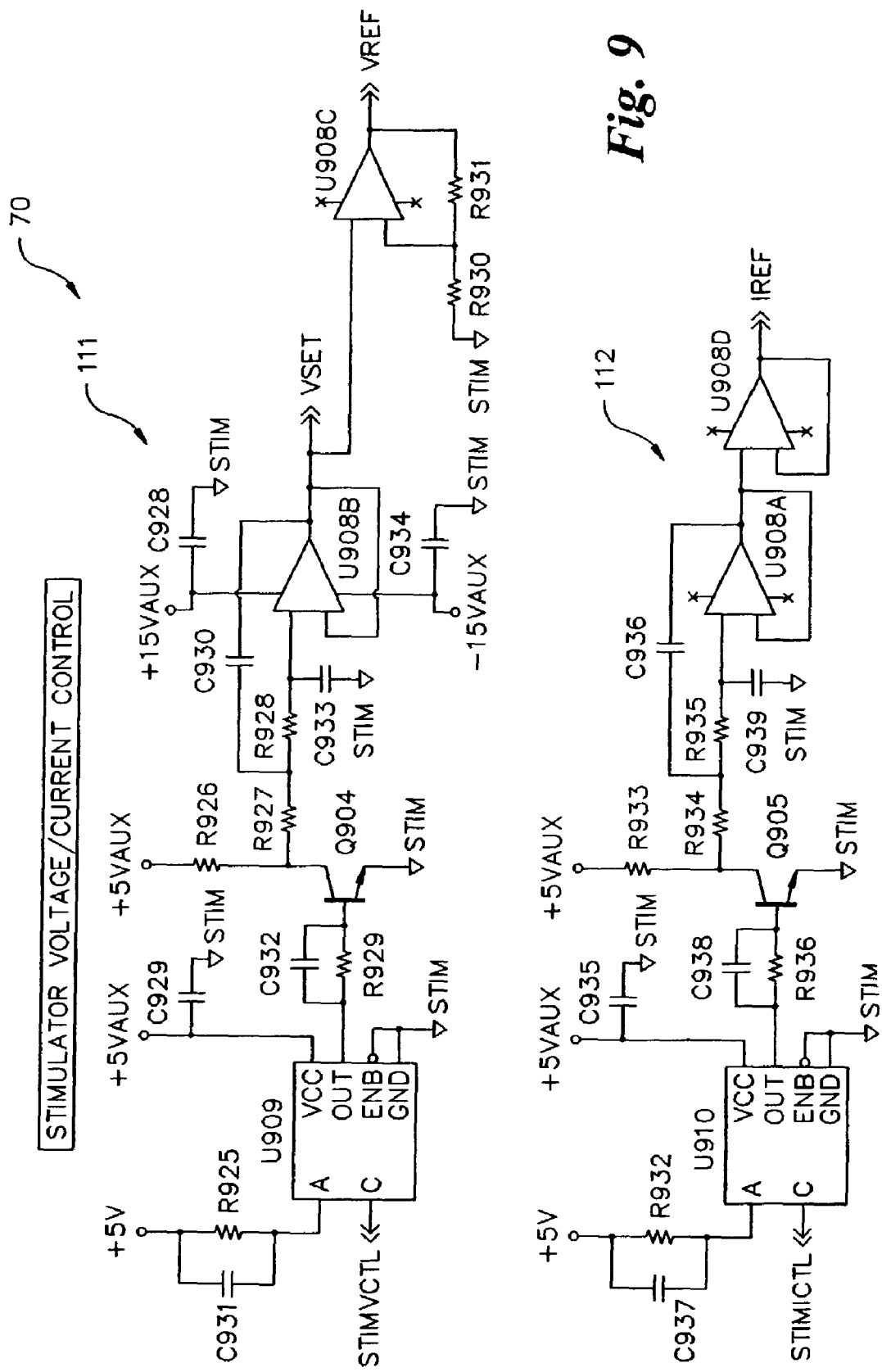
FIG. 9 is a circuit schematic diagram of a stimulator voltage/current control circuit for the control circuit of FIG. 2A.

Referring to FIG. 9, the main board 159 further includes a stimulator voltage control circuit 111 and a stimulator current control circuit 112 of the stimulator circuit 70. The stimulator voltage control circuit 111 includes opto-coupler IC U909 and op-amps U908B and U908C. Positive (+) 5 volts is applied through a resistor capacitor network comprising resistor R925 and capacitor C931 to the anode of opto-coupler IC U909 and a stimulator voltage control signal STIMVCTL output from the main controller U1 is applied to the cathode of opto-coupler U909. The output is directed across resistor R929 and capacitor C932 to drive transistor Q904 the output of which is dropped across resistors R927–R928 with suitable filtering capacitors C928, C930, C933–C934 to the input of op-amp U908B. The output of op-amp U908B is applied to the input of op-amp (buffer) U908C with suitable biasing resistors R930–R931. The output of op-amp U908B is a stimulate voltage set VSET voltage and the output of op-amp U908C is stimulate voltage reference VREF. The stimulator current control circuit 112 includes opto-coupler IC U910 and op-amps U908A and U908D. Similar to the stimulator voltage control circuit 111, positive (+) 5 volts is dropped across resistor R932 and capacitor C937 to the anode of opto-coupler IC U910 and a stimulator current control signal STIMICTL output from the main controller U1 is applied to the cathode of opto-coupler U910. The output of opto-coupler IC U910 is dropped across resistor R936 and capacitor C938 to drive transistor Q905. The output of transistor Q905 in combination with resistors R933–R935 and capacitors C936 and C939 apply the input voltage to op-amp (buffer) U908A. The output of op-amp U908A is applied to the input of op-amp (buffer) U908D, and the output of op-amp U908D provides a current reference voltage IREF.

Figure 10A:
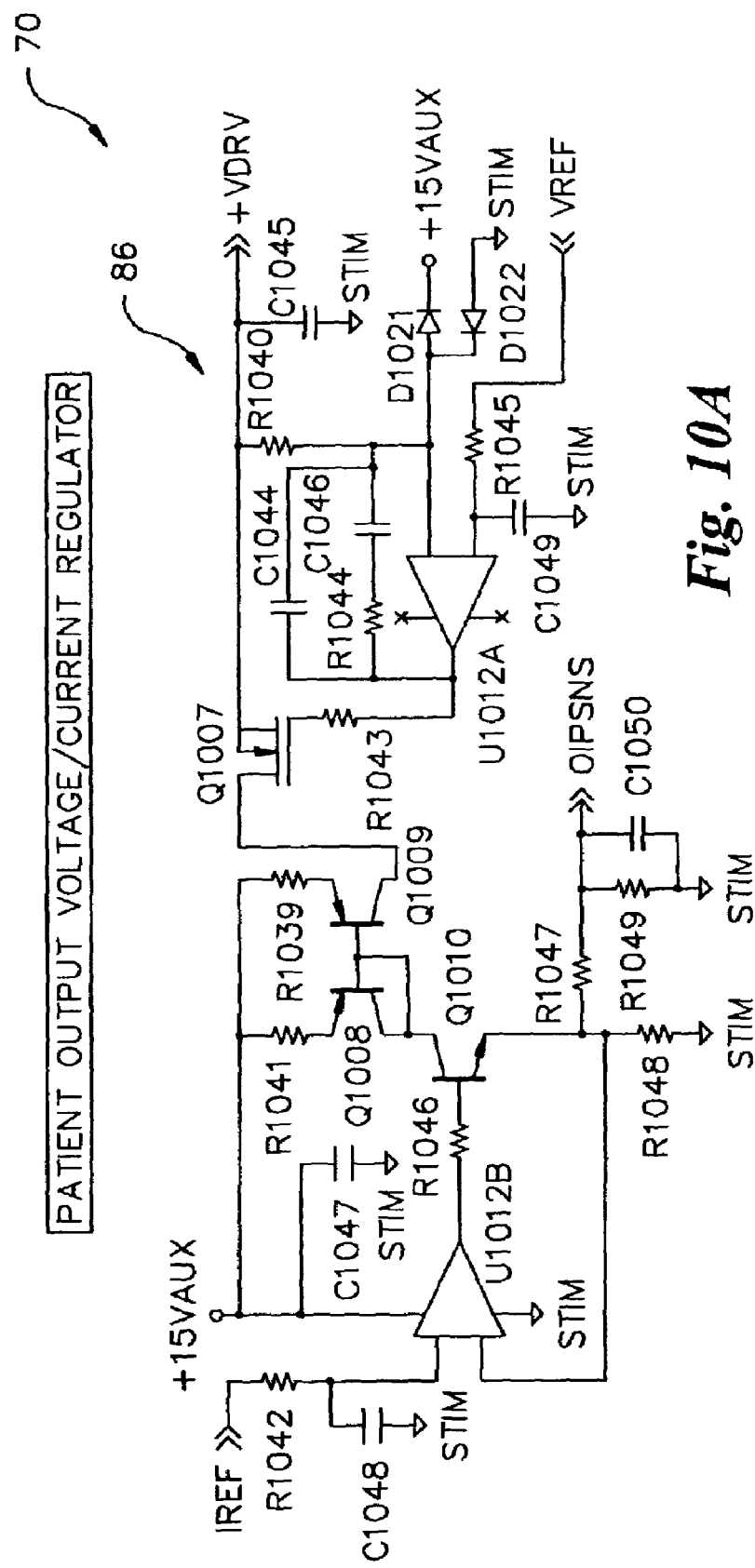
FIGS. 10A–10C are circuit schematic diagrams of a patient output voltage/current regulator circuit for the control circuit of FIG. 2A.
Figure 10B:
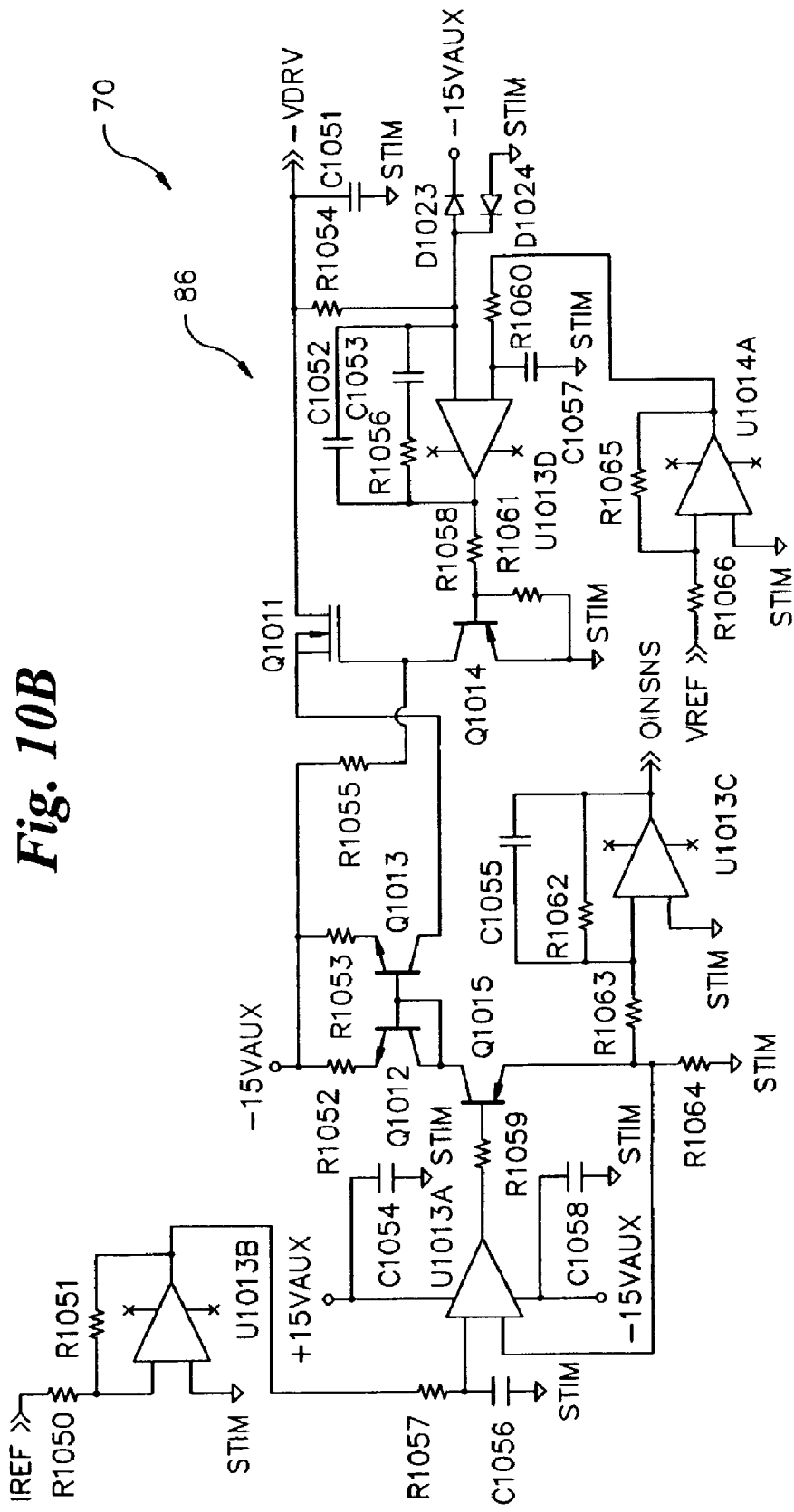
Figure 10C:
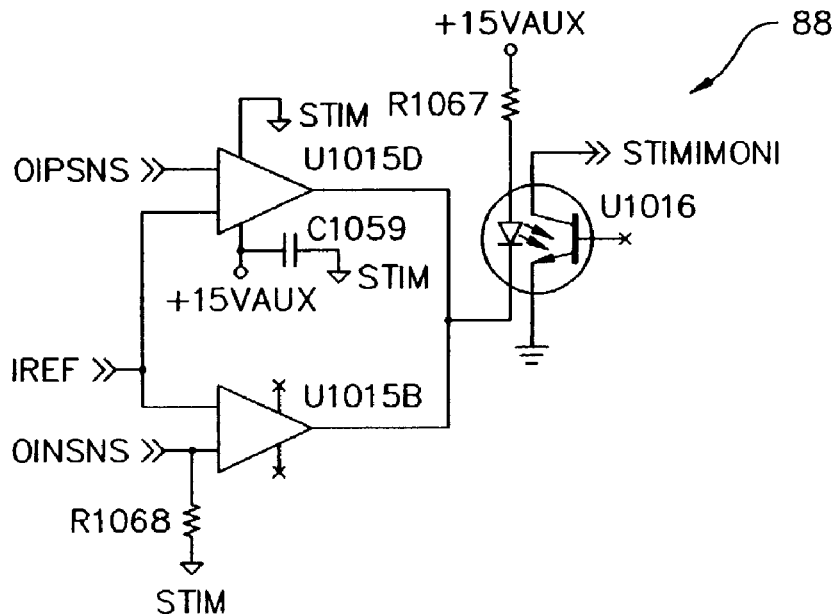
Figure 10C:
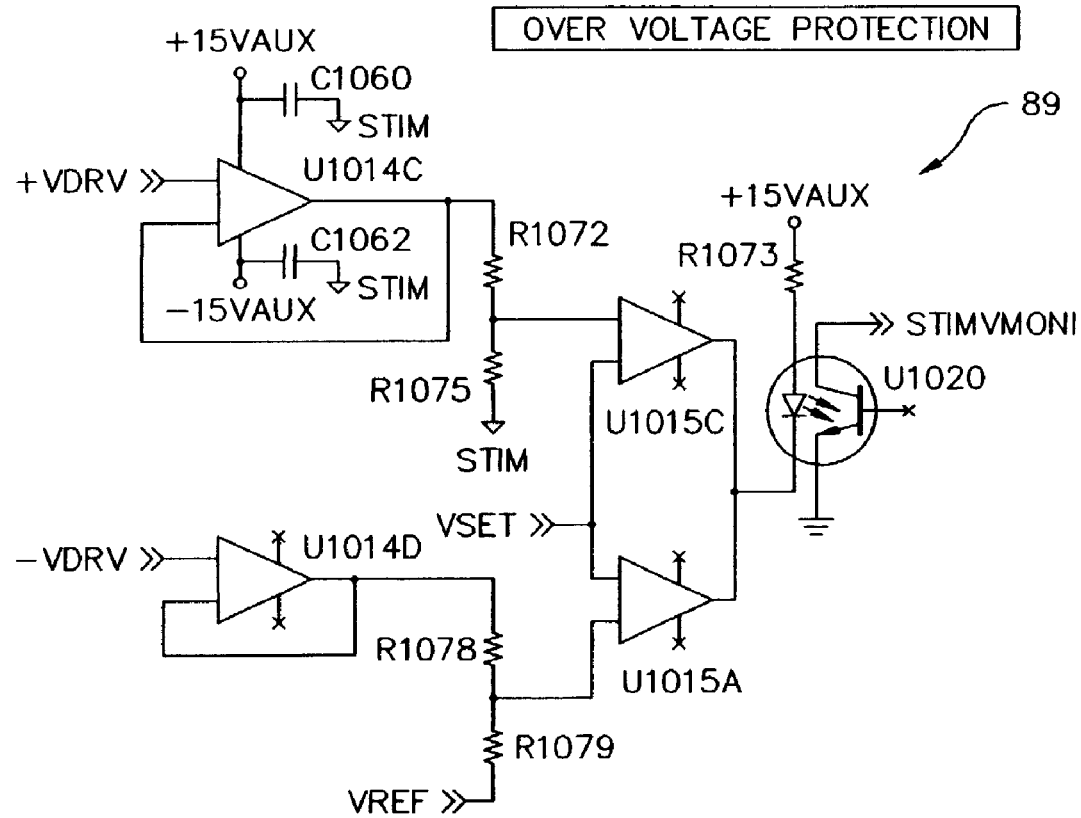

Referring to FIGS. 10A–10C, the stimulator circuit 70 further includes a patient output voltage/current regulator or patient regulator 86. The patient regulator 86 includes op-amps U1012A–U1012B, transistors Q1007–Q1010 and suitable biasing components including resistors R1039–R1044 and R1046–R1049, capacitors C1045–C1050 and diodes D1021–D1022. The current reference voltage IREF (FIG. 9) from the stimulator current control circuit 112 is applied to op-amp U1012B and the output of op-amp U1012B is dropped across resistor R1046 to drive a transistor amplifier bridge Q1008–Q1010. The stimulate voltage reference VREF (FIG. 9) from the stimulator voltage control circuit 111 is applied to op-amp U1012A and the output of the op-amp U1012A is dropped across resistor R1043 to drive FET Q1007 which gates a signal from transistor amplifier bridge Q1008–Q1010 thereby outputting a simulate positive drive signal +VDRV. The output of op-amp U1012A also creates a positive output sense signal OIPSNS through resistor R1047 and across resistor R1049 and capacitor C1050 to regulate the positive output in stimulate mode based on current and voltage.

The patient regulator circuit 86 further includes op-amps U113A–U113D and U1014A and transistors Q1011–Q1015. In conjunction with the op-amps U1113A–U1013D and transistors Q1011–Q1013 and Q1015 are suitable biasing components including resistors R1050–R1066, capacitors C1051–C1058 and diodes D1023–D1024. The current reference voltage IREF from stimulator current control circuit 112 is applied across resistor R1050 to op-amp U1013B which is dropped across resistor R1057 and applied to op-amp U1013A. The output of U1013A is dropped across resistor R1059 to drive transistor Q1015 of transistor amplifier bridge Q1012–Q1013 and Q1015. The stimulate voltage reference VREF is applied across resistor R1066 to the input of op-amp U1014A having a feedback resistor R1065 and the output of op-amp U014A is applied across resistor R1060 to the input of op-amp U1103D. The output of U1013D is dropped across resistor R1058 to drive transistor Q1014 which gates FET Q1001. The output of the transistor amplifier bridge Q1012–Q1013, Q1015 is applied through FET Q1011 to create a simulate negative drive signal −VDRV. The output of op-amp U1013A also creates a negative output sense signal OINSNS through resistor R1063 and op-amp U1013C with feedback resistor R1062 and smoothing capacitor C1055 to regulate the negative output in stimulate mode based on current and voltage.

The stimulator circuit 70 further includes an over current protection circuit 88. The over current protection circuit 88 includes comparators U1015B and U1015D and optical isolation transistor U1016. The over current protection circuit 88 also includes suitable biasing components including resistors R1067–R1068 and capacitor C1059. The positive and negative output sense signals OIPSNS, OINSNS are applied to comparators U1015D and U1015B, respectively, and are compared to the current reference voltage IREF from the stimulator current control circuit 112 (FIG. 9). The output of the comparators U1015D, U1015B is applied to the optical isolation transistor U1016 to generate a stimulator current monitor signal STIMONI to the main controller U1, at for example RB6, when an over current condition is detected.

The stimulator circuit 70 also includes an over voltage protection circuit 89. The over voltage protection circuit 89 includes op-amps U1014C, U1014D and comparators U1015A and U1015C. The over voltage protection circuit 89 also includes an optical isolation transistor U1020 and suitable biasing components including resistors R1072–R1073, R1075 and R1078–R1079 and capacitors C1060 and C1062. The simulate positive drive voltage +VDRV is applied to an input of op-amp U1014C and the simulate negative drive voltage −VDRV is applied to an input of the op-amp U1014D. The output of op-amp U1014C is dropped across resistor R1072 and is applied to an input of comparator U1015C. The output of op-amp U1014D dropped across resistor R1078, in combination with the stimulate voltage reference VREF is dropped across resistor R1079, and is then applied to an input of comparator U1015A. The stimulate voltage set signal VSET is applied to the other input of comparator U1015C and to the other input of comparator U1015A. The outputs of comparators U1015A and U1015C are applied to the optical isolation transistor U1020, and the output of the optical isolation transistor U1020 provides a stimulator voltage monitor signal STIMVMONI to the main controller U1, at for example RB7, when an over voltage condition is detected.

Referring to FIG. 13, stimulator circuit 70 further includes an output drive circuit 110. The output drive circuit 110 includes single pole double throw (SPDT) IC switches U1317–U1318 and opto-coupler ICs U1319 and U1321. The output drive circuit 110 further includes suitable biasing components including resistors R1369–R1371, R1374 and R1376, capacitors C1361, C1363 and C1364 and diodes D1325–D1327. The stimulate positive drive voltage +VDRV and stimulate negative drive voltage −VDRV are applied through the first SPDT IC switch U1317 and then through the second SPDT IC switch U1318. The IC SPDT switches U1317, U1318 are driven by a stimulating pulse positive signal STIMPULSE+ from the RF amplifier controller U1102 and a stimulating pulse negative STIM-PULSE− from the RF amplifier controller U1102, respectively, through the opto-coupler ICs U1319, U1321. The RF amplifier controller U1102 controls the stimulating pulse positive signal STIMPULSE+ and the stimulating pulse negative STIMPULSE− based upon a predetermined duty cycle determined in software. The output of SPDT IC switch U1318 provides the first stimulate output voltage STI-MOUT1 when stimulate mode is selected and the foot pedal is depressed. The second stimulate output voltage STI-MOUT2 is switched by relay K1303 between a stimulate ground or ground reference STIM and a ground pad GND-PAD. The coil of relay K1303 is energized by the monopolar mode relay signal MONRLY thereby connecting the second stimulate output voltage STIMOUT2 to the ground pad GNDPAD when monopolar mode is selected. The first and second stimulate output voltage signals STIMOUT1, STI-MOUT2 are connected to contacts of relay K6002 to be selectively applied to the electrodes 44a, 44b when stimulate mode is selected and the foot pedal is depressed.

Figure 14:
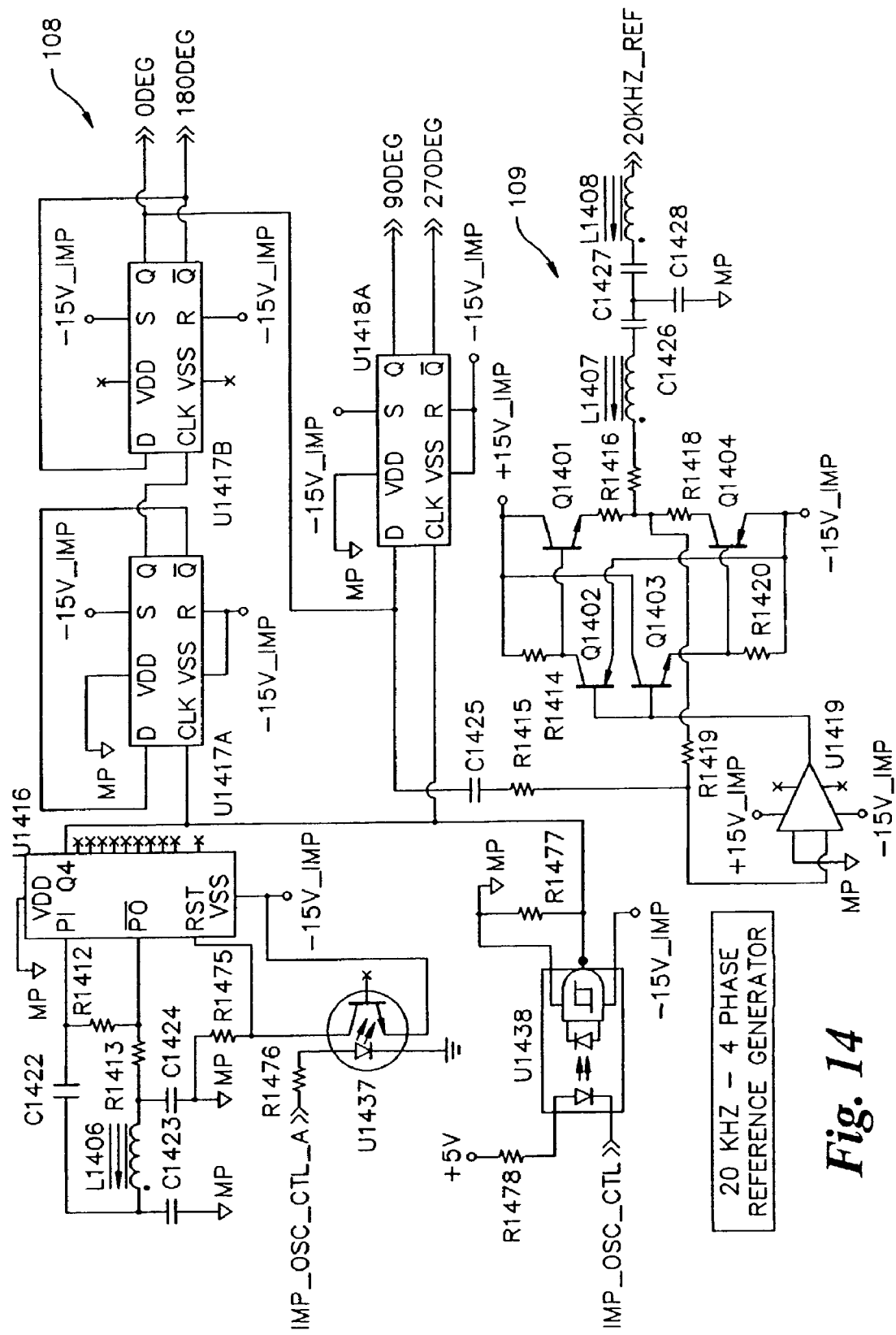
FIG. 14 is a circuit schematic diagram of a four-phase reference generator for the control circuit of FIG. 2A.

Referring to FIG. 14, the four-phase reference generator circuit 108 includes a multi-stage counter oscillator IC U1416, IC flip-flops U1417A–U1417B and U1418A, optically isolated not gate U1438, buffer op-amp U1419, optically isolated transistor U1437 and transistors Q1401–Q1404. The four-phase reference generator circuit 108 further includes inductors L1406–L1408, resistors R1412–R1420 and R1475–R1478, and capacitors C1422C 1427. The four-phase reference generator basically provides sequentially a 0° signal 0DEG, a 90° signal 90DEG, a 180° signal 180DEG and a 270° signal 270DEG based on the phase angle of the sine reference signal 20KHZ_REF for use by the impedance monitor 90 when the multi-stage counter oscillator IC U1416 receives an impedance oscillator on signal IMP_OSC_CTL_A from the impedance controller U1120 and an impedance oscillator control signal IMP_OSC_CTL. The impedance oscillator control signal IMP_OSC_CTL is a function of the impedance oscillator on signal IMP_OSC_CTL_A (FIG. 11) which is AND gated with a clock frequency, in this case 78.125 KHz. The impedance controller U1120 determines when to test for impedance based upon software. The four-phase reference generator circuit 108 also provides the sine reference signal 20KHZ_REF which is applied to the reflectometer bridge 92 of the impedance detection circuit 90 (FIG. 4A) through a reference amplifier circuit 109 which includes transistors Q1401–Q1404 and resistors R1414–R1420.

As described herein above, the control circuit 59 controls a variable output signal to bipolar electrodes 44a, 44b used in electrosurgical procedures and includes the HV DC power supply circuit 66 that provides regulated low voltage and high voltage outputs and the radio frequency waveform generator circuit or RF amplifier 68 that provides PDM of a carrier signal. The carrier signal directly affects the variable output signal to the bipolar electrodes 44a, 44b.

Referring to FIGS. 15A–15H, the touchscreen 54 includes screens 120–127 for displaying the data. The onscreen indicators 130 display data in alphanumeric-style values. The onscreen indicators 130 may also include bar graphs. Preferably, the onscreen indicators 130 display one of a pulse width setting, a frequency setting, a voltage setting, an amperage setting, a measured temperature value, a temperature set point value, a measured impedance value, an actual time, an elapsed time, a remaining time, and a time set point value. Optimally, the RF generator 50 onscreen indicators 130 displaying all the previously mentioned values. Preferably, the onscreen indicators 130 display also at least one of an operating mode, an alarm status, a calibration status, a maintenance status and a selected user parameter. The touchscreen 54 has at least one screen 120–127 having an onscreen field 132 for allowing a user to enter a set point. The onscreen field 132 preferably allows entry of at least one of a pulse width setting, a frequency setting, a voltage setting, an amperage setting, a temperature set point value, and a time set point value. Preferably, the screens 120–127 include onscreen fields 132 that include all the previously mentioned values. Further, the touchscreens 120–127 have an onscreen software pushbuttons 134a–134c having a first state and a second state. Preferably, the onscreen software pushbuttons 134a–134c are pressed to hold and pressed to release and include a save current setting pushbutton 134a, a load profile pushbutton 134b and an escape pushbutton 134c. Further, the screens 120–127 preferably include an onscreen software selector switch 136 having a first position and a second position such as, for example, a monopolar/bipolar mode selector switch 136.

Figure 16:
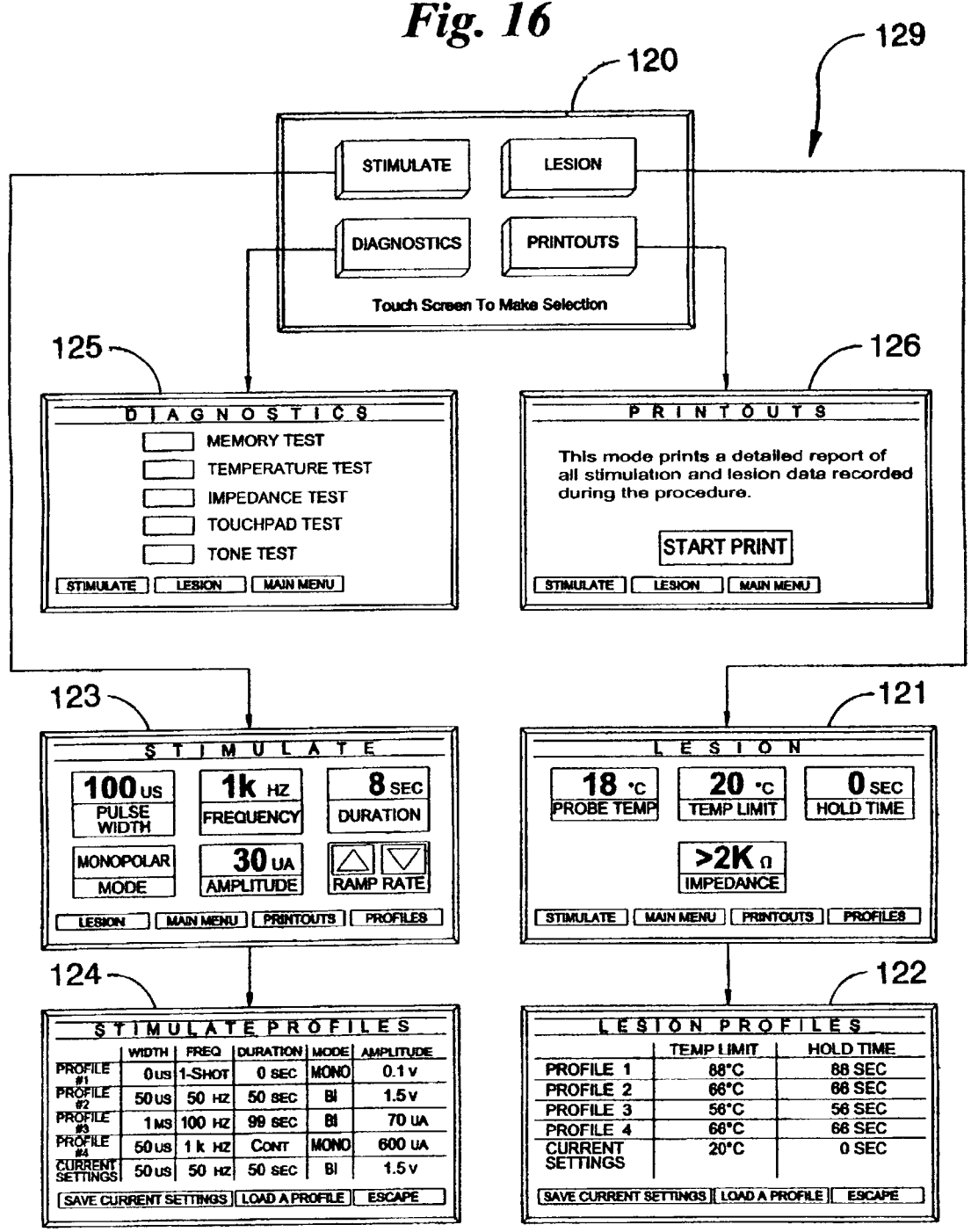
FIG. 16 is an overview diagram of the software screens of FIGS. 15A–15G.

The screens 120–127 are preferably navigable using onscreen menu buttons 138a–138g to switch between screens 120–127 including a stimulate screen button 138a, a lesion screen button 138b, a diagnostics screen button 138c, a printouts screen button 138d, a main menu button 138e, a lesion profiles screen button 138f and a stimulate screen profiles button 138g. FIG. 16, shows a navigation menu tree 129 for navigating between screens 120–127 using the onscreen menu buttons 138. While the preferred embodiment is demonstrated in FIG. 16 other ways of navigating between screens 120–127 and other types of onscreen menu buttons may be utilized without departing from the broad inventive scope of the present invention.

Figure 15A:
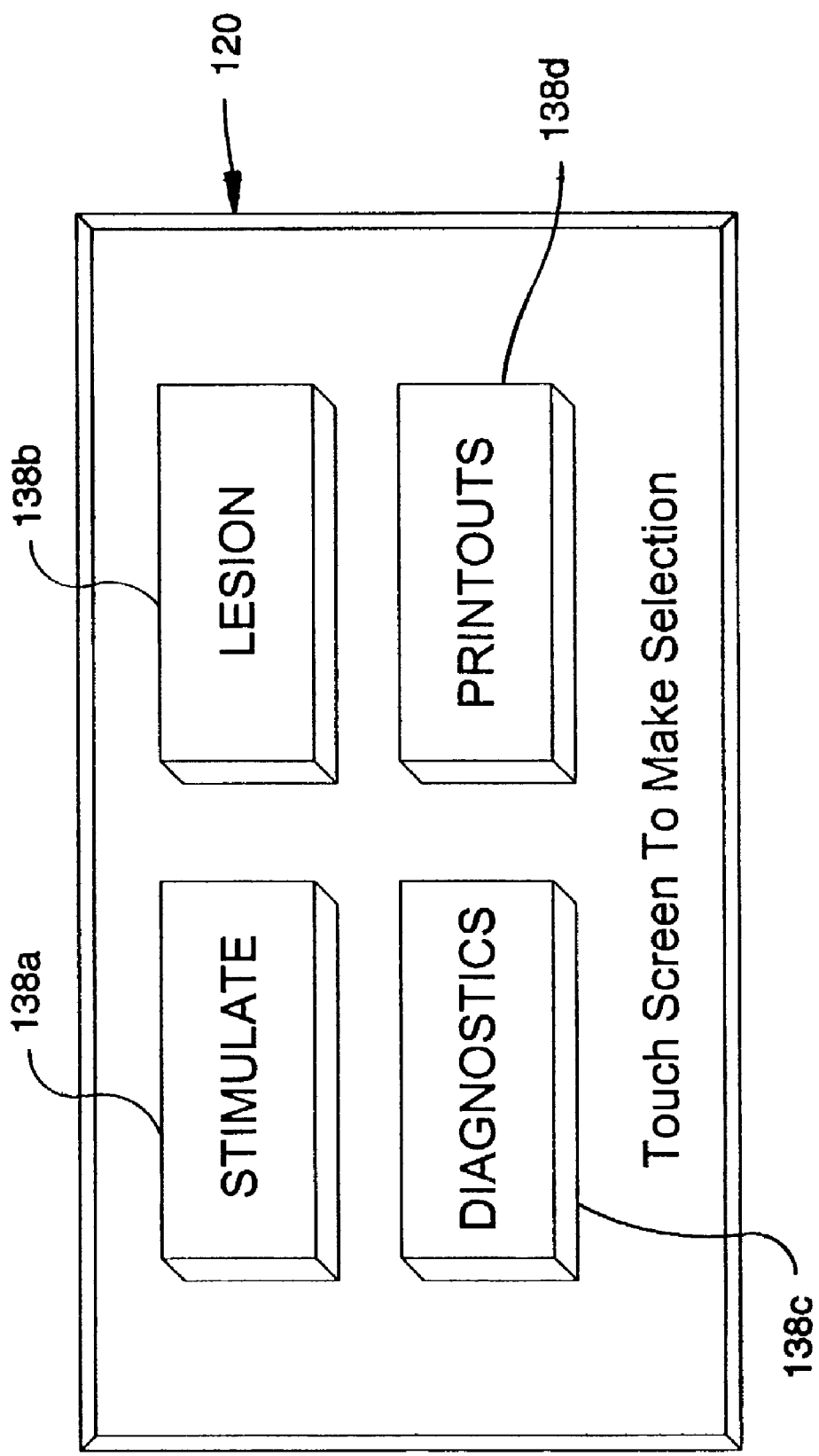
FIGS. 15A–15G are screen diagrams for a touchscreen display of the electrosurgical generator of FIG. 1A.

Referring to FIG. 15A in detail, onscreen menu buttons 138a–138d are provided to jump or go to the stimulate screen 123 (FIG. 15D), the lesion screen 121 (FIG. 15B), the diagnostics screen 125 (FIG. 15F) and a printout screen 126 (FIG. 15G), respectively. Preferably, screen 120 is a top or main screen for the user to return to between modes or on power-up as shown in FIG. 16. However, the screens 120–127 may include other versions of a main screen 120 that is more complicated or that uses pop-up menus or the like without departing from the present invention.

Figure 15B:
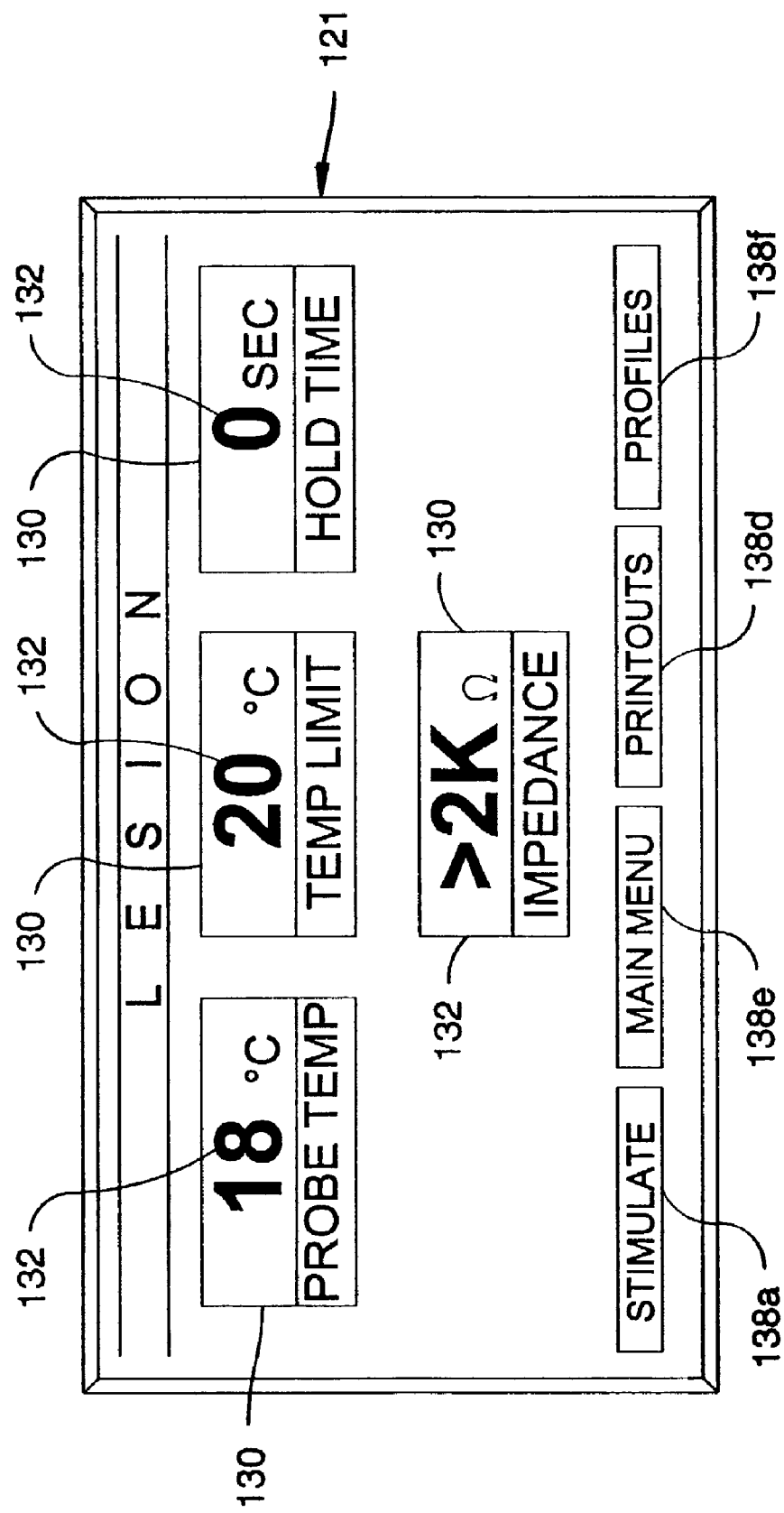
Figure 15C:
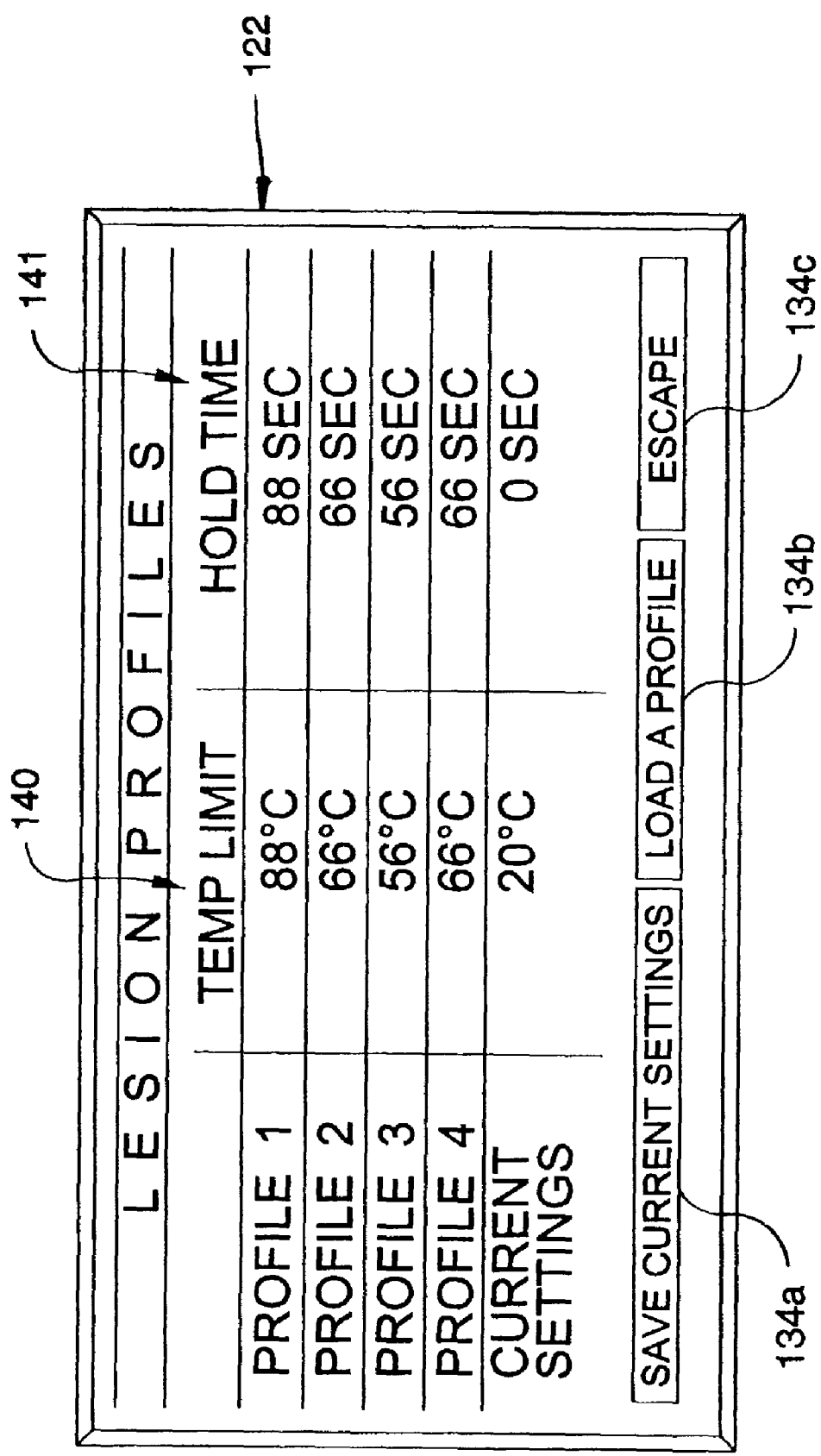

Referring to FIG. 15B in detail, the lesion screen 121 includes onscreen menu selector buttons 138a, 138e, 138d and 138f for the stimulate screen 123, the main menu 120, the printout screen 126 and a stimulate profile screen 124 (FIG. 15E), respectively. The lesion screen 121 also includes onscreen indicators for probe temperature, temperature limit, hold time and impedance. The onscreen indicators 130 also act as onscreen modifiable entry fields 132 such that when a user touches an area of the screen near the onscreen indicators 130 and a numeric keypad pops up allowing user entry of a preset or set point. For example, if the user presses the onscreen indicator 130 for the temperature limit 140 (FIG. 15C), a numeric keypad with the numbers 0–9 and "escape" and "enter" appears allowing the user to enter a temperature preset in ° C. such as 20° C., hitting "enter" returns the screen to its original appearance with the new set point entered into the main controller U1 and flash memory IC U1108. By selecting the lesion profiles onscreen menu button 138f, the lesion profile screen 122 is displayed as shown in detail in FIG. 15C. The lesion profile screen 122 has a table of onscreen indicators 130 which also act as onscreen modifiable entry fields 132. The lesion profile screen 122 includes onscreen menu buttons 134a–134c for saving current settings, loading a profile, and "escape", respectively, which would return to screen 121 (FIG. 15B). The lesion profiles include a list of temperature limits 140 and hold times 141 for different profiles (i.e., profile 1, profile 2, profile 3, profile 4 or profile 1–profile 4). The lesion profile screen also displays the current settings. The profiles (profile 1–profile 4) can be for a particular doctor or for a particular technician or a particular procedure. It is contemplated that the profiles (profile 1–profile 4) can be renamed by touching the onscreen software pushbutton and typing in a procedure name such as "lesion generation" or a doctor's name, such as "Dr. Smith." During a particular procedure, the temperature control loop will drive the temperature of the electrosurgical pen 40 to the preset temperature limit 140 and hold the temperature at the temperature limit for the hold time 141 in the current settings. The profiles or user defined parameters (profile 1–profile 4) are first entered on the lesion profile screen 122, then stored in a memory location in the flash memory IC U1108 and later selected by a user by using the load a profile button 134b. The same method for entering the user defined setup parameters is used for both the temperature limit 140 and hold time 141. Once the soak time or hold time preset 141 is used by the counter in the main controller U1, the main controller U1 measures an actual temperature at the bipolar electrodes 44a, 44b using the thermistor 72 located in the tip of the electrosurgical pen 40 and the temperature sense circuit 74. When the actual temperature is approximately equal to the temperature set point or limit 140, the timer compares an elapsed time to the hold time 141 and once the elapsed time is equal to the hold time 141 the main controller U1 reduces the power of the output signal to the bipolar electrodes 44a, 44b to approximately zero.

Figure 15D:
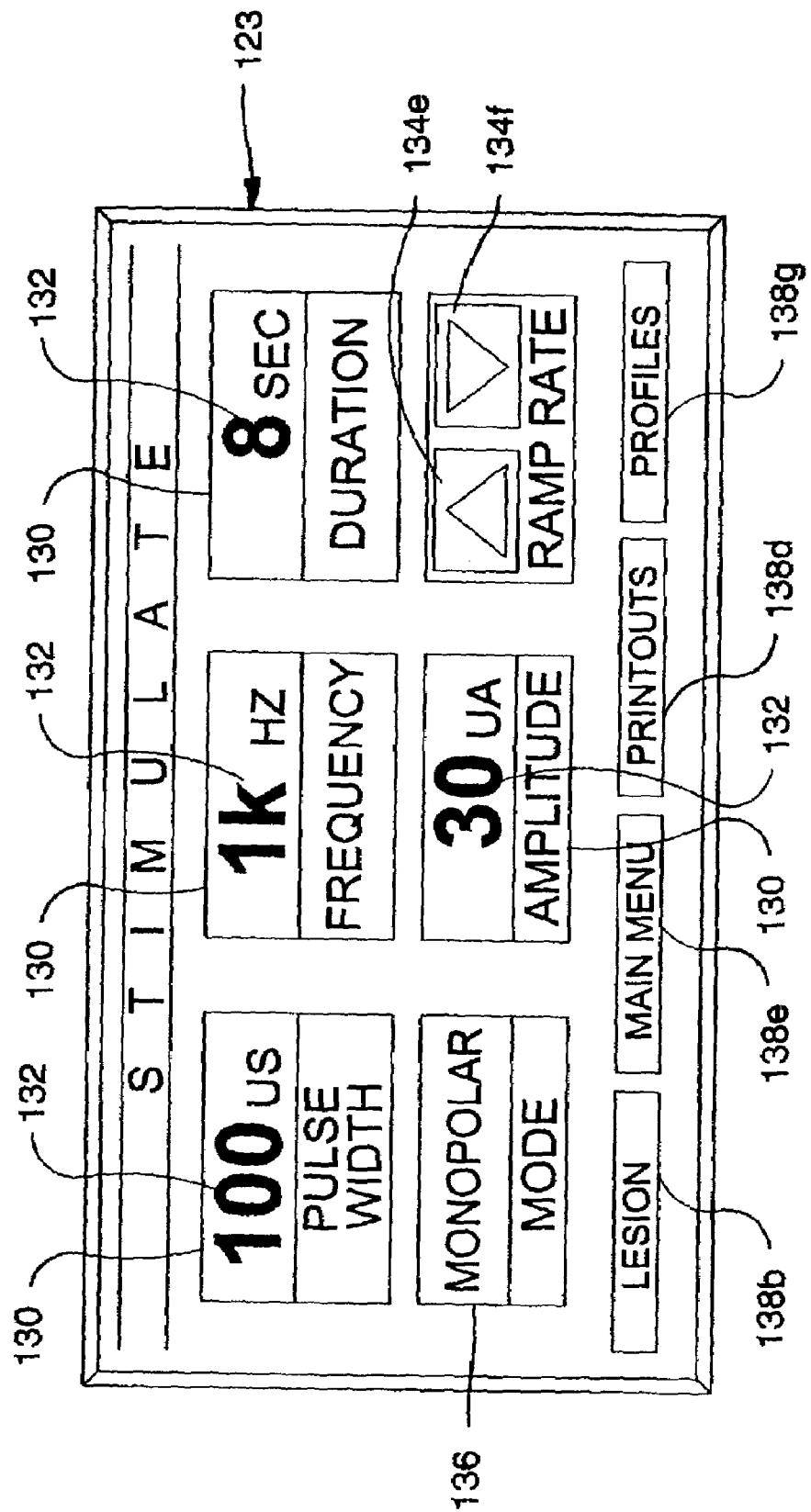
Figure 15E:
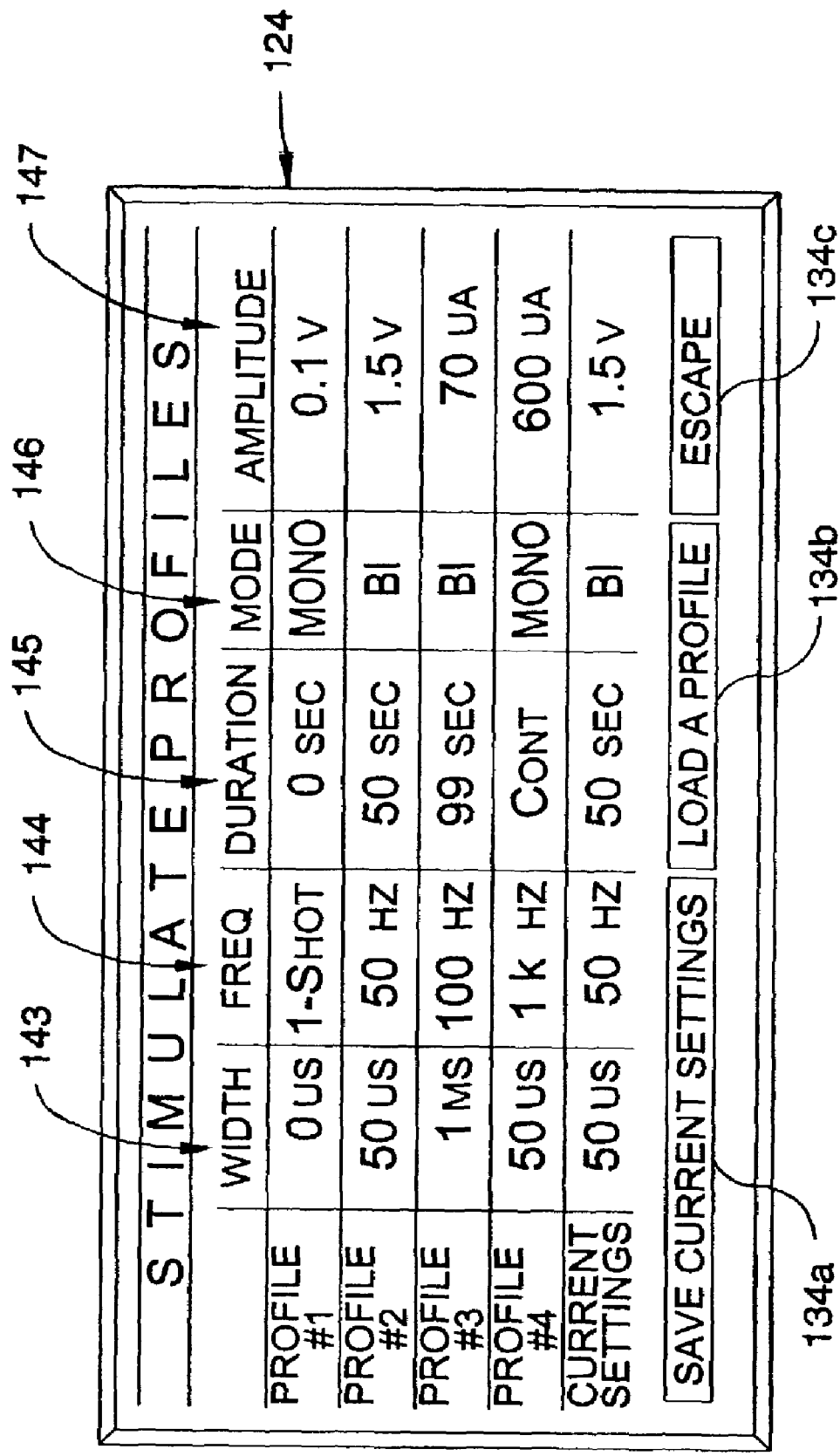

Referring to FIG. 15D in detail, the stimulate screen 123 includes onscreen menu buttons 138b, 138e, 138d and 138g for the lesion screen 121, the main menu screen 120, the printout screen 126 and a stimulate profiles screen 124 (FIG. 15E), respectively. The stimulate screen 123 also includes onscreen indicators 130 for pulse width, frequency, duration, mode and amplitude. The stimulate screen also includes onscreen software pushbuttons 134e and 134f for ramp rate up and ramp rate down, respectively. All the indicators 130 are also onscreen modifiable entry fields 132. For example, the user could select the onscreen indicator 130 for frequency by pressing an area around the onscreen indicator 130 for frequency which would bring up a pop-up menu having frequency values such as 0.5 kHz, 1 kHz, 2 kHz and the like. The only onscreen indicator 130 that is different is the mode onscreen indicator which is also a selector switch 136. When the mode onscreen indicator 130/selector switch 136 is pressed the mode merely toggles between monopolar and bipolar which changes the position of the monopolar mode relay K6003 accordingly. FIG. 15E shows that the stimulate profiles screen 124, similar to the lesion profiles screen 122, includes a table of user defined setup parameters or profiles (profile 1–profile 4) and a listing of current settings. The stimulate profiles screen 124 displays a pulse width 143, a frequency 144, a duration 145, a mode 146 and an amplitude 147. It is contemplated that the stimulated profiles screen 124 also includes an amperage setting, a temperature limit, and an alarm setting. In order to setup a profile, a user selects the parameters 143–147 for a particular profile (profile 1–profile 4) and then uses the save current settings onscreen pushbutton 134a to store the user profiles, profile 1–profile 4, into memory. To load a profile, the user selects the load a profile onscreen pushbutton 134b and the particular profile settings, profile 1–profile 4, are loaded into the current settings. Pressing the escape onscreen pushbutton 134c returns the user to the stimulate screen 123.

Figure 15F:
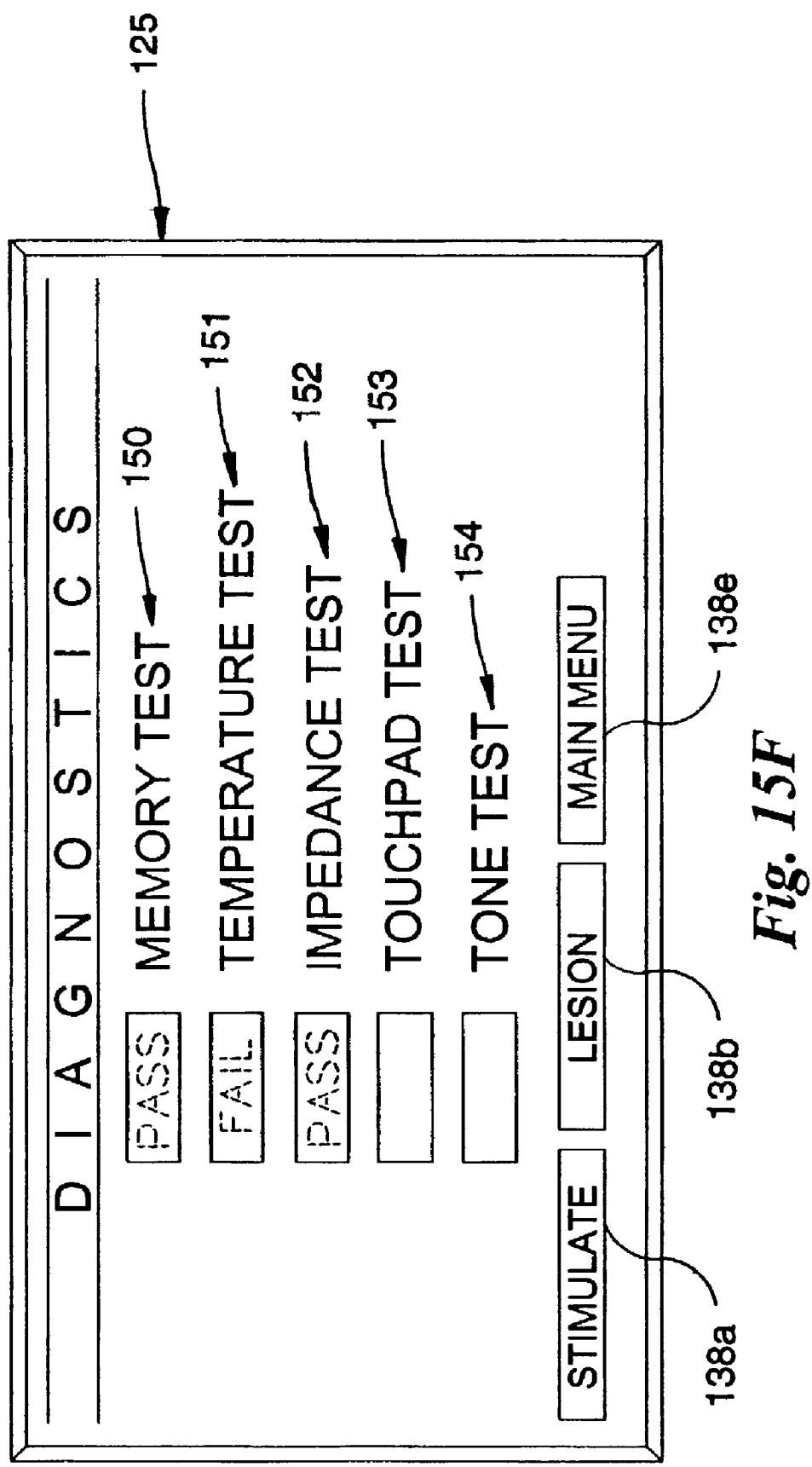

Referring to FIG. 15F in detail, the diagnostic screen 125 includes onscreen menu buttons 138a, 138b and 138e for the stimulate screen 123, the lesion screen 121 and the main menu screen 120, respectively. The diagnostic screen 125 also has onscreen pushbuttons 134 for a memory test 150, a temperature test 151, an impedance test 152, a touchpad test 153 and a tone test 154. When the user selects a particular test 150–154, the controller U1 runs diagnostic software and then displays whether the tests 150–154 passed or failed an in onscreen indicator 130 around the test fields 150–154. Obviously, other indication of diagnostics could be implemented without departing from the present invention.

Figure 15G:
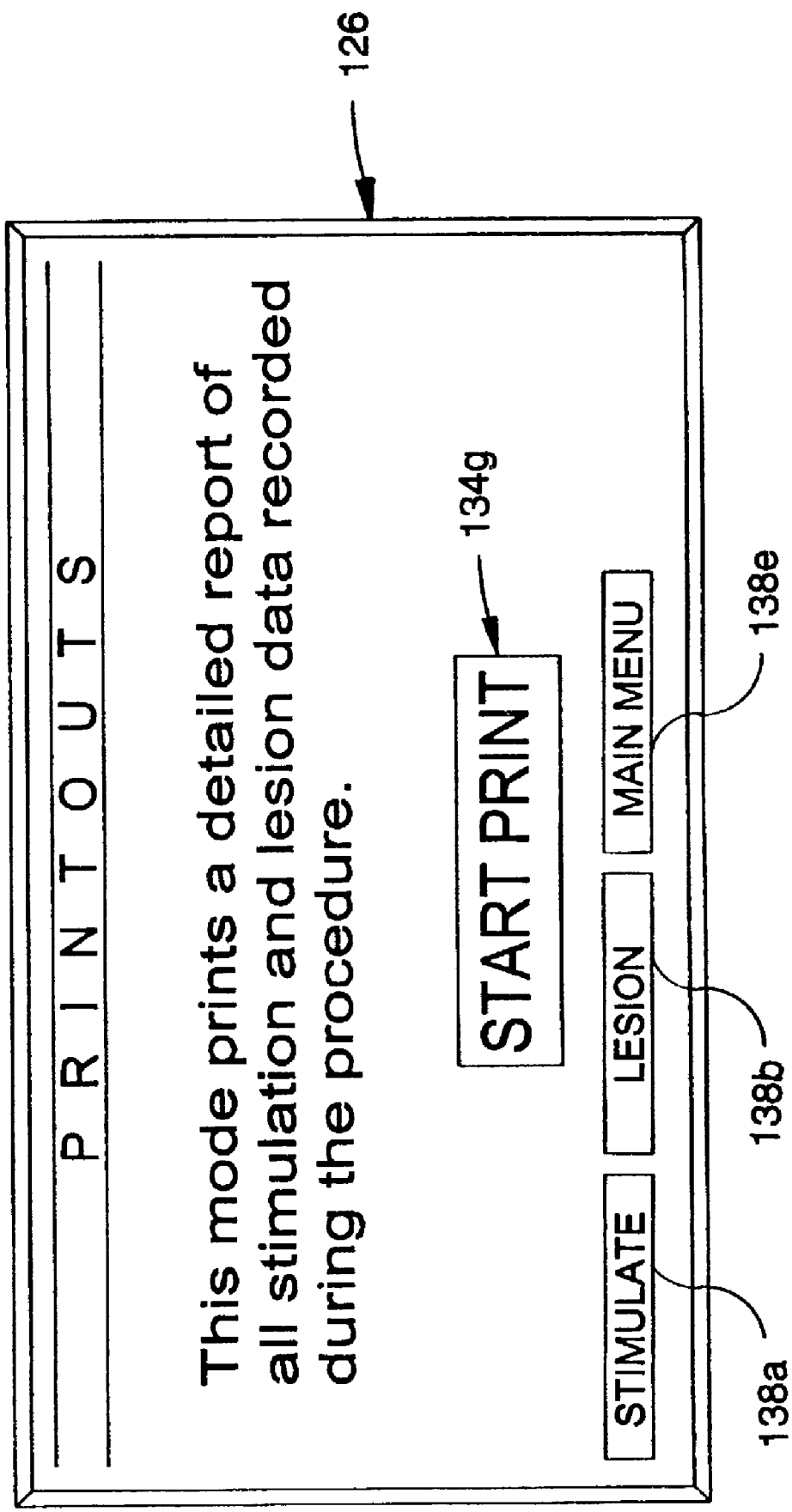

Referring to FIG. 15G in detail, the printout screen 126 has onscreen menu buttons 138a, 138b and 138e for the stimulate screen 123, the lesion screen 121 and the main menu screen 120, respectively, and an onscreen pushbutton 134g to start printing. As indicated on the printout screen 126 the onscreen pushbutton 134g for start print commands the RF generator 50 through the main controller U1 to output a detailed report of all stimulation and lesion data recorded during a procedure through data output port P6013.

Figure 17:
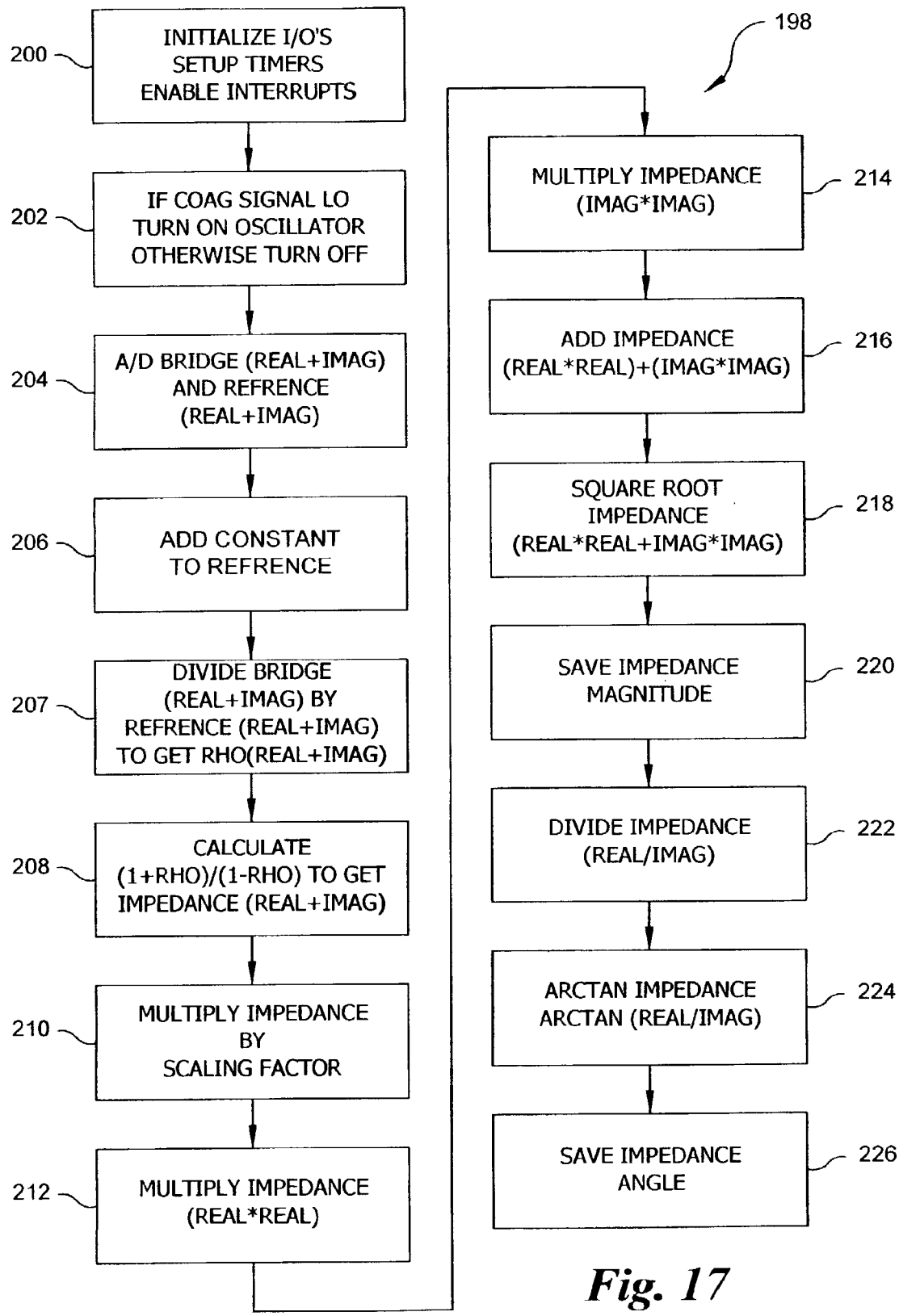
FIG. 17 is a flow chart depicting a synopsis of the software operation for impedance calculation for the control circuit of FIG. 2A.

FIG. 17 is a software flow chart of the impedance calculation software routine or impedance calculation routine 198 for the electrosurgical bipolar generator apparatus 50. The impedance calculation routine 198 runs in at least one of the controllers U1, U1102 or U1120, but preferably runs in the main controller U1 and the impedance controller U1120. The impedance monitoring circuit 76 detects an impedance as measured across the pair of leads of the bipolar electrodes 44a, 44b. The impedance is correspondingly proportional to an amount of cell destruction caused by the RF generator 50. The impedance monitoring circuit 76 uses the bridge detectors 100, 102 to measure an overall impedance signal and the reference detectors 104, 106 measure the impedance of the sine reference signal 20KHZ_REF. In Step 200 of the impedance calculation routine 198, I/O are initialized, timers are setup and interrupts are enabled in the impedance monitor controller U1120 and/or in the main controller U1. If a coagulation signal COAG from the main controller U1 (FIG. 12A) is determined to be low by the impedance controller U1120 (FIG. 11A), the impedance calculation routine 198 energizes an oscillator in Step 202. At Step 204, an A/D converter inputs the bridge detector signals from bridges 102, 100 (real and imaginary, respectively) measured from the impedance circuit 76 and the reference signals from the reference detectors 106, 104, (real and imaginary, respectively). The impedance calculation routine 198 adds a constant or a correction factor to the reference signals at Step 206. The correction factor is to compensate for losses in the circuit components due to non-ideal or real world component conditions. At Step 207, the impedance calculation routine 198 divides the bridge output values IMP_BRDG_I and IMP_BRDG_Q (real and imaginary, respectively) from the bridge I-channel circuit 103 and bridge Q-channel circuit 101 by the reference values IMP_REF_I and IMP_REF_Q (real and imaginary, respectively) from the reference I-channel circuit 107 and reference Q-channel circuit 105 to obtain RHO (real and imaginary) otherwise known as a reflection coefficient. Next at Step 208, the impedance calculation routine 198 calculates one plus RHO over one minus RHO to obtain the complex impedance (i.e., real and imaginary values) in Cartesian coordinates. The routine 198 then multiplies the impedance obtained at Step 208 by a scaling factor at Step 210. Using processor functions for multiplying and adding the real and imaginary stored variables of the actual impedance and taking the square root thereof at Steps 212–218, the impedance routine 198 obtains the magnitude of the impedance value and stores the magnitude value into memory at Step 220. Similarly, the impedance routine 198 uses processor functions to divide the real component of the actual impedance by the imaginary component of the actual impedance and then takes the arctangent of the result to obtain the phase angle or angle of the impedance at steps 222–224. The impedance routine 198 then stores the actual impedance angle at step 226.

Preferably, the impedance calculation routine 198 is used to detect an amount of cell destruction when using the RF generator 50. The user first measures a baseline impedance across the pair of leads of the bipolar electrodes 44a, 44b with the impedance monitoring circuit 76 when the leads are applied to an area of cell tissue just before either a coagulation operation or a cutting operation. The user implements the selected operation (i.e., cutting or coagulating) and the impedance monitoring circuit 76 measures the present impedance across the pair of leads of the bipolar electrodes 44a, 44b. The RF generator 50 determines the amount of cell destruction which has occurred by comparing the present impedance to the baseline impedance. The difference between the impedances is correspondingly proportional to the amount of cell destruction caused by the RF generator 50. Preferably, the controller U1 stops a selected operation after a predetermined level of cell destruction has occurred based upon the measured and compared impedance values. As mentioned above, preferably the measurement includes the overall signal in-phase components obtained through the bridge in-phase detector 102 and the overall signal quadrature component using the bridge quadrature detector 100 and includes the reference signal in-phase components obtained by the reference in-phase detector 106 and the reference signal quadrature components obtained by the reference quadrature detector 104. The in-phase and quadrature components are combined using Steps 200–220 of the impedance software in the impedance controller U1120 for both the baseline and the present impedance values in order to determine the magnitude and angle of the impedance.

FIGS. 18A–18B show a software flowchart for a lesion or temperature control software routine or simply lesion routine 228. The lesion routine 228 runs in at least one of the controllers U1, U1102 or U1120, but preferably runs in the main controller U1. The lesion screen 121 displays the temperature limit 140 and hold time 141 which are drawn or loaded at Step 230 of the lesion routine 228. The temperature is converted or scaled at Step 232 from the temperature input voltage signal THRMSTR conditioned by the temperature sense control circuit 74 as measured from the thermistor 72. At Step 234, the actual temperature measured and converted is loaded or displayed on the touchscreen 54. Similarly, the actual impedance as measured between the electrodes 44a, 44b and calculated by the impedance routine 198 is displayed on the touchscreen 54 at Step 236. An initial power level is determined at Step 238 using the actual probe temperature in comparison to the temperature limit 141. Steps 240–246 determine what input, if any, was received and determine where to proceed in the lesion routine 228. Step 240 determines whether the touchscreen 54 was touched or depressed. If the touchscreen was touched, the lesion routine 228 jumps to a sub-routine for entering a new temperature limit 140 or hold time at Step 242. Alternatively if the touchscreen 54 was not pressed, the lesion routine 228 determines whether the start button was pressed or not at Step 244. If the start button was not pressed, the lesion routine 228 determines at Step 246 whether the foot pedal was pressed. If the start button was pressed, the lesion routine 228 checks if the measured impedance is less than about 1500 ohms at Step 248. If the foot pedal was pressed and the start button was not pressed, the lesion routine 228 also checks if the impedance is less than about 1500 ohms at Step 248. If the foot pedal is not pressed, the lesion routine 228 jumps back to Step 232 to perform another temperature conversion. If the impedance is less than about 1500 ohms at Step 248, the lesion routine 228 goes to Step 249 to display "insert probe" and returns to the perform temperature conversion at Step 232. If the impedance is less than about 1500 ohms, the lesion routine 228 proceeds to Step 250 and turns on output power, illuminates an LED, and sounds a tone. Next at Step 252, the lesion routine 228 initializes flags and a delay counter. At Step 254, the lesion routine 228 checks for fault signals. At Step 256, the lesion routine 228 performs temperature conversion. At Step 258, the probe temperature and impedance are displayed. If the probe temperature is greater than the temperature limit 140 at Step 260, the delay counter is decreased by a predetermined number, in this case by five as shown at Step 261 and the lesion routine 228 proceeds to Step 264. If the probe temperature is not greater than the temperature limit 140 the lesion routine 228 proceeds to Step 262 where the delay counter is decreased by another predetermined number, in this case by one, before proceeding to Step 264. At step 264, the lesion routine 228 determines whether the delay counter has reached zero. If the delay counter equals zero, the lesion routine 228 proceeds to Step 266 where the delay counter is reloaded and subsequently proceeds to Step 268 to calculate the differential temperature between the probe temperature and the temperature limit 140. If the differential temperature is less than about four, the delay counter is increased by a differential temperature increase amount at Step 270. If the differential temperature is less than zero, the output power is decreased by a predetermined output power difference and a set limit reached flag is set at Step 272. If the differential temperature is greater than zero, the power output is increased by a factor of the differential temperature at Step 274. At Step 276, the hold timer is started, if it is not already started. When the temperature limit 140 is reached, the lesion routine 228 proceeds to Step 278 which displays the update hold timer. If the delay counter is not equal to zero at Step 264, the lesion routine 228 also proceed to Step 276 to start the hold timer. After the hold time display has been updated, the output power is turned off when the timer equals zero, the stop button is pressed or otherwise a loop condition has been met at Step 280.

FIGS. 19A–19B show a software flow chart for an RF power output software routine or RF output routine 298. The RF output routine 298 runs in at least one of the controllers U1, U1 102 or U1120, but preferably runs primarily in the main controller U1 and the RF output controller U1102. A jitter counter is loaded with a preset at Step 300 and a pointer is set to a random delay table at Step 302. At Step 304, a loop loads a predetermined count time into a first timer, TIMER1, and the first timer TIMER1 is started. At Step 306 a random delay time value is read from the table, randomly, and is loaded into a second timer, TIMER0, and subsequently the second timer TIMER0 is started. The jitter counter is decremented at Step 308. If the jitter counter equals zero, an invert jitter flag is set and the jitter counter is reset at Step 309 before proceeding to Step 310. However, if the jitter counter is not equal to zero, the jitter flag is checked at Step 310 to determine if it is equal to zero. If the jitter flag equals zero at Step 310, the RF output routine 298 proceeds or jumps to a second frequency sub-routine COAG_833 (FIG. 19C) at Step 311. However, if the jitter flag does not equal zero, the RF output routine 298 proceeds to a first frequency sub-routine COAG_1000 at Step 312 and a first byte of data is loaded into the first and second shift registers U1130, U1140. At step 312, the first and second shift registers U1130, U1140 are also started at a particular first frequency, in this case the first frequency is about 1 MHz. At Step 314, a second byte of data is loaded into the first and second shift registers U1130, U1140 and at Step 316 a third byte is loaded into the first and second shift registers U1130, U1140, and likewise fourth through ninth bytes are subsequently loaded into the first and second shift registers U1130, U1140, at Steps 318, 320, 322, 324, 326 and 328, respectively. At Step 330 (FIG. 19B), the second random delay timer TIMER0 is run until complete before proceeding to Step 332. At Step 332, the reset pointer is moved to the top of the random delay table if it is at the bottom or at some other predetermined return (to top) location. At Step 334, the first timer TIMER1 is checked. If the first timer TIMER1 is complete the routine moves to Step 336, and loads another preset time count into the first timer TIMER1. However, if the first timer TIMER1 is not complete the RF output routine 298 jumps back to Step 306 at Step 335. After loading the other preset time into the first timer TIMER1 at Step 336, the RF output routine 298 proceeds to Step 338 to determine if the foot pedal is being pressed or if there is a fault. The output is suspended for a suspension time at Step 340, in this case the suspension time is about 100 milliseconds, if a short circuit signal is activated. Next at Step 342, the first timer TIMER1 is checked. If the first timer TIMER1 is not complete the RF output routine 298 returns to Step 338. However, if the first timer TIMER1 is complete, the RF output routine 298 jumps back at Step 343 to Step 304.

Referring to FIG. 19C, the second frequency sub-routine COAG_833 is shown in Steps 344 through 361. At Step 344 through 360 other bytes are loaded into the first and second shift registers U1130, U1140 which preferably create a separate frequency different from the first frequency created from the bytes of data loaded at Steps 312 through 328 (FIG. 19A).

Steps 300–311 and 330–343 comprise a randomizer sub-routine. The randomizer sub-routine causes the RF output to switch between the first and second frequency sub-routines COAG_1000, COAG_833, generally randomly. A dedicated random generator or random generator circuit could also be implemented without departing from the present invention, thereby simplifying the RF output routine 298. Further, other methods of randomizing the selection between the first and second frequency sub-routines COAG_1000, COAG_833 could be implemented in the RF output routine 298 without departing from the present invention. The primary purpose of switching between the first and second frequency sub-routines COAG_1000, COAG_833, is to avoid unwanted collateral damage caused by a prolonged output at a single frequency. It has been observed during use of electrosurgical generators which output a single frequency for prolonged periods of time that such unwanted collateral damage occurs. It has also been observed that by randomly shifting between frequencies during use, such collateral damage can be avoided or at least minimized. Obviously other different frequencies could be loaded into the first and second frequency sub-routines COAG_1000, COAG_833 in order to vary the frequency between different first and second frequencies utilizing the shift routines and the random generator without departing from the broad inventive scope of the present invention.

It is further contemplated that any number of different output signals could be formed, having any number of different shapes and different frequencies, by substituting or changing the data loaded into the first and second frequency sub-routines COAG_1000, COAG_833. For example, outputs could be formed having the form of decaying sinusoids, decaying sawtooth waves, decaying square waves, or decaying combinations thereof. Preferably, the outputs are a combination of a decaying square wave and a decaying sinusoid.

From the foregoing, it can be seen that the present invention comprises an electrosurgical generator apparatus using radio frequency (RF) modulation and having a unique user interface. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A control circuit that controls a variable output signal to electrodes used in electrosurgical procedures, the control circuit comprising:
    (a) a DC power supply circuit that provides regulated low voltage and high voltage outputs; and
    (b) a radio frequency (RF) waveform generator circuit that provides pulse duration modulation of a carrier signal, the carrier signal directly affecting the variable output signal to the electrodes, the RF waveform generator circuit generating a plurality of different user selectable waveforms based on the pulse duration modulation of the carrier signal.

2. The control circuit according to claim 1, wherein the RF waveform generator circuit includes at least one shift register integrated circuit (IC) device and a random generator that causes the variable output signal to switch generally randomly between a first frequency and a second frequency.

3. The control circuit according to claim 1, wherein the RF waveform generator circuit includes two shift register integrated circuit (IC) devices and a processor, the processor controllably coupled to the two shift register IC devices, the processor including a randomizer routine that causes the variable output signal to switch generally randomly between a first frequency and a second frequency.

4. The control circuit according to claim 1, wherein the plurality of different user selectable waveforms based on the pulse duration modulation of the carrier signal include one or more of decaying sinusoids, decaying sawtooth waves, decaying square waves, and combinations thereof.

5. An electrosurgical generator apparatus that controls a variable output signal to electrodes, the generator apparatus operating in either a cut mode or a coagulation mode, the generator apparatus comprising:
- (a) a DC power supply that provides regulated low voltage and high voltage outputs; and
- (b) a radio frequency (RF) waveform generator circuit that provides pulse duration modulation of a carrier signal, the carrier signal directly affecting the variable output signal to the electrodes, the RF waveform generator circuit generating a plurality of different user selectable waveforms based on the pulse duration modulation of the carrier signal.

6. The electrosurgical generator apparatus of claim 5, further comprising:
- (c) a touchscreen interface that communicates with the controller to display the data from the memory and that allows a user to enter a setting.

7. The electrosurgical generator apparatus of claim 5, further comprising:
- (c) a controller for controlling the generator apparatus;
- (d) a memory that stores data for the controller; and
- (e) a touchscreen interface that communicates with the controller to display the data from the memory and that allows a user to enter a setting.

8. The electrosurgical generator apparatus of claim 7, wherein the touchscreen interface displays at least one of a pulse width setting, a frequency setting, a voltage setting, an amperage setting, a measured temperature value, a temperature setpoint value, a measured impedance value, an actual time, an elapsed time, a remaining time, and a time setpoint value.

9. The electrosurgical generator apparatus of claim 7, wherein the touchscreen interface is configured for receiving entry of at least one of a pulse width setting, a frequency setting, a voltage setting, an amperage setting, a temperature setpoint value, and time setpoint value.

10. The electrosurgical generator apparatus of claim 7, wherein the touchscreen interface has an on-screen software pushbutton having a first state and a second state.

11. The electrosurgical generator apparatus of claim 7, wherein the touchscreen interface has an on-screen software selector switch having a first position and a second position.

12. The electrosurgical generator apparatus of claim 5, further comprising:
- (c) an impedance monitoring circuit that detects an impedance as measured across a pair of leads of the electrodes, the impedance being correspondingly proportional to an amount of cell destruction caused by the generator apparatus.

* * * * *